United States Patent
Snow et al.

(10) Patent No.: US 6,350,431 B1
(45) Date of Patent: Feb. 26, 2002

(54) COMPOUNDS

(75) Inventors: Robert Allen Snow, West Chester, PA (US); Paul Mark Henrichs, Houston, TX (US); Daniel Joseph Delecki, Radnor, PA (US); William Anthony Sanderson, deceased, late of Wayne, PA (US), by Audrey W. Sanderson, attorney-in-fact; Vinay Chandrakant Desai, Phoenixville, PA (US); Edward Bacon, Audubon, PA (US); Kenneth Robert Hollister, Chester Springs, PA (US); Eric Paul Hohenschuh, Berwyn, PA (US)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/429,347

(22) Filed: Oct. 28, 1999

Related U.S. Application Data

(63) Continuation of application No. PCT/GB98/01244, filed on Apr. 29, 1998, which is a continuation-in-part of application No. 09/035,285, filed on Mar. 5, 1998, now abandoned, and a continuation-in-part of application No. 08/848,586, filed on Apr. 29, 1997, now abandoned.

(30) Foreign Application Priority Data

Dec. 22, 1997 (GB) .............................................. 9727124

(51) Int. Cl.$^7$ ...................... A61K 49/00; C07D 209/62
(52) U.S. Cl. ............................. 424/9.6; 548/3; 548/223; 549/402; 549/427; 549/455
(58) Field of Search ............................... 424/9.6; 548/3, 548/223; 549/402, 455, 427

(56) References Cited

U.S. PATENT DOCUMENTS 5,622,685 A    4/1997   Sinn et al. .................. 424/1.65

FOREIGN PATENT DOCUMENTS

| DE | 40 17 439 A | 12/1991 |
| EP | 0 536 480 A | 4/1993 |
| WO | WO 92 00748 A | 1/1992 |
| WO | WO 95 25093 A | 9/1995 |

OTHER PUBLICATIONS

Chemical Abstracts, 158328;121;14, Oct. 3, 1994, Columbus, OH, Salhi, Samira et al., "New polymeric materials: porphyrins attached to preformed polystyrene", XP002077426.

*Primary Examiner*—Richard L. Raymond
(74) *Attorney, Agent, or Firm*—Bacon & Thomas

(57) ABSTRACT

This invention provides a physiologically tolerable light imaging contrast agent compound having a molecular weight in the range 500 to 5000000 and containing at least two chromophores having delocalized electron systems as well as at least one polyalkylene oxide (PAO) moiety having a molecular weight in the range 60 to 100000.

28 Claims, 18 Drawing Sheets

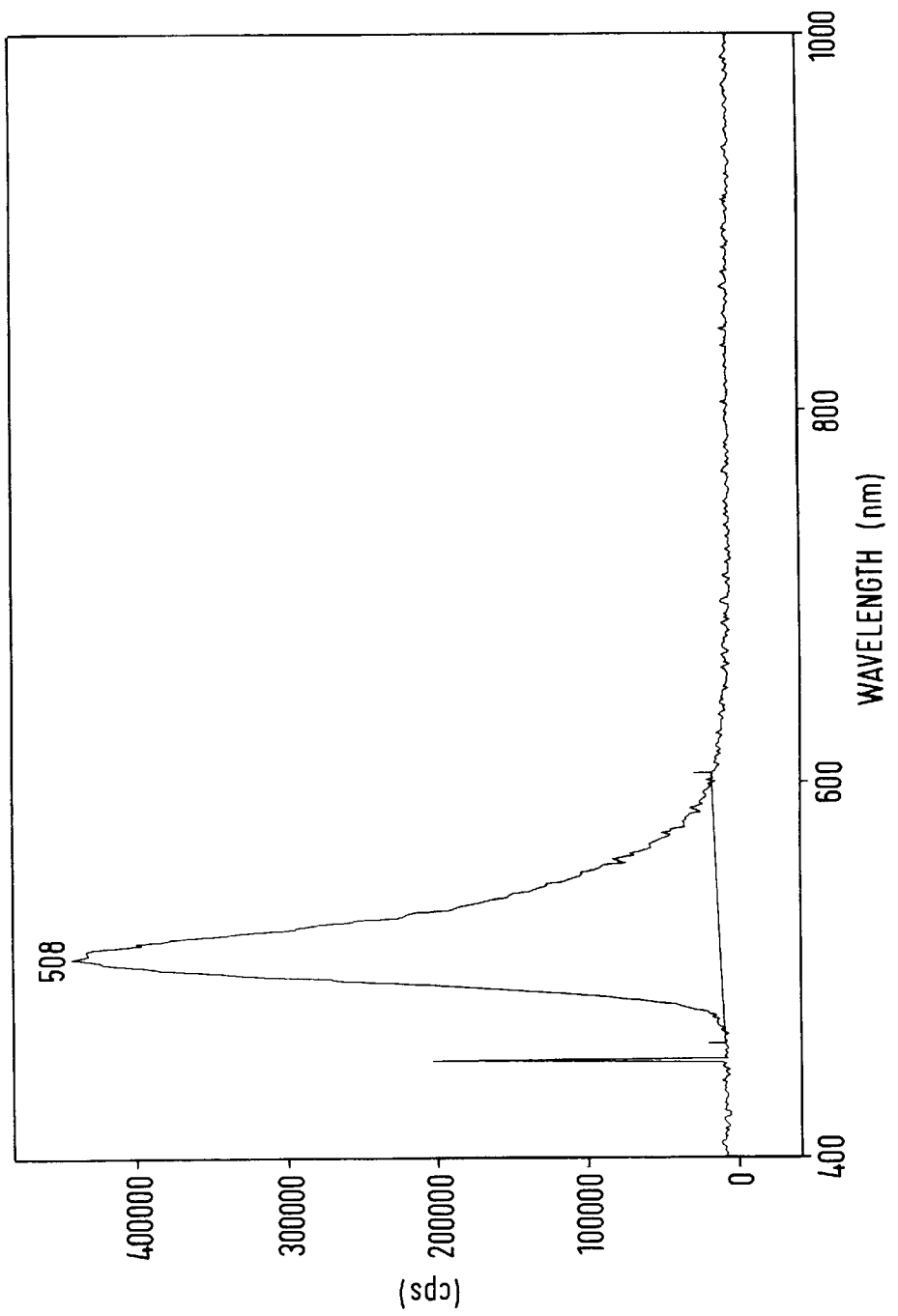

COMPOUNDS

This application is a continuation of international application No. PCT/GB98/01244 filed Apr. 29, 1998 (of which the entire disclosure of the pending, prior application is hereby incorporated by reference), which itself is a CIP of U.S. application Ser. No. 08/848,586 filed Apr. 29, 1997, now abandoned, and a CIP of U.S. application Ser. No. 09/035,285 filed Mar. 5, 1998, now abandoned.

This invention relates to compounds useful as contrast agents in light imaging procedures, in particular compounds containing a plurality of chromophores as well as one or more hydrophilic polyalkylene oxide (PAO) moieties.

The use in diagnostic imaging procedures of materials (contrast agents) which enhance image contrast is well established.

In light imaging procedures, the contrast agents will generally act as light scatterers or as light absorbers or emitters. The present invention is concerned with contrast agents which contain chromophores and thus absorb or emit light.

As used in this application, "light imaging" refers to diagnostic procedures that result in an image of the interior of the body or of the surface of the body by a process involving propagation through or reflection from the body of electromagnetic radiation with a wavelength in the range 300 to 1300 nm. The propagating electromagnetic radiation can result either from irradiation of the body or a portion of the body with light in the specified wavelength range or by generation of light within the wavelength range in the body or on the surface of the body by processes such as bioluminescence, sonoluminescence, or fluorescence.

The propagating light can be detected directly with sensors at the surface or within the body or indirectly after the generation from the light of another form of energy such as sound, ultrasound, heat, or electromagnetic radiation outside of the wavelength range 300 to 1300 nm. A sensor is a device that converts the detected light, sound, ultrasound, heat or other form of signal into a recordable form such as electrical current. An example of a light sensor is a photomultiplier tube. A sensor for light may also consist of a fiber-optic cable leading from the point of detection to a photomultiplier tube. In a simple embodiment of light imaging the sensor consists of the human eye.

By chromophore is meant a group in a composition of matter, eg. an organic or inorganic group which absorbs and/or emits light. The term thus includes fluorophores, groups which are fluorescent, as well as phosphorescent groups. In general chromophores will contain a complexed metal ion or an extensive delocalized electron system. One aspect of the present invention is particularly concerned with the latter type. A compound containing a chromophore is sometimes herein referred to as a chromophore.

By light is meant electromagnetic radiation having wavelengths from 300–1300 nm. Chromophores having absorption and/or emission maxima in the visible to far infra-red range are particularly relevant to the invention.

While certain small organic chromophore-containing molecules, such as indocyanine green, have been used as contrast agents in light imaging procedures, their utility is limited as they are relatively rapidly cleared from the blood stream and hence provide a relatively short or narrow imaging window.

It is thus an objective of the invention to provide light imaging contrast agents which provide the user with an extended imaging window and thus are suitable for example for studies of blood flow, of perfusion of effusion, and of the vascularization of sites of interest.

Thus viewed from one aspect the invention provides a physiologically tolerable water-soluble light imaging contrast agent compound having a molecular weight in the range 500 to 500000 and containing at least two chromophores having delocalized electron systems as well as at least one polyalkylene oxide moiety having a molecular weight in the range 60 to 100000, preferably 200 to 100000, more preferably 250 to 50000, especially preferably 250 to 25000 and more especially preferably 400 to 15000, and preferably wherein said chromophores are not lanthanide chelates unless said agent also comprises a chelated Tc, Sm, or Cu radionuclide, and more preferably said chromophores are not chelated lanthanides.

The polyalkylene oxide PAO moiety can be linear or branched and is preferably a homopolymeric or copolymeric, especially block copolymeric, moiety containing repeat units $C_nH_{2n}O$ where n is 2,3 or 4, preferably 2 or 3, especially preferably $CH_2CH_2O$, $OCHCH_3CH_2$, $CH_3CHCH_2O$ or $CH_2CH_2CH_2O$ repeat units. Within the PAO moiety, one or more, preferably one or two, of the ether oxygens may be replaced by an amine group NH or NE where E is a bond or an alkyl or hydroxyalkyl group or a $(C_nH_{2n}O)_qE'$ side chain (where n is 2,3 or 4 and q is an integer, the maximum value for which is set by the molecular weight limit for the PAO and E' is H or alkyl, a chemical bond or a chromophore).

Any alkyl, alkenyl or alkynyl moieties, unless otherwise defined, preferably have up to 12, especially preferably up to 6 carbons.

The compounds of the invention preferably have a polymer structure with repeat units containing both a chromophore and a polyalkylene oxide moiety. At the lower limit of such a polymer structure, the compounds may simply contain two chromophores and a polyalkylene oxide moiety. The compounds of the invention may thus be of or contain a moiety of formula I $$\text{Chr-L[PAO-L-Chr]}_n \qquad (I)$$

where each Chr which may be the same or different is a chromophore, each PAO which may be the same or different is a polyalkylene oxide moiety, each L is a bond or organic linking group connecting at least one PAO to at least one Chr, and n is an integer having a value of at least 1 (the upper limit for n being determined by the molecular weight limit for the compounds of the invention).

As used herein, the term "linking group" is a chemical moiety that connects together at least two molecules, at least the residue of one molecule with another molecule, or at least the residue of one molecule with the residue of another molecule.

The unit [PAO-L-Chr] will allow for the polymer to be branched or alternatively to be linear. Examples of such structures include:

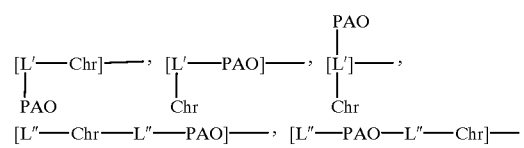

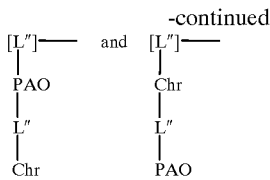

where L' and L" are bonds or linker groups as mentioned above. Thus, when [PAO-L-Chr] is a repeat unit in a polymer, the PAO and Chr moieties may form part of or may be pendant from the polymer backbone. Similarly the repeat unit [PAO-L-Chr] may contain more than one chromophore or more than one PAO moiety.

Alternatively the compounds of the invention may comprise a branched polymer, such as a dendrimer or cascade polymer, with PAO and Chr moieties attached to polymer termini. As used herein, a branched polymer is a polyalkylene oxide moiety which contains at least one branching group to which is attached at least one additional polyalkylene oxidyl group.

In one aspect, a branching group in the backbone of the polyalkylene oxide moiety can be selected from the group consisting of a nitrogen atom and a carbon atom. At least one additional polyalkylene oxidyl group can be attached to the branching group by a chemical bond selected from the group consisting of carbon-carbon, carbon-nitrogen, and carbon-oxygen chemical bonds, or by a linking group.

Preferred linking groups to a nitrogen branching group include:

methylene groups, [—$CH_2$—];

poly(methylene) groups, [—($CH_2$)$_n$—] wherein n is an integer from 2 to about 16, such as can be formed by reaction between a nitrogen NH group and an alkylenyl group containing a terminal halide (e.g., Cl, Br, I) or sulfonate group (e.g., methanesulfonate, toluenesulfonate, benzenesulfonate and the like);

alkylenecarbonyl groups [—($CH_2$)$_{n''}$—C(=O)—] wherein n" is an integer from 1 to about 16 such as can be formed by reacting an NH group with a haloalkylenecarbonyl group;

ethylenesulfonylethylene groups [—$CH_2CH_2$—S(=O)$_2$—$CH_2CH_2$—], such as can be formed by reacting an NH group with a vinylsulfonylethylene group [$CH_2$=CH—S(=O)$_2$—$CH_2CH_2$—];

ethylenesulfonylmethyl-eneoxymethylenesulfonylethylene groups [—$CH_2CH_2$—S(=O)$_2$—$CH_2$—O—$CH_2$—S(=O)$_2$—$CH_2CH_2$—], such as can be formed by reacting an NH group with a vinylsulfonylmethyleneoxymethylenesulfonylethylene group [$CH_2$=CH—S(=O)$_2$—$CH_2$—O—$CH_2$—S(=O)$_2$—$CH_2CH_2$—];

ethylenesulfonylmethylenesulfonylethylene groups [—$CH_2CH_2$—S(=O)$_2$—$CH_2$—S(=O)$_2$—$CH_2CH_2$—], such as can be formed by reacting an NH branching group with a vinylsulfonylmethylenesulfonylethylene group [$CH_2$=CH—S(=O)$_2$—$CH_2$—S(=O)$_2$—$CH_2CH_2$—];

carbonyl groups [—(C=O)—] which can comprise an amide linking group formed, for example, by reacting an NH branching group with an activated ester such an N-hydroxysuccinimidyl- ester, or with a mixed anhydride such as a trifluoromethyloxycarbonyl-, or with an acid halide such as an acid chloride, e.g., Cl—(C=O)—;

sulfonyl groups [—S(=O)$_2$—] which can comprise a sulfonamide linking group formed, for example, by reacting an NH branching group with a sulfonyl halide such as a polyalkylene oxidylalkylenesulfonyl chloride, e.g., Cl—S(=O)$_2$—($CH_2$)$_n$—O-PAO; wherein n is an integer from 2 to about 16 and PAO is a polyalkylene oxidyl group;

carbonyloxy groups [—C(=O)—O—] such as those found in urethane groups such as can be obtained by reacting a polyalkyleneoxy group with phosgene and then with an NH group;

thiocarbonyl groups [—(C=S)—] such as those found in thiourethane groups such as can be obtained by reacting a polyalkyleneoxy group with thiophosgene and then with an NH group;

alkylenecarbonyloxymethyleneoxycarbonylalkylene groups [—(—$CH_2$—)$_{n'}$—C(=O)—O—C(R'R")—O—C(=O)—(—$CH_2$—)$_{n'}$—] where each n' is independently selected from the group of integers from 1 to 16 and each R' and R" is independently selected from the group consisting of H and methyl; and, carbonylalkylenecarbonyl groups [—C(=O)—($CH_2$)$_w$—C(=O)—] wherein w is an integer from 1 to about 6, such as succinate and adipate.

Preferred linking groups to a carbon branching group include:

ether groups [—O—];

thioether groups [—S—];

thiosulfoxide groups [—S(=O)—];

thiosulfonyl groups [—S(=O)$_2$—];

oxycarbonyl groups [—O—C(=O)—];

aminocarbonyl groups [—NH—C(=O)—];

carbonyl groups [—(C=O)—];

carbonyloxy groups [—C(=O)—O—];

carbonate groups [—O—C(=O)—O—];

carbonyloxymethyleneoxycarbonylalkylene groups [—(—C(=O)—O—C(R'R")—O—C(=O)—(—$CH_2$—)$_{n'}$—] where n' is an integer from 1 to 16 and each R' and R" is independently selected from the group consisting of H and methyl;

urethane groups [—O—C(=O)—NH—]; and thiourethane groups [—O—(C=S)—NH—].

In another aspect, a branching group can comprise the unit —$NR_1$—$CR_2R_3$—$CR_4R_5$— wherein $R_1$ can be selected from the group consisting of H, an alkyl group of from 1 to about 16 carbon atoms which may be linear, branched, saturated, unsaturated, or contain a carbocyclic ring of from 3 to about 10 carbon atoms, or a carbonylalkyl group wherein the alkyl group is defined immediately above;

$R_2$, and $R_3$, are independently selected from the group consisting of H, an alkylene group of from 1 to about 16 carbon atoms, which may be linear, branched, saturated or unsaturated, and can contain a carbocyclic ring of from 3 to about 10 carbon atoms and to which is attached a polyalkylene oxidyl group through a heteroatom group selected from the group consisting of NH, O, S, O—C(=O), and C(=O)—O, e.g., such as 4-(polyalkyleneoxyethylcarbonylaminobutyl), [PAO-$CH_2CH_2C$(=O)NH—($CH_2$)$_4$—], 2-(polyalkyleneoxycarbonyl)ethyl, [PAO-C(=O)$CH_2CH_2$—], polyalkyleneoxycarbonylmethyl, [PAO-C(=O)$CH_2$—], polyalkyleneoxyethylaminocarbonylmethyl, [PAO-$CH_2CH_2$NHC(=O)$CH_2$—], polyalkyleneoxyethylaminocarbonylethyl, [PAO-$CH_2CH_2$NHC(=O)$CH_2CH_2$—], polyalkyleneoxymethyl,

[C], and polyalkyleneoxyethylthiomethyl, [PAO-CH₂CH₂—S—CH₂—];

R₄, and R₅, are independently selected from the group consisting of H, an alkyl group of from 1 to about 16 carbon atoms which may be linear, branched, saturated, unsaturated, or contain a carbocyclic ring of from 3 to about 10 carbon atoms, or a carbonylalkyl group wherein the alkyl group is defined above, or, preferably, where both R₄, and R₅, are taken together form a carbonyl group;

and wherein at least one of R₂,R₃, is not H.

Preferred units —NR₁—CR₂,R₃—CR₄,R₅,— are selected from the group consisting of lysine, aspartic acid, glutamic acid, cysteine, and serine in the backbone of the polyalkylene oxide moiety and contain least one additional polyalkylene oxide attached, for example, to the epsilon amine site of lysine, to the gamma carboxylic acid site of aspartic acid, to the delta carboxylic acid site of glutamic acid, to the beta sulfhydryl group in cysteine, and to the beta hydroxy site of serine.

In another aspect, one branching group and a carbon atom in the backbone of the polyalkylene oxide moiety or two branching groups in the backbone of the polyalkylene oxide moiety can be joined by an alkylene group of from 2 to 12 carbon atoms. The alkylene group can be linear or branched such as ethylene, propylene, butylene, isobutylene, pentylene, hexylene, octylene, decylene, and dodecylene. The alkylene group can be saturated or unsaturated such as 2-butenylidene, isoprenylene, and 2-butynylidene. In another aspect, the alkylene group can comprise a saturated or unsaturated cyclic group such as cyclopropylidene, cyclobutylidene, 1,2-cyclopentylidene, 1,3-cyclopentylidene, 1,2-cyclohexylidene, 1,3-cyclohexylidene, 1,4-cyclohexylidene, a cyclohexenylidene ring such as can be formed by a Diels-Alder reaction between a diene and a dieneophile, 1,4-cycloheylidenebismethylene, ethylene-1,2-cyclopropylidenemethylene, 1,1-spirocycloproylidenebismethylene, and the like, and which can contain an oxygen or sulfur ether atom, such as a 2,5-tetrahydrofuranylene group and a 2,6-tetrahydropyranylene group.

In another aspect, one branching group and a carbon atom in the backbone of the polyalkylene oxide moiety or two branching groups in the backbone of the polyalkylene oxide moiety can be separated by an aromatic ring of 6 to 14 carbon atoms such as p-phenylene, or m-phenylene, or m-toluidene, 9,10-anthracenylidene, or 1,4-naphthalenylidene, or an aralkylene group such as p-phenylenebismethylene, or 9,10-anthracenylidenebismethylene, and which aromatic ring can comprise a 5- or 6-membered heterocyclylene group containing one or two heteroatoms selected from the group consisting of nitrogen, oxygen, and sulfur such a 2,6-pyridinylene, 1,4-imidazolidene, 5,8-quinolinylidene, and 1,1-spiro-2,6-dithiacyclohexylene, or a symmetrical triazinylene group.

In this event, the compound will have the formula II

L'''(Chr)ₘ(PAO)ₚ (II)

where L''' is a branched polymer with Chr and PAO groups attached, m is an integer having a value of at least two, and p is an integer having a value of at least one (the maximum values of m and p being determined by the number of terminal attachment sites on L''').

In general, it is preferred that the compounds of the invention should contain Chr and PAO groups in a ratio which is greater than 1:1 in favour of the chromophore.

The compounds of formula III

Chr[L*-PAO-L*-Chr]ₙ (III)

(where Chr, PAO and n are as defined above, and each L* is a bond or an organic linker moiety) are especially preferred. Such compounds contain one more Chr moiety than PAO moiety.

The compounds of formula IV

(IV)

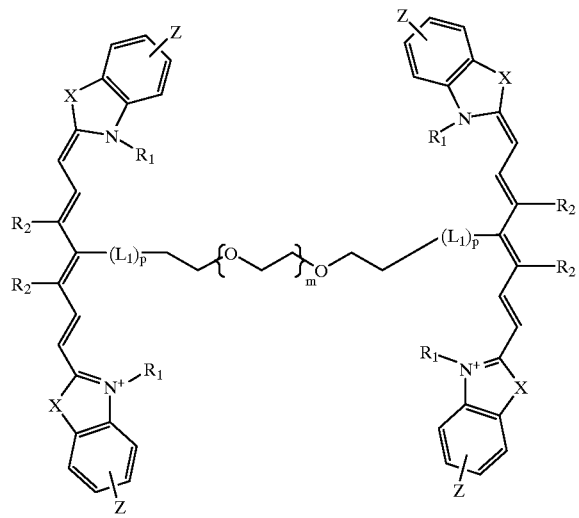

are more especially preferred wherein each L₁ is a group independently selected from the group consisting of an organic linker moiety and a chemical bond;

each X is independently selected from the group consisting of O, N—R₁, S, Se, Te, CH=CH and (CH₃)₂C;

each R₁ is independently selected from the group consisting of a methyl group, an ethyl group, and a C₃₋₁₆ alkyl group optionally containing one or more heteroatoms selected from the group consisting of O, N, and S, which heteroatoms are separated from one another by at least 2 carbon atoms, and which ethyl and alkyl groups optionally contain one or more hydrophilic functional groups selected from the group consisting of hydroxyl groups, carboxyl groups, sulfonate groups, sulfate groups, phosphate groups, phosphonate groups, amino groups, amino acid groups;

examples of hydrophilic groups on R₁ groups include C₅₋₁₀ carbohydrate groups, carboxylate groups and C₂₋₁₀ oxycarbonylalkyl groups, dihydroxypropyl groups, and the like;

each Z, of which there is at least one, is independently selected from the group consisting of H, a methyl group, an ethyl group as defined above, a C₃₋₁₆ alkyl group as defined above, a C₁₋₁₆ alkoxyl group, the alkyl portion of which is as defined above, a C₁₋₁₆ carboxyalkyl group, a C₁₋₁₆ oxycarbonylalkyl group, a sulfonate group, a hydroxyl group, a phosphate group, a C₁₋₁₆ sulfonamidoalkyl group, a phenyl-C₁₋₁₆-alkyl group, a phenoxy-C₁₋₁₆-alkyl group, a C₁₋₁₆ phenyloxyalkyl group, an oxyphenoxy-C₁₋₁₆-alkyl group, the alkyl portions each of which are as defined above, or an annulated aromatic ring which comprises a benz[e] aromatic ring, a benz[f]aromatic ring, or a benz[g]

aromatic ring, where e, f, and g are defined relative to the indole structure as a template and each of which may be substituted by $C_{1-16}$ alkyl, $C_{1-16}$ alkoxyl, carboxyl, sulfonate, sulfonamido, phenyl, or phenoxyl groups as defined above;

each $R_2$ is independently selected from the group consisting of H, $C_{1-16}$ alkyl as defined above, or two $R_2$ groups together with the three intervening carbons form a 5 or 6 membered carbocyclic ring optionally containing a ring heteroatom selected from the group consisting of O, N—$R_1$ and S;

m is an integer up to 1200, preferably from 5 to 1200, more preferably from 50 to 1000; and each p independently is 0 or 1 when $L_1$ is an organic linker moiety.

Viewed from a further aspect the invention consists of oligomeric Chr-(PAO-Chr)$_n$ compounds which can be formed by oligomerization of difunctional chromophores and difunctional PAO moieties. The polyalkylene oxide PAO moiety is preferably a homopolymeric or copolymeric, especially block copolymeric, moiety containing repeat units as discussed above. Particularly preferred are hydrophilic polymers comprising difunctional PAO moieties substituted with a carboxylate group on one end and an amino group on the other end. These bifunctional hydrophilic polymers are preferred since they possess various similarities to amino acids. In this case, an amino acid such as lysine or aspartic acid or cysteine can be added to the end of the PAO moiety via standard amide forming chemistry used in peptide synthesis. Generally, these amino acid groups can contain more than one site of additional reactivity for peptide bond formation or for polymerization or for attachment to chromophores and for attachment to targeting vectors but these sites of reactivity are temporarily blocked as they are in peptide synthesis. One of the blocked sites can be deblocked to permit additional polymerization, reaction with chromophores, targeting vectors, polymers, and the like while leaving other sites blocked. Once a desired oligomer or polymer is formed as a precursor to a final state, then the blocking groups can be removed and the liberated reactive sites can be further reacted to attach chromophores, targeting vectors, polymers, and the like.

Bifunctional hydrophilic polymers, and especially bifunctional PAOs, may be synthesized using standard organic synthetic methodologies. In addition, many of these materials are available commercially. For example, α-amino-ω-carboxy PEG, dicarboxy-PEG, disulfhydryl-PEG and diamino-PEG are commercially available from Shearwater Polymers (Huntsville, Ala.). Other useful materials such as Tetronic and Pluronic PAO's are commercially available from BASF, and Jeffamines commercially available from Dixie Chemical Co. Tetronic is particularly useful in the present invention since it will tend to cleect at the tumor margin and hence facilitate complete removal of the tumor.

The PAO moieties are preferably attached to the chromophore moieties by covalent bonds. Preferably, the chromophore moieties comprise at least one infrared and/or visible absorbing or emitting chromophore.

Viewed from a further aspect the invention provides a method of treatment of the human or animal (e.g. mammalian, avian or reptilian) body to remove tumorous tissues therefrom, wherein an effective amount of a light-imaging contrast agent compound is administered to said body and allowed to accumulate at tumorous tissue or cells therein and wherein tumorous tissue or cells at which said compound has accumulated is removed or destroyed in situ, the improvement comprising using as said contrast agent compound a compound having a molecular weight in the range 500 to 500000 and containing at least two chromophores having delocalized electron systems as well as at least one polyalkylene oxide moiety having a molecular weight in the range 60 to 100000, preferably 200 to 100000, more preferably 250 to 50000, especially preferably 250 to 25000 and more especially preferably 400 to 15000.

Methods of removal of diseased tissue or cells, such as tumors, include surgical excision as a preferred method. Surgical excision includes but is not limited to techniques such as endoscopic and laproscopic assisted surgery, laser assisted surgery, microsurgery, surgical excision along a surgical plane, PDT, SDT and cryogenic methods such as cryosurgery chemical destruction/surgery (application of caustic substances). Additional methods include but are not limited to photodynamic therapy (PDT), microwave therapy, laser ablation therapy, hyperthermic therapy, radiation therapy with x-rays, radiation therapy with radioisotopes, sonodynamic therapy (SDT), and combinations thereof.

Viewed from a still further aspect the invention provides the use of a physiologically tolerable water-soluble light-imaging contrast agent compound having a molecular weight in the range 500 to 500000 and containing at least two chromophores having delocalized electron systems as well as at least one polyalkylene oxide moiety having a molecular weight in the range 60 to 100000, preferably 200 to 100000, more preferably 250 to 50000, especially preferably 250 to 25000 and more especially preferably 400 to 15000, for the manufacture of a medicament for use in a method of treatment of the human or animal body to remove tumorous tissue or cells therefrom or to destroy tumorous tissue or cells therein.

Viewed from a yet still further aspect the invention provides a method of imaging of the human or animal (e.g., mammalian, avian or reptilian) body, preferably an animate body, which comprises administering to said body a light imaging contrast agent and generating by a light imaging modality an image of at least a part of said body to which said agent distributes, the improvement comprising using as said contrast agent a physiologically tolerable water-soluble light-imaging contrast agent compound having a molecular weight in the range 500 to 500000 and containing at least two chromophores having delocalized electron systems as well as at least one polyalkylene oxide moiety having a molecular weight in the range 60 to 100000, preferably 200 to 100000, more preferably 250 to 50000, especially preferably 250 to 25000 and more especially preferably 400 to 15000, and preferably using as said modality a confocal scanning laser microscopy (CSLM), optical coherence tomography (OCT), photoacoustic, acousto-optical, diffusive wave endoscopic techniques, multiphoton excitation microscopy, visual observation or time-resolved imaging technique. As used herein, "microscopy" is an optical method with a resolution between 1 mm and 0.1 micron.

In particular, the present invention provides a method of imaging the sentinel lymph node using a light-imaging contrast agent as described herein. Imaging the sentinel lymph node is of particular importance since this lymph node is found closest to the tumor site.

Viewed from a yet still further aspect the invention also provides the use of a physiologically tolerable chromophore-containing material as described herein, for the manufacture of a contrast medium for use in a method of treatment or diagnostic imaging of a human or animal (e.g. mammalian, avian or reptilian) body which involves generation by a CSLM or OCT technique an image of a part of said body to which said material distributes.

Viewed from a yet still further aspect the invention provides a pharmaceutical composition comprising a physiologically tolerable light-imaging contrast agent compound having a molecular weight in the range 500 to 500000 and containing at least two chromophores having delocalized electron systems as well as at least one polyalkylene oxide moiety having a molecular weight in the range 60 to 100000, preferably 200 to 100000, more preferably 250 to 50000, especially preferably 250 to 25000 and more especially preferably 400 to 15000, together with at least one physiologically acceptable carrier or excipient, e.g. in a sterile, pyrogen free aqueous carrier medium.

In one embodiment, a preferred physiologically tolerable contrast agent of this invention comprises at least one chromophoric group attached to a surfactant molecule.

In this invention, a surfactant molecule is defined as an emulsifier or detergent as listed in McCutcheon's Directories, Volume 1: Emulsifiers and Detergents (1994), and which contains at least one chemical functional group selected from the group consisting of an alcohol (OH), a nitrilo group including a primary amine ($NH_2$) and a secondary amine (NH), a carboxylic acid (COOH), a sulfhydryl (SH), a phosphoric acid group, phosphonic acid group, a phenolic group, a sulfonic acid group, a carbon-carbon double bond, and a ketone.

Chemical functional groups in the surfactant molecules can be interconverted by chemical reactions well known to those skilled in the art. For example, a hydroxyl group can be converted to a methanesulfonic acid ester which can be treated with sodium azide and reduced to form an amine group. Carboxylic acid groups and ketones can be reduced to form alcohols, and alcohols can be oxidized to form ketones, aldehydes, and carboxylic acid groups.

Useful surfactant molecules are emulsifiers or detergents which can function as dispersing agents, wetting agents, adsorbents, anticaking agents, soil antiredispositioning agents, antistats, binders, carriers, pearlescents, conditioning agents, hydrotropes, defoamers, emollients, flocculants, humectants, lubricants, opacifiers, plasticizers, preservatives, release agents, scale inhibitors, stabilizers, suspending agents, thickeners, UV absorbers, water repellants, waxes, and polishes, and which contain at least one chemical functional group selected from the group consisting of an alcohol (OH), a nitrilo group including a primary amine ($NH_2$) and a secondary amine (NH), a carboxylic acid (COOH), a sulfhydryl (SH), a phosphoric acid group, a phosphonic acid group, a phenolic group, a sulfonic acid group, a carbon-carbon double bond, and a ketone.

Preferably, the surfactant molecule comprises a polyalkyleneoxide moiety, optionally containing a branching group as defined herein; more preferably a polyalkyleneoxide block copolymeric moiety, optionally containing a branching group as defined herein; and most preferably a polyalkyleneoxide block copolymeric moiety optionally containing a branching group as defined herein and comprising a polypropylene oxide block and a polyethyleneoxide block. Examples of useful surfactant molecules include block copolymers such as AL 2070 available from ICI Surfactants, Antarox block copolymers available from Rhone-Poulenc, Delonic block copolymers available from DeForest, Inc., Hartopol block copolymers available from Texaco Chemical Canada, Macol block copolymers available from PPG Industries, Marlox block copolymers available from Huls America, Pluronic block copolymers including Pluronic F, L, P and R available from BASF Corp., Poly-Tergent block copolymers available from Olin Corp., and Tetronic and Tetronic R block copolymers available from BASF Corp. Currently preferred surfactant molecules include Tetronic and Pluronic block copolymers, and currently most preferred are Tetronic block copolymers.

Chromophoric groups can be attached to surfactant molecules by means of linking groups as defined herein. In one aspect, a chromophoric group can be chemically bound to a surfactant group by means of reaction with a chemical functional group on the surfactant molecule using chemical modifications well known to one skilled in the art. Examples of such reactions include formation of ester linking groups by reaction with an alcohol or phenolic OH group on a surfactant molecule with a chromophoric group containing an acid chloride such as a carboxylic or sulfonic or phosphoric acid chloride or phosphonic acid chloride; formation of amide linking groups by reaction with a primary or secondary amine group on a surfactant molecule with a chromophoric group containing an acid chloride; conversion of a carboxylic acid group or a sulfonic acid group to a reactive intermediate such as an acid chloride or an active ester followed by reaction with a chromophoric group containing an amine or alcohol group.

Preferred contrast agents can be prepared from Pluronic and Tetronic block copolymer surfactant molecules by first converting the hydroxyl functional groups to amine groups and then reacting the amine-containing surfactant molecules with chromophoric groups, for example, with chromophoric groups containing isothiocyanate groups, isocyanate groups, and acid chloride groups.

When a surfactant molecule contains more than one chemical functional group, chromophores can be attached to all or to less than all of the chemical functional groups.

Attachment of chromophores can occur at the ends of the polymer backbone, at the ends of the branching groups, or both. The chromophoric groups can be the same or different. Preferably the chromophoric groups are the same.

In cases where either the surfactant molecule or the attached chromophore are ionically charged, a counterion may be associated to provide charge neutrality. Meglumine is particularly useful for incorporation as a counterion, although other counterions of appropriate charge might also be employed.

Examples of preferred contrast agents include the following wherein R is a methyl group.

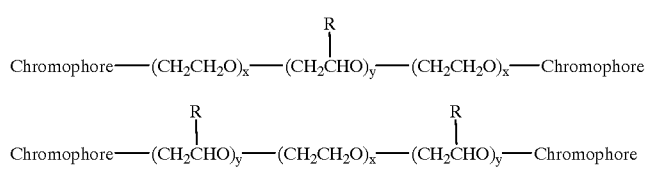

-continued

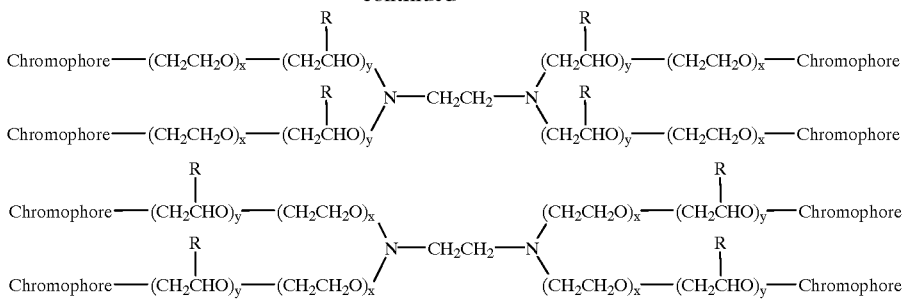

Preferably, the surfactant molecule T-908 (BASF Corporation) can be modified by converting the terminal OH groups to provide an amine group on each branch of the block copolymeric T-908. The modified polymer can then been reacted with an amine-reactive chromophore such as a fluorescein isothiocyanate.

While the product preferably contains four chromophoric groups, it can contain less than four chromophoric groups such as three or two or one. The branches that do not contain a chromophoric group can be terminated by amine groups or by hydroxyl groups. In this example the ratio of x:y is approximately 1:4 and the average molecular weight is approximately 26,000.

ranges of ligands and metals which are also preferred in the present invention. In addition, the metal ions of the current invention can include radionuclides. Also note that in the current invention, the degree of metal chelation can range from zero percent to one hundred percent of the theoretical maximum amount of metal ion which can be chelated by the chelator.

While chromophores can be attached directly to such polymeric ligands and complexes, modification of the polymer synthesis by increasing the proportion of the bis-amine monomer in the polymerization step can be done to provide closely related polymers which are primarily terminated by amines. These intermediates can then be reacted with chro-

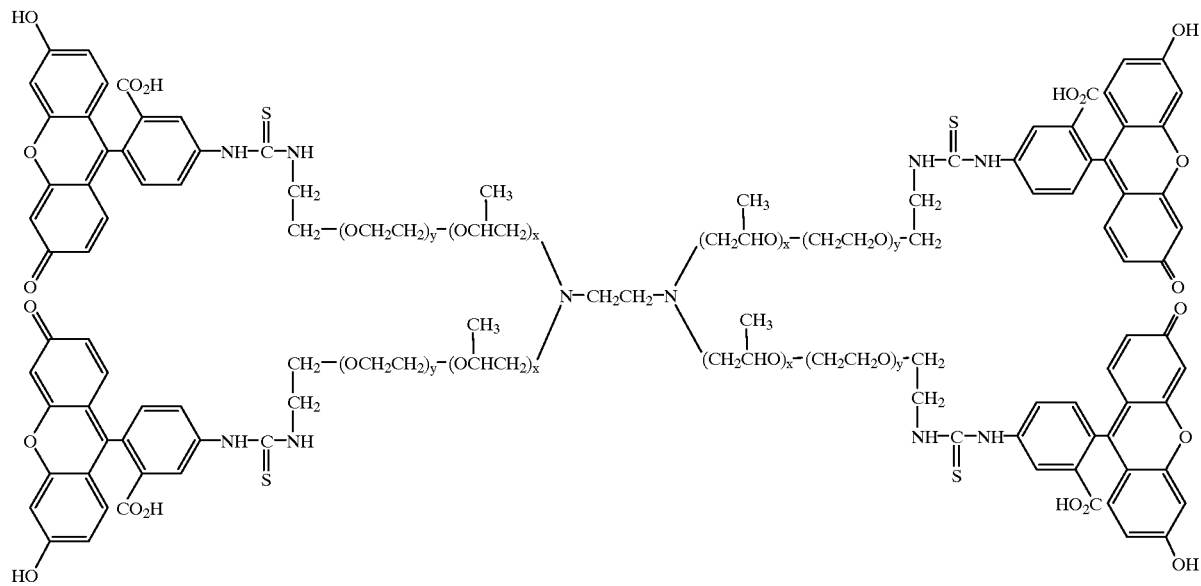

Another class of contrast agents that falls within the scope of this invention includeschromophore bearingpolymeric ligands for metal ions. One useful subset of this class is comprised of polymeric ligands which are particularly effective for complexing lanthanides and other metals used in magnetic resonance imaging. Polymeric ligands and their metal complexes, without chromophores attached, which are particularly useful in this application are described in U.S. patent application Ser. No. 08/478,803, U.S. Pat. No. 5,583, 206, and World Patent Application 96/40274. These and analogous polymers can be structurally modified to incorporate chromophore moieties, either subsequent to their synthesis or in a modification of the synthetic process used to prepare them. Included in those patent references are mophore molecules bearing amine-reactive attachment sites to synthesize polymeric ligands or complexes bearing chromophores.

In polymeric MRI chelatore and complexes which also bear chromophores, the chromophores can be attached to termini of the polymer backbone or its branches. The attachment can also be at sites within the polymer backbone or of its branches. Two or more chromophores are attached to each polymer molecule. The ligand can be uncomplexed or complexed with a metal cation. Depending on the charge of the metal ion and the nature of the ligand there may also be counterions associated with the complex to provide charge neutrality. Counterions may also be associated with the carboxylic acids of the uncomplexed or partially complexed ligand polymer. Meglumine is particularly desirable for incorporation as a counterion, although any of the counterions described in the above patents could also be employed.

An example of such a chromophore-bearing ligand is illustrated below, wherein n is defined as an integer whose value causes the molecular weight of the polymer to fall within the molecular weight range defined in the present invention:

mophores having delocalized electron systems as well as at least one polyalkylene oxide moiety having a molecular weight in the range 60 to 100000, preferably 200 to 100000, more preferably 250 to 50000, especially preferably 250 to 25000 and more especially preferably 400 to 15000.

The chromophores may be the same or different.

The chromophores may be fluorophores or light-absorbing moieties and will preferably be optionally metallated organic chromophores.

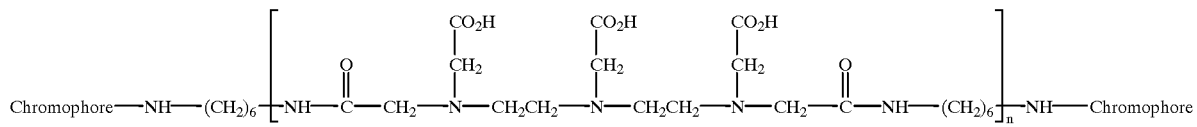

A metal complex of this ligand, which may also be associated with counterions to provide charge neutrality, is illustrated below:

In one embodiment each chromophore can be an infrared absorbing or fluorescent chromophore. Examples include chromophores selected from the group consisting of cyanine

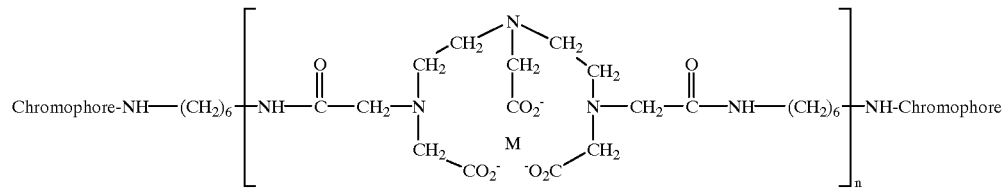

A more specific example of a polymeric ligand in this class and a metal complex of it are illustrated below:

chromophores; pyrilium chromophores; thiapyrilium chromophores; squarylium chromophores; croconium chro-

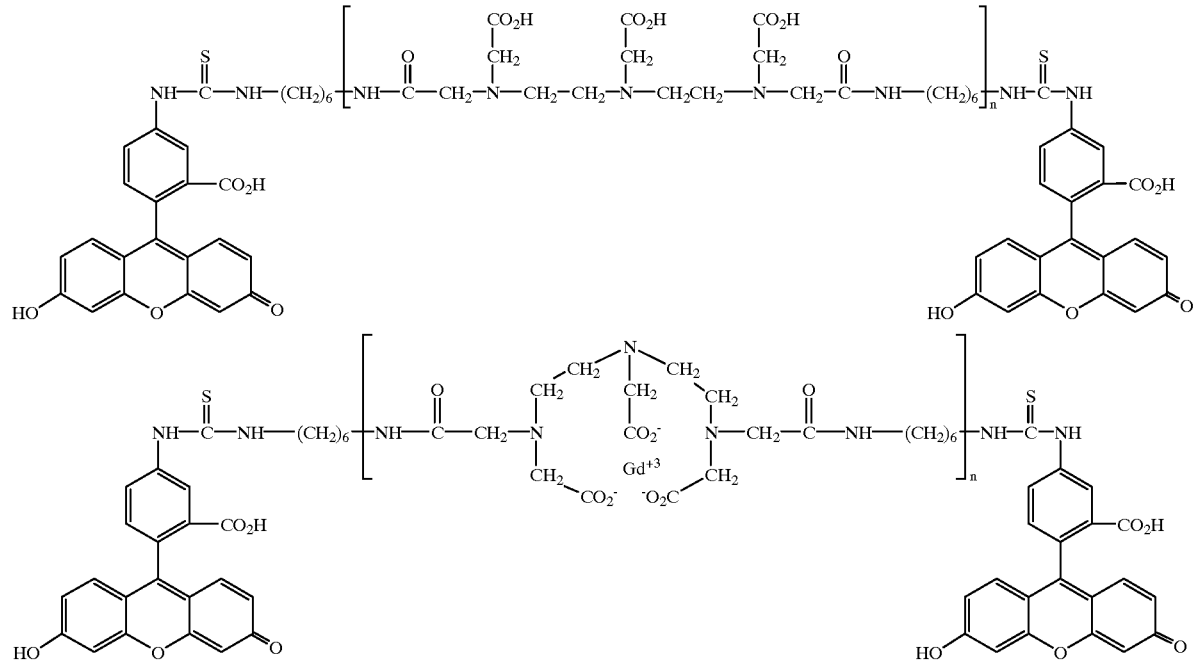

As mentioned above, the contrast agent compounds according to the invention have a molecular weight in the range of 500 to 500000 and contain at least two chromophores; indoaniline chromophores; azo chromophores; anthraquinone chromophores; naphthoquinone chromophores; metalated azo chromophores such as azo chromophores containing nickel, cobalt, copper, iron, and manganese; metal phthalocyanines such as phthalocyanines containing aluminum, silicon, nickel, zinc, lead, cadmium, magnesium, vanadium, cobalt, copper, and iron; metal naphthalocyanines such as naphthalocyanines containing aluminum, zinc, cobalt, magnesium, cadmium, silicon, nickel, vanadium, lead, copper, and iron; bis(dithiolene) metal complexes $I^a$ comprising a metal ion such as nickel, cobalt, copper, and iron coordinated to four sulfur atoms in a ligand complex; bis(dithiolene) metal complexes $II^a$ comprising a metal ion such as nickel, cobalt, copper, and iron coordinated to two sulfur atoms and two oxygen atoms in a ligand complex; α-diimine-dithiolene complexes comprising a metal ion such as nickel, cobalt, copper, and iron coordinated to two sulfur atoms and two nitrogen atoms in a ligand complex; and tris(α-diimine) complexes comprising a metal ion coordinated to six nitrogen atoms in a ligand complex. Examples of these chromophores can be found in Topics in Applied Chemistry, Infrared Absorbing Chromophores, edited by M. Matsuoka, Plenum Press, New York, N.Y., 1990.

Preferred chromophore-containing compounds contain reactive functional groups or groups that can be converted to reactive functional groups. Examples of reactive functional groups include isothiocyanates; isocyanates; carboxylic acid halides such as carboxylic acid chlorides; halomethylcarbonyl groups such as iodomethylcarbonyl groups; sulfonic acid halides such as sulfonyl chlorides; sulfhydryl groups; sulfonate esters of alcohols such as methanesulfonates and toluenesulfonates; activated carboxylic acid esters such as p-nitrophenyl esters, N-hydroxysuccinimide esters, and pentafluorophenyl esters; and other well known reactive functional groups such as those listed in S. S. Wong, Chemistry of Protein Conjugation and Crosslinking, CRC Press, 1991. Examples of groups that can be converted to reactive functional groups include chloromethyl groups which can be converted into thioethers and carboxylic acid groups which can be converted into activated esters with dehydrating carbodiimide reagents in the presence of an appropriate alcohol such as, for example, p-nitrophenol, N-hydroxysuccinimide, and pentafluorophenol or which can be treated with thionyl chloride to provide carboxylic acid chlorides; nitrile groups which can be hydrolysed with aqueous acid or base and converted into carboxylic acid groups and utilised as above; amine groups such as, for example, —$NH_2$ and —NHR, which can react to form amides with carboxylic acid halides and activated esters or converted with thiophosgene into isothiocyanate groups from —$NH_2$ or into chlorothiocarbonylamide groups from —NHR, or treated with iodoacetyl iodide to form alpha-iodomethylcarbonylamines which will react with sulfhydryl groups; nitro groups which can be reduced to form amine —$NH_2$ groups and further converted as above; alcohol OH groups which can be converted into sulfonate ester groups; halogen groups such as iodine and bromine attached to carbon atoms in aromatic groups which halogen groups can be treated with sodium dicyanocuprate in DMF to provide nitrile groups which can be used as above. In addition, many chromophores comprise aromatic rings which can be functionalized in many well known ways. For example, aromatic rings can be nitrated with nitric acid and sulfuric acid to provide nitro groups which can be reduced to amine groups and converted into halogen groups, nitrile groups, and carboxylic acid groups. Aromatic rings can also be sulfonated with sulfuric acid to introduce sulfonic acid groups and the sulfonic acid groups can be converted into sulfonyl chloride groups with thionyl chloride or phosphorus pentachloride.

Functional groups on linking groups can be made to react with chromophore functional groups in well known fashions, many of which are listed in S. S. Wong, Chemistry of Protein Conjugation and Crosslinking, CRC Press, 1991. For example, a linking group containing one or more than one carboxylic acid group, such as, for example, succinic acid, polyacrylic acid, phthalic acid, tartaric acid, chelating groups such as DTPA, nitrogen-blocked amino acids (such as those described in M. Bodanszky, Principles of Peptide Synthesis, Springer-Verlag N.Y. 1984) and PEG-dicarboxylic acid can be treated with a chromophore containing a primary amine group in the presence of a carbodiimide such as, for example, dicyclohexylcarbodiimide to form an amide bond between the chromophore and the linking group. Chromophores which contain isothiocyanate groups or active ester groups or acid halide groups or sulfonyl chloride groups can react with linking groups which contain one or more than one amines such as, for example, polyethyleneamine, PEG diamine, Tetronic tetramine, Pluronic diamine, lysine, 1,4-butanediamine, melamine, ethylenediamine, polylysine, aminocaproic acid, carboxylic acid-blocked amino acids (such as those described in M. Bodanszky, Principles of Peptide Synthesis, Springer-Verlag, N.Y. 1984) to form bonds between the chromophore and the linking group such as thiourea bonds and amide bonds between the chromophore and the linking group.

In another embodiment at least one chromophore is an infrared absorbing chromophore which can be a fluorescent chromophore or fluorescent chromophore and at least one chromophore is a visible chromophore which can be a fluorescent chromophore. Examples of such chromophores include fluorescein derivatives, rhodamine derivatives, coumarins, azo chromophores, metalizable chromophores, anthraquinone chromophores, benzodifuranone chromophores, polycyclic aromatic carbonyl chromophores, indigoid chromophores, polymethine chromophores, azacarbocyanine chromophores, hemicyanine chromophores, barbiturates, diazahemicyanine chromophores, styryl chromophores, diaryl carbonium chromophores, triaryl carbonium chromophores, cyanine chromophores, naphthalocyanine chromophores, merocyanine chromophores, phthalocyanine chromophores, quinophthalone chromophores, triphenodioxazine chromophores, formazan chromophores, phenothiazine chromophores such as methylene blue, azure A, azure B, and azure C, oxazine chromophores, thiazine chromophores, naphtholactam chromophores, diazahemicyanine chromophores, azopyridone chromophores, azobenzene chromophores, mordant chromophores, acid chromophores, basic chromophores, metallized and premetallized chromophores, xanthene chromophores, direct chromophores, leuco chromophores which can be oxidized to produce chromophores with hues bathochromically shifted from those of the precursor leuco chromophores, and other chromophores such as those listed by Waring, D. R. and Hallas, G., in "The Chemistry and Application of Dyes", Topics in Applied Chemistry, Plenum Press, New York, N.Y., 1990. Additional chromophores can be found listed in Haugland, R. P., "Handbook of Fluorescent Probes and Research Chemicals", Sixth Edition, Molecular Probes, Inc., Eugene Oreg., 1996.

Preferred are chromophores having an absorption or emission maximum in the visible wavelength range 300 to 700 nm, especially 400 to 600 nm.

Preferred are chromophores having an absorption or emission maximum in the wavelength range 300–1300 nm, especially 600–1300 nm, more especially 600 to 1200 nm, and most especially 650 to 1000 nm.

In another embodiment, the polymer of this invention can comprise a fluorescent metal ion. The fluorescent metal ion can be selected from, but is not limited to, metals of atomic number 57 to 71. Ions of the following metals are preferred: La, Ce, Pr, Nd, Pm, Sm, Eu, Gd, Tb, Dy, Ho, Er, Tm, Yb, and Lu. Eu is especially preferred.

In another embodiment, the polymer of this invention can comprise the ion of one or more paramagnetic elements which are suitable for the use in magnetic resonance imaging (MRI) applications. The paramagnetic element can be selected from elements of atomic number 21 to 29, 43, 44 and 57 to 71. The following elements are preferred: Cr, V, Mn, Fe, Co, Ni, Cu, La, Ce, Pr, Nd, Pm, Sm, Eu, Gd, Tb, Dy, Ho, Er, Tm, Yb and Lu. Ions of Mn, Gd, and Dy are especially preferred.

In another embodiment of this invention, a polymer of this invention comprising at least two metal ions in combination with one another in the same formulation, prepared as described herein, is specifically contemplated. For example, the use of a therapeutically effective dose of a radionuclide such as $^{90}Y^{+3}$ together with a diagnostic imaging effective dose of a paramagnetic ion such as $Gd^{+3}$, the ratio of the molar concentration of the diagnostic imaging effective ion to the molar concentration of the radionuclide ion being typically greater than one, in a pharmaceutically effective formulation of said polymer permits the simultaneous magnetic resonance imaging of at least a portion of the tissue of a host patient during therapeutic treatment of said patient.

In another embodiment of this invention, the use of radioisotopes of iodine is specifically contemplated. For example, if the polymer comprises a substituent that can be chemically substituted by iodine in a covalent bond forming reaction, such as, for example, a substituent containing hydroxyphenyl functionality, such a substituent can be labeled by methods well known in the art with a radioisotope of iodine. The thus covalently linked radioactive iodine species can be used in therapeutic and diagnostic imaging applications as described herein. A preferred polymer comprises a linking group, an infrared chromophore, a tyrosine site covalently attached to an isotope of iodine, and a chelating agent which is chelated to $^{90}Y^{+3}$ ion.

As mentioned above, the contrast agent compounds according to the invention can consist of oligomeric Chr-(PAO-Chr)$_n$ compounds formed by the oligomerization of difunctional chromophore materials and difunctional PAO materials.

Examples of difunctional chromophores include:

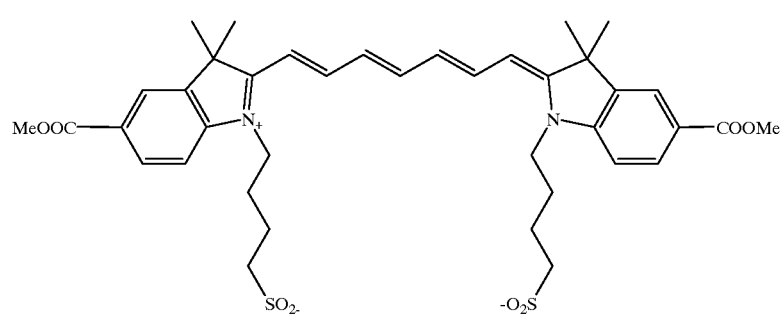

a)

where the oligomer is formed, for example, by transesterification under acid catalysis with HO-PEG-OH or by amide formation, for example, by amidation of the ester group with amino groups in H$_2$N-PEG-NH$_2$, and HO-PEG-NH$_2$.

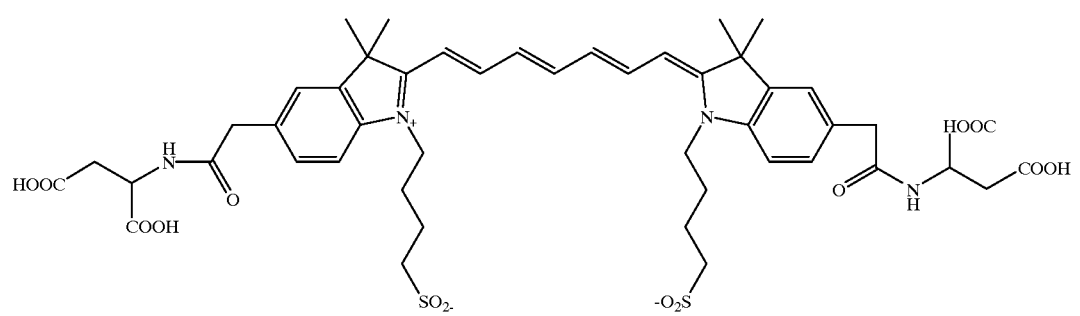

b)

where the oligomer is formed, for example, by esterification of carboxylic acids under acid catalysis with HO-PEG-OH or by amide formation, for example, by amidation of activated N-hydroxysuccinimide ester groups with amino groups in H$_2$N-PEG-NH$_2$, and HO-PEG-NH$_2$.

c)

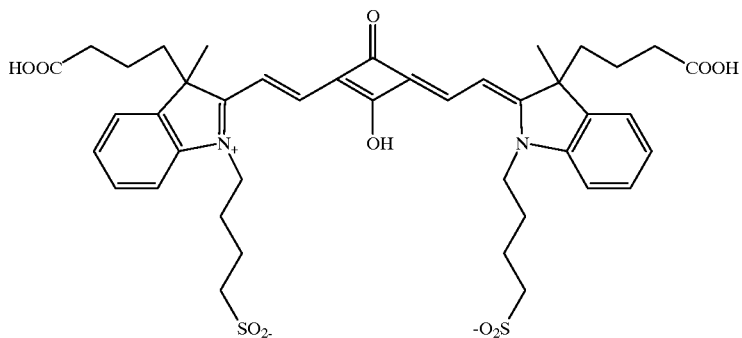

and

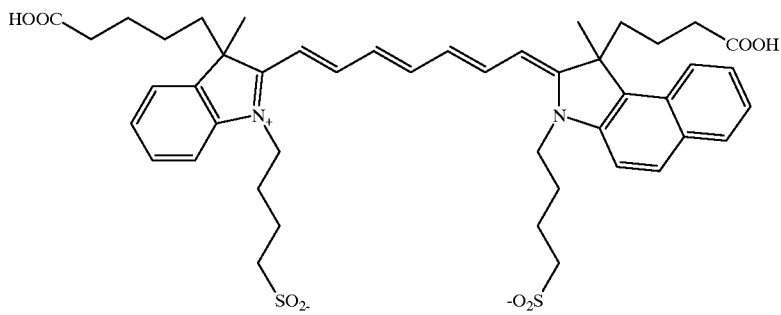

and

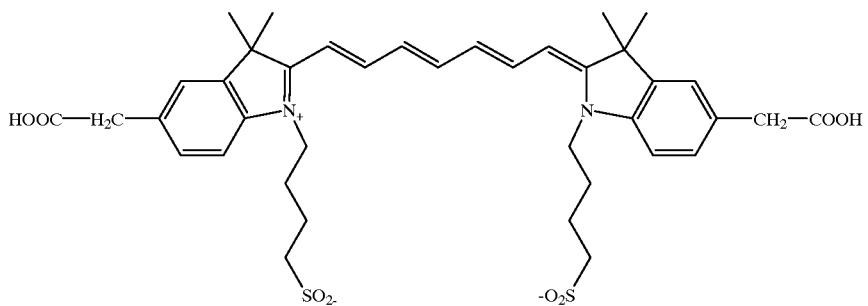

where the oligomer is formed, for example, by esterification of carboxylic acids under acid catalysis with HO-PEG-OH or by amide formation, for example, by amidation of activated N-hydroxysuccinimide ester groups with amino groups in $H_2N$-PEG-$NH_2$, and HO-PEG-$NH_2$.

where the oligomer is formed, for example, by dehydration of the vicinal diol under acidic dehydration conditions followed by etherification of epoxide formed with HO-PEGd)

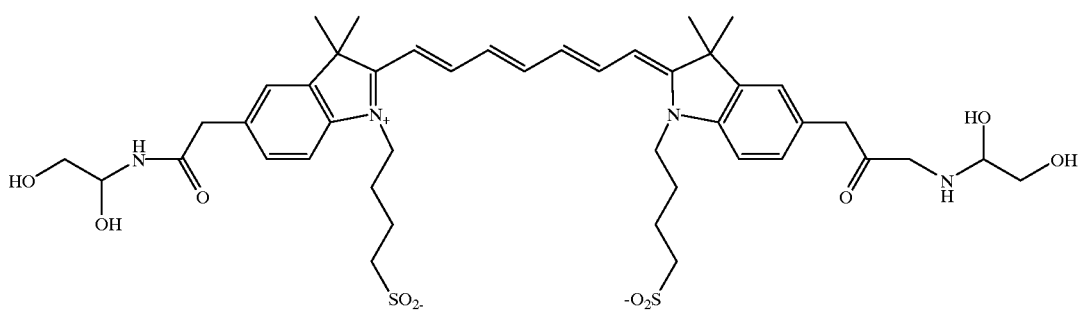

OH or by amine formation, for example, of the epoxide groups with amino groups in $H_2N$-PEG-$NH_2$, and HO-PEG-$NH_2$.

In another embodiment, the chromophore, PAO or linking group can be attached to a targeting vector. This vector targets cells or receptors on cells. Preferably, the targeting vector or ligand targets cells selected from the group consisting of myocardial cells, endothelial cells, epithelial cells, tumor cells and the glycoprotein GPIIb/IIIa receptor. Also in preferred embodiments, the targeting vector or ligand is a targeting vector selected from the group consisting of proteins, peptides, saccharides, steroids, steroid analogs, bioactive agents and genetic material, with proteins, peptides and saccharides being more preferred. Also preferred are targeting vectors which target regions of arteriosclerosis, especially atherosclerotic plaque.

In the case of targeting vectors which comprise saccharide groups, suitable saccharide moieties include, for example, monosaccharides, disaccharides and polysaccharides. Exemplary monosaccharides may have six carbon atoms and these saccharides include allose, altrose, glucose, mannose, gulose, idose, galactose, talose, fructose, psicose, comatose and tagatose. Five carbon moieties include ribose, arabinose, xylose, lyxose, ribulose and xylulose. Four carbon saccharides include erythrose, threose and erythrulose. Disaccharides include sucrose, lactose, maltose, isomaltose and cellobiose.

Preferred vectors are those which target the myocardium and those which target cancer cells.

In another embodiment, this invention provides a targeting immunoreagent comprising a polymer of this invention and optionally a metal ion and a chelating agent in a linking group. The immunoreactive group can be attached through a linking group to the polymer.

Compositions and formulations comprising a mixture of polymers of this invention in bulk use rather than as individual molecules can contain a wide range of ratios of metal ion to chelating agent. In preferred formulation embodiments, the mole ratio of metal ion to chelating agent in a linking group is from about 1:1000 to about 1:1. In some formulation embodiments, the ratio of the chelating agent to the immunoreactive group can vary widely from about 0.5:1 to 10:1 or more. In some formulation embodiments, the mole ratio of chelating agent to immunoreactive groups is from about 1:1 to about 6:1.

In another embodiment, this invention provides a polymeric targeting radioactive immunoreagent comprising a metal radionuclide ion, a chelating agent in a linking group of the polymer, and an immunoreactive group which is attached through a linking group to said polymer. The radionuclide ion can be selected, for example, from Sc, Fe, Pb, Ga, Y, Bi, Mn, Cu, Cr, Zn, Ge, Mo, Tc, Ru, In, Sn, Re, Sr, Sm, Lu, Eu, Dy, Sb, W, Po, Ta and Tl ions. Preferred radionuclides include $^{44}Sc^{+++}$, $^{64}Cu^{++}$, $^{67}Cu^{++}$, $^{111}In^{+++}$, $^{212}Pb^{++}$, $^{68}Ga^{++}$, $^{90}Y^{+++}$, $^{177}Lu^{+++}$, $^{186}Re^{++}$, $^{188}Re^{++}$, $^{99m}Tc^{++}$, $^{87}Y^{+++}$, and $^{212}Bi^{+++}$ ions. Of these, the most preferred are $^{90}Y^{+++}$ ions.

The metal radionuclide ion and the chelating agent in a linking group of the polymer of the targeting immunoreagent are easily complexed by merely mixing an aqueous solution of the immunoreagent containing the chelating agent in a linking group of the polymer with a metal radionuclide salt in an aqueous solution preferably having a pH of 4 to 11 as described above. The salt is preferably any water soluble salt of the metal such as a halide or nitrate salt. The targeting immunoreagent containing the chelating agent in a linking group of the polymer of this invention and the metal ion is generated in aqueous solution at a pH of between about 5 and about 10 and preferably from about 6 to about 9. The targeting immunoreagent containing the chelating agent in a linking group of the polymer of this invention and the metal ion is generated optionally in the presence of buffers, such as acetate, citrate, phosphate and borate, to produce a desired optimum pH. Preferably, the buffer salts are selected so as not to interfere with the initial and subsequent binding of the metal ion to the chelating agent.

The targeting immunoreagent of this invention comprising a radioisotope of a metal ion such as $^{90}Y^{+3}$ (as a non-limiting example) can be used for the therapeutic treatment of tumors, particularly if the immunoreagent is a tumor antigen specific antibody or a fragment of such an antibody. In therapeutic applications, the targeting immunoreagent of this invention preferably contains a ratio of metal radionuclide ion to chelating agent that is effective in such therapeutic applications. In preferred formulation embodiments, the mole ratio of metal ion per chelating agent is from about 1:100 to about 1:1.

The polymeric targeting immunoreagent of this invention comprising a radioisotope of a metal ion such as $^{111}In^{+3}$ or $^{87}Y^{+3}$ (as non-limiting examples) can be used for the diagnostic imaging of tumors in cancer patients. In diagnostic imaging applications, the polymeric targeting immunoreagent of this invention preferably contains a ratio of metal radionuclide ion to chelating agent in a linking group of the polymer that is effective in such diagnostic imaging applications. In preferred formulation embodiments, the mole ratio of metal ion per chelating agent is from about 1:10,000 to about 1:1.

In another embodiment, this invention provides a polymeric targeting paramagnetic immunoreagent comprising a paramagnetic metal ion as described above, a chelating agent in a linking group of the polymer of this invention as described above, and an immunoreactive group as described above attached through a linking group. Such targeting paramagnetic immunoreagents are useful in both in vitro and in vivo magnetic resonance imaging of tissue that is targeted by an immunoreagent (for example, tumor tissue in a mammal such as man, which tissue contains an abundance of tumor associated antigen to which an immunoreagent such as an antibody will bind).

In another embodiment, this invention provides a polymeric targeting fluorescent immunoreagent comprising a fluorescent metal ion as described above, a chelating agent in a linking group of the polymer of this invention, and an immunoreactive group as described above attached through a linking group. Such targeting fluorescent immunoreagents are useful in the in vitro detection of antigens which bind to the immunoreagent. Such antigens may be found in human tissue or fluids, and the detection of such antigens comprises a useful in vitro assay employing the dye polymers of this invention. Time delayed fluorescence assays and the sorting and separation of cells employing time delayed fluorescence detection techniques (such as in the separation of hybridoma cells which contain antigen on their surface, to which antigen the targeting immunoreagent of this invention binds, from cells which do not contain such antigen on their surface) comprise additional uses of the dye polymers of this invention and of the targeting fluorescent immunoreagents of this invention.

In another embodiment, the components of this invention comprise a targeting vector, V, attached to the PAO, chromophore or linker or to two or more thereof, e.g. via a bond or a further linking group, L*, where L* is the residue of a linking agent.

The term "residue" is used herein in context with a chemical entity. Said chemical entity comprises, for example, a vector, or a chromophore, or a PAO, or a linking group, etc. The vector may be for example a receptor recognizing group, or an immunoreactive material, or an immunoreactive protein, or an antibody, or an antibody fragment, or a protein, or a peptide, or a small organic molecule. The term "residue" is defined as that portion of said chemical entity which exclusively remains when one or more chemical bonds of which said chemical entity is otherwise comprised when considered as an independent chemical entity, are altered, modified, or replaced to comprise one or more covalent bonds to one or more other chemical entities. Thus, for example, in one embodiment the residue of a chromophore is comprised of a chromophore which is at least monovalently modified through attachment to the residue of another chemical entity such as, for example, to the residue of a linking group.

As used herein, the terms "receptor" and "antigen" refer to a chemical group in a molecule which comprises an active site in said molecule, or to an array of chemical groups in a molecule which comprise one or more active sites in said molecule, or to a molecule comprised of one or more chemical groups or one or more arrays of chemical groups, which group or groups or array of groups comprise one or more active sites in said molecule. An "active site" of a receptor has a specific capacity to bind to or has an affinity for binding to a vector. With respect to use with the term "receptor" or with the term "active site in a receptor", the term "vector" or "ligand" as used herein refers to a molecule comprised of a specific chemical group or a specific array of chemical groups (receptor recognizing group) which molecule, group, or array of groups is complementary to or has a specific affinity for binding to a receptor, especially to an active site in a receptor. Examples include cell surface antigens, cell surface and intracellular receptors which bind hormones; and cell surface and intracellular receptors which bind drugs. The sites of specific association or specific binding of hormones to said cellular receptors; and of specific binding of drugs to cellular receptors are examples of active sites of said receptors, and the hormones or drugs, agonists, and antagonists which bind to receptors are examples of vectors for the respective receptors.

The vector group, V, can be selected from a wide variety of naturally occurring or synthetically prepared materials, including, but not limited to enzymes, amino acids, peptides, polypeptides, proteins, lipoproteins, glycoproteins, lipids, phospholipids, hormones, growth factors, steroids, vitamins, polysaccharides, lectins, toxins, nucleic acids (including sense and antisense oligonucleotides, peptide nucleic acids), haptens, avidin and derivatives thereof, biotin and derivatives thereof, antibodies (monoclonal and polyclonal), anti-antibodies, antibody fragments and antigenic materials (including proteins and carbohydrates). The vector group, V, can be also be selected from, but not limited to, components or products of viruses, bacteria, protozoa, fungi, parasites, rickettsia, molds, as well as animal and human blood, tissue and organ components. Furthermore, the vector group, V, can be a pharmaceutical drug or synthetic analog of any of the materials mentioned above as well as others known to one skilled in the art. Additional specific vector groups are described in WO 96/40285 which patent is incorporated herein in its entirety.

In one embodiment, V is preferably an antibody, antibody fragment, protein or peptide which recognizes and is specific for a tumor associated antigen or receptor. In some embodiments, V can contain a receptor recognizing group covalently bonded thereto through a chemical bond or a linking group derived from the residue of a receptor recognizing group and the residue of a reactive group on V. As used herein, the term "receptor recognizing group" which can be abbreviated to "RRG" also includes an organic compound which is capable of covalently bonding the vector and which is found in a living organism or is useful in the diagnosis, treatment or genetic engineering of cellular material or living organisms, and which has a capacity for interaction with another component ("active site" of a receptor) which may be found in biological fluids or associated with cells to be treated or subjected to diagnosis such as cells in a tumor.

The RRG can be selected from the same wide variety of naturally occurring or synthetically prepared materials mentioned above. In addition, an RRG can be any substance which when presented to an immunocompetent host will result in the production of a specific antibody capable of binding with that substance, or the antibody so produced, which participates in an antigen-antibody reaction.

In one embodiment, preferred vectors are antibodies and various immunoreactive fragments thereof, proteins and peptides as long as they contain at least one reactive site for reaction with a vector reactive group or with a linking group (L) as described herein. That site can be inherent to the vector or it can be introduced through appropriate chemical modification of the vector. In addition to antibodies and fragments produced by the techniques outlined herein, other antibodies, proteins, and peptides produced by the techniques of molecular biology, phage display, and genetic engineering are specifically included.

As used herein, the term "antibody fragment" refers to a vector which comprises a residue of an antibody, which antibody characteristically exhibits an affinity for binding to an antigen. The term "affinity for binding to an antigen", as used herein, refers to the thermodynamic expression of the strength of interaction or binding between an antibody combining site and an antigenic determinant and, thus, of the stereochemical compatibility between them; as such, it is the expression of the equilibrium or association constant for the antibody-antigen interaction. The term "affinity", as used herein, also refers to the thermodynamic expression of the strength of interaction or binding between a vector and a receptor and, thus, of the stereochemical compatibility between them; as such, it is the expression of the equilibrium or association constant for the vector/receptor interaction.

Antibody fragments exhibit at least a percentage of said affinity for binding to said antigen, said percentage being in the range of 0.001 percent to 1,000 percent, preferably 0.01 percent to 1,000 percent, more preferably 0.1 percent to 1,000 percent, and most preferably 1.0 percent to 1,000 percent, of the relative affinity of said antibody for binding to said antigen.

An antibody fragment can be produced from an antibody by a chemical reaction comprising one or more chemical bond cleaving reactions; by a chemical reaction comprising one or more chemical bond forming reactions employing as reactants one or more chemical components selected from a group comprised of amino acids, peptides, carbohydrates, linking groups as defined herein, spacing groups as defined herein, vector reactive groups as defined herein, and antibody fragments such as are produced as described herein and by a molecular biological process, a bacterial process, or by a process comprised of and resulting from the genetic engineering of antibody genes.

An antibody fragment can be derived from an antibody by a chemical reaction comprised of one or more of the following reactions:

(a) cleavage of one or more chemical bonds of which an antibody is comprised, said bonds being selected from, for example, carbon-nitrogen bonds, sulfur-sulfur bonds, carbon-carbon bonds, carbon-sulfur bonds, and carbon-oxygen bonds, and wherein the method of said cleavage is selected from:
   (i) a catalyzed chemical reaction comprising the actions of a biochemical catalyst such as an enzyme such as papain or pepsin which to those skilled in the art are known to produce antibody fragments commonly referred to as Fab and Fab'2, respectively;
   (ii) a catalyzed chemical reaction comprising the action of an electrophilic chemical catalyst such as a hydronium ion which, for example, favourably occurs at a pH equal to or less than 7;
   (iii) a catalyzed chemical reaction comprising the action of a nucleophilic catalyst such as a hydroxide ion which, for example, favourably occurs at a pH equal to or greater than 7;
   (iv) a chemical reaction comprised of a substitution reaction employing a reagent which is consumed in a stoichiometric manner such as substitution reaction at a sulfur atom of a disulfide bond by a reagent comprised of a sulfhydryl group;
   (v) a chemical reaction comprised of a reduction reaction such as the reduction of a disulfide bond; and
   (vi) a chemical reaction comprised of an oxidation reaction such as the oxidation of a carbon-oxygen bond of a hydroxyl group or the oxidation of a carbon-carbon bond of a vicinal diol group such as occurs in a carbohydrate moiety; or
(b) formation of one or more chemical bonds between one or more reactants, such as formation of one or more covalent bonds selected from, for example, carbon-nitrogen bonds (such as, for example, amide bonds, amine bonds, hydrazone bonds, and thiourea bonds), sulfur-sulfur bonds such as disulfide bonds, carbon-carbon bonds, carbon-sulfur bonds, and carbon-oxygen bonds, and employing as reactants in said chemical bond formation one or more reagents comprised of amino acids, peptides, carbohydrates, linking groups as defined herein, spacing groups as defined herein, vector reactive groups as defined herein, and antibody fragments such as are produced as described in (a), above; or
(c) an antibody fragment can be derived by formation of one or more non-covalent bonds between one or more reactants. Such non-covalent bonds are comprised of hydrophobic interactions such as occur in an aqueous medium between chemical species that are independently comprised of mutually accessible regions of low polarity such as regions comprised of aliphatic and carbocyclic groups, and of hydrogen bond interactions such as occur in the binding of an oligonucleotide with a complementary oligonucleotide; or
(d) an antibody fragment can be produced as a result of the methods of molecular biology or by genetic engineering of antibody genes, for example, in the genetic engineering of a single chain immunoreactive group, a Fv fragment or a minimal recognition unit.

An antibody fragment can be produced as a result a combination of one or more of the above methods.

If desired, a vector can be modified or chemically altered to provide reactive groups for attaching to the residues of a receptor moiety or antigen found in or on tissues and cells of interest. Such techniques include the use of linking moieties and chemical modification such as described in WO-A-89/02931 and WO-A-89/2932, which are directed to modification of oligonucleotides, and U.S. Pat. No. 4,719,182.

Two highly preferred uses for the compounds of this invention are for the diagnostic imaging of diseased tissue such as tumors and for the therapeutic treatment of diseased tissue such as tumor tissue. Preferred vectors therefore include antibodies (sometimes hereinafter referred to as Ab) to tumor-associated antigens. Specific non-limiting examples include B72.3 and related antibodies (described in U.S. Pat. Nos. 4,522,918 and 4,612,282) which recognize colorectal tumors; 9.2.27 and related anti-melanoma antibodies; D612 and related antibodies which recognize colorectal tumors; UJ13A and related antibodies which recognize small cell lung carcinomas; NRLU-10, NRCO-02 and related antibodies which recognize small cell lung carcinomas and colorectal tumors (Pan-carcinoma); 7E11C5 and related antibodies which recognize prostate tumors; CC49 and related antibodies which recognize colorectal tumors; TNT and related antibodies which recognize necrotic tissue; PR1A3 and related antibodies which recognize colon carcinoma; ING-1 and related antibodies, which are described in WO-A-90/02569; B174, C174 and related antibodies which recognize squamous cell carcinomas; B43 and related antibodies which are reactive with certain lymphomas and leukemias; and anti-HLB and related monoclonal antibodies; and other tumor, tissue or cell-specific antibodies known to those skilled in the art.

More preferred vectors are proteins, especially recombinant human proteins, such as are produced or modified by molecular biological, phage display or genetic engineering techniques, which modifications comprise the independent incorporation, substitution, insertion, and deletion of specific amino acids in a peptide sequence of said protein to produce recombinant human proteins containing an RRG which has an affinity for binding to an active site of a receptor. A thus-modified recombinant protein vector has an affinity for an active site of a receptor which is greater than the affinity of the natural, unmodified, vector for the active site of the receptor In another embodiment, the vector comprises a fusion protein. As used herein, the term "fusion protein" refers to a genetically engineered material comprised of a protein whose coding region is comprised of the coding region of a residue of a first protein fused, in frame, to the coding region of a residue of a second protein. Preferably, said fusion protein is comprised of a protein whose coding region is comprised of the coding region of a residue of an RRG fused, in frame, to the coding region of one or more residues of a vector or a linker which linker can be a protein or peptide. The above genetically engineered fusion protein comprising the vector can be comprised of a protein whose coding region is independently comprised of the coding region of a residue of a human or of a non-human first protein fused, in frame, to the coding region of a residue of a human or non-human second protein. Preferably, said coding regions are independently human and bacterial or modified by genetic engineering techniques as above.

Even more preferred vectors are peptides, oligopeptides or peptoids, which vectors are composed of one or more than one amino acids whose sequence and composition comprise a molecule, specific chemical group or a specific array of chemical groups, which are complementary to or have a specific affinity for binding to a receptor. Such peptides may be compositionally identical to the amino acids that comprise the RRG of antibodies, antibody fragments, proteins or fusion proteins that recognize the same receptor.

Alternatively, such peptidic vectors may not have an amino acid sequence identical to other RRGs but will be structurally or three-dimensionally equivalent to other RRGs that bind the same receptor. Such equivalent peptides may be identified by molecular biological techniques such as point mutation, phage display, genetic engineering and others techniques known to those skilled in the art. In addition, peptidic or oligopeptidic vectors may be designed de novo using the well-practiced methodologies of computational chemistry and peptide synthesis. Synthetic peptidic vectors are not restricted to linear arrays of amino acids but may also be cyclic and contain more than one RRG per peptide. Peptide or peptoid vectors may be composed of L-amino acids, D-amino acids, non-naturally occurring amino acids, synthetic amino acid substitutes, organic molecules or mixtures of all of these, and bonded to each other by peptide (amide) or non-amide bonds.

Especially preferred vectors are peptidomimetic molecules, which molecules are synthetic organic materials that are the stuctural or functional equivalent of RRGs derived or identified from antibodies, antibody fragments, proteins, fusion proteins, peptides or peptoids, and that have affinity for the same receptor. Other vectors which are considered to be peptidomimetic include chemical entities, such as drugs, for example, which show affinity for the receptor, and especially the active site of the receptor, of interest. Peptidomimetic vectors may be identified through the use of molecular biological techniques such as point mutation, phage display, genetic engineering and others techniques known to those skilled in the art. Peptidomimetic vectors may be designed and synthesized de novo using current chemical methods as well as the techniques of computational chemistry and combinatorial chemistry.

As used herein, "vector reactive group" refers to one or more chemical groups which can react with a reactive functional group typically found on or introduced into a vector, to form a linking group between the chromophore and the vector. It is specifically contemplated that a vector reactive group can be used to conjugate a chromophore of this invention to a non-protein biomolecule as well as to a non-biological molecule such as a synthetic chemical substance, for example, a drug or other molecule that has an affinity for the active site of a receptor that is of interest. Vector reactive groups can also be used for the purposes of detection of such a molecule in a mixture which may contain such a synthetic chemical substance and which substance contains a group that is reactive with the vector reactive group. Thus, the vector reactive groups useful in the practice of this invention include those groups which can react with a molecule, preferably a biological molecule (such as a protein, a carbohydrate, a nucleic acid, and a lipid) containing a reactive group to form a linking group between the chromophore and the molecule. If the molecule is a protein, preferred reactive groups include amine groups and sulfhydryl groups. Especially preferred biological molecules contain a RRG as described above.

The vector reactive groups useful in the practice of this invention also include those groups which can react with a biological molecule that is chemically modified, for example, by oxidation, by reduction, or by covalent bond formation such as by amide bond formation with another chemical species such as, for example, an amine, an amino acid, a substituted amine, or a substituted amino acid, to introduce a reactive group into the biological molecule, to form a linking group between the chromophore and the chemically modified biological molecule.

Preferred vector reactive groups can be selected from, but are not limited to, groups that will react directly with an amine group such as a lysine epsilon amine group or a terminal amine group in a protein or peptide or with a sulfhydryl group such as a cysteine sulfhydryl group commonly found on a protein or other biological molecule. Examples of such protein reactive groups include active halogen-containing groups such as chloromethylphenyl groups, chloromethylcarbonyl groups, and iodomethylcarbonyl groups; activated 2-leaving-group-substituted ethylsulfonyl and ethylcarbonyl groups such as 2-chloroethylsulfonyl groups and 2-chloroethylcarbonyl groups; vinylsulfonyl groups; vinylcarbonyl groups; oxiranyl groups; isocyanato groups; isothiocyanato groups; aldehydo groups; aziridyl groups; succinimidoxycarbonyl groups; activated acyl groups such as carboxylic acid halide groups; anhydride groups; thioester groups; carbonates such as nitrophenylcarbonates; sulfonic acid esters; phosphoramidates; cyanuric halides such as cyanuric monochlorides and cyanuric dichlorides and cyanuric trichlorides; isothiocyanates, cyanates, nitrogen mustard and sulfur mustard groups, acid chlorides and acid bromides such as carboxylic acid chlorides and sulfonic acid chlorides, and other groups known to be useful as hardening agents in photographic emulsions such as gelatin or synthetic polymers used in photographic coatings.

Typically useful chemical functional groups and methods for the attachment of linkers and vectors together and for the attachment of chromophores and linkers together are described in S. S. Wong, Chemistry of Protein Conjugation and Cross-Linking, CRC Press, Inc., Boston, 1991 (ISBN 0-8493-5886-8).

In one embodiment, these groups are also useful for the reaction of chromophores with linking groups to form the polymer compounds of this invention.

The above listed vector reactive groups can react with a protein or vector or a linker or a chromophore which is chemically modified to contain reactive groups such as amine groups and such as sulfhydryl groups.

Amine groups can be introduced into a chromophore, a linker, or a vector by well known techniques such as, for example, by nitration with nitric acid and sulfuric acid and sometimes nitric acid in acetic anhydride. Nitration occurs in an aromatic group such as a phenyl group or a naphthyl group or benz group such as a benz[e]indole group such as those found in some cyanine and phthalocyanine chromophores or in some linking groups. Sometimes it is advantageous to introduce nitro groups (as well as other functional groups) into a specific site of a precursor used in the synthesis of a chromophore. The nitro group can then be reduced to an amine by reduction such as by an aluminium amalgam reduction, a boron hydride reduction, or by catalytic hydrogenation. Amine groups can also be introduced by conversion of a primary amide to an amine by treatment with hypohalous chloride, and by conversion of a hydroxyl group of an alcohol into a sulfonic acid ester followed by displacement with an azide group and subsequent reduction to an amine, and the like. Sulfhydryl groups can be introduced by well known techniques such as, for example, by conversion of a hydroxyl group of an alcohol into a sulfonic acid ester followed by displacement with sodium sulfide. Sulfhydryl groups can also be introduced after dehydrative amide bond formation between an amine group of a protein and a carboxylic acid group of an acetylated cysteine using a carbodiimide reagent followed by treatment with hydroxylamine, and the like.

In addition, when a protein, peptide, peptoid or peptidomimetic can be chemically modified such as by partial oxidation to introduce an aldehyde group or a carboxylic acid group, a preferred "vector reactive group" can be selected from amino, aminoalkyl, aminoaryl, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxy, carboxy, carboxyalkyl and carboxyaryl. The alkyl portions of the protein reactive group can contain from 1 to about 20 carbon atoms, and the aryl portions of the protein reactive group can contain from about 6 to about 24 carbon atoms.

An additional preferred vector reactive group can comprise a residue of a crosslinking agent. A useful crosslinking agent can react with a functional group such as, for example, an amine or sulfhydryl or carboxylic acid group or aldehyde group found in a linker and with a functional group such as, for example, an amine or sulfhydryl or carboxylic acid group or aldehyde group found in a vector or in a chemically modified protein or biological molecule such as described above. The residues of certain useful crosslinking agents, such as, for example, difunctional gelatin hardeners, bisepoxides and bisisocyanates become a part of, i.e., a linking group in, a vector-linker conjugate which is formed as a result of the crosslinking reaction of such a crosslinking vector reactive group with a chromophore. Vector reactive groups derived from various heterobifunctional crosslinking reagents such as those listed in the Pierce Chemical Company Catalog and handbook—Protein Modification Section, (1994/5) are useful and non-limiting examples of such reagents include:

Sulfo-SMCC: Sulfosuccinimidyl 4-(N-maleimidomethyl) cyclohexane-1-carboxylate
Sulfo-SIAB: Sulfosuccinimidyl (4-iodoacetyl) aminobenzoate.
Sulfo-SMPB: Sulfosuccinimidyl 4-(p-maleimidophenyl) butyrate.
2-IT: 2-Iminothiolane.
SATA: N-Succinimidyl S-acetylthioacetate.

Other useful crosslinking agents, however, facilitate the crosslinking, for example, as consumable catalysts, and are not present in the final conjugate. Examples of such crosslinking agents are carbodiimide and carbamoylonium crosslinking agents as disclosed in U.S. Pat. No. 4,421,847, the disclosure of which is hereby incorporated herein by reference in its entirety, and the dication ethers of U.S. Pat. No. 4,877,724, the disclosure of which is hereby incorporated herein by reference in its entirety. With these crosslinking agents, one of the reactants can have a carboxyl group and the other an amine or sulfhydryl group. The crosslinking agent first reacts selectively with the carboxyl group, preferably a carboxyl group on a vector or chromophore, then is split out during reaction of the "activated" carboxyl group with an amine, preferably an amine group of a linker, to form an amide bond between the vector and a linker or chromophore of this invention, thus covalently bonding the moieties. An advantage of this approach is that crosslinking of like molecules, e.g., chromophore with chromophore, can be avoided, whereas the reaction of bifunctional crosslinking agents is non-selective so that unwanted crosslinked molecules can be obtained.

Additional preferred vector reactive groups include semicarbazido; thiocarbazido; thiosemicarbazido; isocyanato and isothiocyanato; vinyl sulfonylalkyloxy, the alkylene group of which preferably contains from 2 to 10 carbon atoms; vinyl sulfonylalkylpoly(oxyalkyl)oxy, the alkylene group of the sulfonylalkyl portion of which preferably contains from 2 to 10 carbon atoms; the alkylene group of the polyoxyalkyl portion preferably contains from 2 to 10 carbon atoms, such poly(oxyalkyl) portion preferably comprising a poly(oxyethylene) group or a poly(oxyethylene)-co-poly(oxypropylene) copolymer group, and the polymer contains from 2 to about 100 monomeric oxyalkylene units; amidatoalkyloxy, the alkylene group of which preferably contains from 1 to 10 carbon atoms; hydrazidoalkyloxy, the alkylene group of which preferably contains from 1 to 10 carbon atoms; azidocarbonylalkyloxy, the alkylene group of which preferably contains from 1 to 10 carbon atoms; aryloxycarbonyloxyalkyloxy, the alkylene group of which preferably contains from 2 to 10 carbon atoms, and the aryl group of which is as described above; aryloxycarbonyl (polyoxyalkyl)oxy, the aryl group of which is as described above, and the alkylene group of the polyoxyalkyl portion preferably contains from 2 to 10 carbon atoms and is as described above, such poly(oxyalkyl) portion preferably comprising a poly(oxyethylene) group or a poly(oxyethylene)-co-poly(oxypropylene) copolymer group, and the polymer contains from 2 to about 100 monomeric oxyalkylene units; triazines such as 4,6-dichloro-2-triazinylamino, 4,6-dichloro-2-triazinyloxy, 4,6-dichlorotriazinyl-2-oxy(polyalkyloxy), 4-alkoxy-6-chloro-2-triazinyloxy, and 4-alkoxy-6-chloro-2-triazinyl (polyoxyalkyl)oxy, the alkyl groups of the alkoxy portions preferably each containing from 2 to 10 carbon atoms, and the alkylene groups of the polyoxyalkyl portions preferably each containing from 2 to 10 carbon atoms, such a poly(oxyalkyl) portion preferably comprising a poly(oxyethylene) group or a poly(oxyethylene)-co-poly(oxypropylene) copolymer group, in which the polymer contains from 2 to about 100 monomeric oxyalkylene units; formylalkyl, the alkyl group of which preferably contains from 1 to 10 carbon atoms; aminoalkyl, the alkyl group of which preferably contains from 1 to 10 carbon atoms; active esters, for example, succinimidoxycarbonyl; active anhydrides and mixed anhydrides; active carbonates such as arylcarbonatoaryl, alkylcarbonatoaryl, arylcarbonatoalkyl, and alkylcarbonatoalkyl, the alkyl groups of which preferably contain from 2 to 10 carbon atoms and are as described above, and the aryl groups of which are preferably comprised of a six membered ring containing electron withdrawing substituents such as, for example, nitro and halogen, and optionally containing water solubilizing groups such as a sulfonate salt; sulfhydryl; sulfhydrylalkyl, the alkyl group of which preferably contains from 1 to 10 carbon atoms; thioalkylcarbdnylaminoalkyloxy, the alkylene group of the thioalkylcarbonyl portion preferably containing from 1 to 10 carbon atoms, and the alkylene group of the aminoalkyloxy portion preferably containing from 2 to 10 carbon atoms; maleimidoalkylcarbonylaminoalkyloxy, the alkylene group of the maleimidoalkylcarbonyl portion preferably containing from 1 to 10 carbon atoms, and the alkylene group of the aminoalkyloxy portion preferably containing from 2 to 10 carbon atoms; azido; iodoalkylcarbonylamino, the alkylene group of which contains from 1 to 10 carbon atoms; amidatoalkylamino, the alkylene group of which contains from 1 to 10 carbon atoms; and amidatoarylalkylamino, the alkylene group of which contains from 1 to 10 carbon atoms, and the aryl group of which is as described above.

In addition to their utility as vector reactive groups, such groups as described herein are also useful for the covalent attachment of chromophores to linking groups to form the polymers of this invention, and for the covalent attachment of targeting vectors to the polymers of this invention. Attachment can occur to linking groups between two chromophores or via a linking group which is bound to a chromophore. "Targeting vector" refers to, as disclosed in WO-A-96/40285 (Unger), any material or substance which may promote targeting of tissues and/or receptors in vivo with the compositions of the present invention. The targeting vector may be synthetic, semi-synthetic, or naturally occurring. Materials or substances which may serve as targeting vectors include, for example, proteins, including antibodies, glycoproteins and lectins, peptides, polypeptides, saccharides, including mono and polysaccharides, vitamins, steroids, steroid analogs, hormones, cofactors, bioactive agents, and genetic material, including nucleosides, nucleotides and polynucteotides.

A "precursor" to a targeting vector refers to any material or substance which may be converted to a targeting vector. Such conversion may involve, for example, anchoring a precursor to a targeting vector. Exemplary targeting precursor moieties include maleimide groups, disulfide groups, such as 2-pyridyldithio groups, vinylsulfone groups, azide groups, and α-iodoacetyl groups.

"Peptide" refers to a nitrogenous compound which may contain from about 2 to about 100 amino acid residues.

"Protein" refers to a nitrogenous compound which may contain more than about 100 amino acid residues.

"Tissue" refers generally to specialized cells which may perform a particular function. It should be understood that the term "tissue", as used herein, may refer to an individual cell or a plurality or aggregate of cells, for example, membranes or organs. The term "tissue" also includes reference to an abnormal cell or a plurality of abnormal cells. Exemplary tissues include, for example, myocardial tissue (also referred to as heart or myocardium) including myocardial cells and cardiomyocites, membranous tissues, including endothelium and epithelium, laminae, connective tissue, including interstitial tissue, and tumors.

"Receptor" refers to a molecular structure within a cell or on the surface of the cell which is generally characterized by the selective binding of a specific substance. Exemplary receptors include, for example, cell-surface receptors for peptide hormones, neurotransmitters, antigens, complement fragments, and immunoglobulins and cytoplasmic receptors for steroid hormones. An exemplary receptor within the context of the resent invention is the glycoprotein GP2b/111a, which is a platelet integrin.

"Endothelial cells" or "endothelium" refers to an aggregate of cells and/or tissue which may be normal and/or diseased and which may comprise a single layer of flattened transparent endothelial cells that may be joined edge to edge or in an overlapping fashion to form a membrane. Endothelial cells are found on the free surfaces of the serous membranes, as part of the lining membrane of the heart, blood vessels, and lymphatics, on the surface of the brain and spinal cord, and in the anterior chamber of the eye.

Endothelium originates from the embryonic mesoblast and includes heart tissue, including infarcted heart tissue, cardiovasculature, the peripheral vasculature, such as arteries, veins, and capillaries (the location of which is noted as peripheral to the heart), blood clots and the region surrounding atherosclerotic plaque.

"Epithelial cells" or "epithelium" refers to an aggregate of cells and/or tissue which may be normal and/or diseased and which may comprise one or more layers of cells that may be united together by an interstitial cementitious substance supported on a basement-membrane. Epithelium may be classified into various classes, including, for example, a single layer of cells (simple epithelium); more than a single layer of cells (stratified epithelium); and about three or four layers of cells that are fitted together substantially without the appearance of stratification. The different forms of simple epithelium are usually referred to as squamous, pavement, columnar, glandular, spheroidal and/or ciliated. Epithelium originates from the embryonic epiblast or hypoblast. Epithelium includes heart tissue, including infarcted heart tissue, cardiovasculature, the peripheral vasculature, such as arteries, veins, and capillaries, blood clots and the region surrounding atherosclerotic plaque.

In one embodiment, the compositions of the present invention further comprise a targeting vector. The targeting vectors can be associated with lipid compounds, proteins, polymers and/or vesicles either covalently or non-covalently. Thus, in the case of lipid compositions, the targeting vector may be bound, for example, via a covalent or non-covalent bond, to a lipid. It is generally preferred that the targeting vector be bound to a lipid or to a vesicle covalently. Preferably, in the case of lipid compositions which comprise cholesterol, the targeting vector is bound to the cholesterol substantially only non-covalently, and/or that the targeting vector is bound covalently to a component of the composition, for example, another lipid, such as a phospholipid, other than the cholesterol.

If desired, the targeting vectors may also be bound, for example, to biocompatible polymers of this invention. The targeting vectors which are incorporated in the compositions of the present invention are preferably substances which are capable of targeting receptors and/or tissues in vivo. With respect to the targeting of tissue, as noted above, the targeting vectors are desirably capable of targeting heart tissue, including myocardial cells, and membranous tissues, including endothelial and epithelial cells. In the case of receptors, the targeting vectors are desirably capable of targeting GPIIb/IIIa receptors. It is contemplated that preferred targeting vectors for use in targeting tissues and/or receptors, including the tissues and receptors exemplified above, are selected from the group consisting of proteins, peptides, saccharides, steroids, steroid analogs, bioactive agents and genetic material, including, for example, antibodies, glycoproteins and lectins, with peptides being preferred. An example of a protein which may be preferred for use as a targeting vector is Protein A, which is protein that is produced by most of Staphylococcus aureus. Protein A is commercially available, for example, from Sigma Chemical Co. (St Louis, Mo.). Protein A may then be used for binding a variety of IgG antibodies. Generally speaking, peptides which are particularly useful as targeting vectors include natural, modified natural, or synthetic peptides that incorporate additional modes of resistance to degradation by vascularly circulating esterases, amidases, or peptidases. One very useful method of stabilization of peptide moieties incorporates the use of cyclization techniques. As an example, the end-to-end cyclization whereby the carboxy terminus is covalently linked to the amine terminus via an amide bond may be useful to inhibit peptide degradation and increase circulating half-life. Additionally, a side chain-to-side chain cyclization is also particularly useful in inducing stability. In addition, an end-to side chain cyclization may be a useful modification. In addition, the substitution of an L-amino acid for a D-amino acid in a strategic region of the peptide may offer resistance to biological degradation. Suitable targeting vectors, and methods for their preparation, will be readily apparent to one skilled in the art, once armed with the disclosure herein.

In connection with the targeting of endothelial cells, suitable targeting vectors include, for example, one or more of the following: growth factors, including, for example, basic fibroblast growth factor (bFGF), acidic fibroblast growth factor (aFGF), transforming growth factor-alpha (TGF-α), transforming growth factor-beta (TGF-β), platelet-derived endothelial cell growth factor (PD-ECGF) vascular endothelial growth factor (VEGF), and human growth factor (HGF); angiogenin; tumor necrosis factors, including tumor necrosis factor-alpha (TNF-α) and tumor necrosis factor-beta (TNF-β); copper-containing polyribonucleotide angiotropin with a molecular weight of about 4,500, as well as low molecular weight non-peptide angiogenic factors, such as 1-butyryl glycerol; the prostaglandins, including, for example, prostaglandin E1 (PGE1) and prostaglandin E2 (PGE2); nicotinamide; adenosine; dipyridamole; dobutamine; hyaluronic acid degradation products, such as, for example, degradation products resulting from hydrolysis of b linkages, including hyalobiuronic acid; angiogenesis inhibitors, including, for example, collagenase inhibitors; minocycline; medroxyprogesterone; chitin chemically modified with 6-O-sulfate and 6-O-carboxymethyl groups; angiostatic steroids, such as tetrahydrocortisol; and heparin, including fragments of heparin, such as, for example, fragments having a molecular weight of about 6,000, admixed with steroids, such as, for example, cortisone or hydrocortisone; angiogenesis inhibitors, including angioinhibin (AGM-1470—an angiostatic antibiotic); platelet factor 4; protamine; sulfated polysaccharide peptidoglycan complexes derived from the bacterial wall of an Arthobacter species; fungal-derived angiogenesis inhibitors, such as fumagillin derived from *Aspergillus fumigatus*; D-penicillamine; gold thiomalate; thrombospondin; vitamin D3 analogues, including, for example, 1-α,25-dihydroxyvitamin D3 and a synthetic analog, 22-oxa-1-α, 25-dihydroxyvitamin D3; α-interferon; cytokines, such as the interleukins, including, for example, interleukin-I (IL-1), interleukin-2 (IL-2), and interleukin-8 (IL-8) granulocyte macrophage colony stimulating factor (GMCSF); heparin, including low molecular weight fragments of heparin or analogues of heparin; simple sulfated polysaccharides, such as cyclodextrins, including α-, β- and γ-cyclodextrin; tetradecasulfate; transferrin; ferritin; platelet factor 4; protamine; Gly-His-Lys complexed to copper, ceruloplasmin; (12R)-hydroxyeicosatrienoic acid; okadaic acid; lectins; antibodies; Cd11a/CD18; and Very Late Acting Integrin-4 (VLA-4).

Endothelial-leukocyte adhesion molecules (ELAM's) are antigens which are expressed by endothelial cells under conditions of stress which then facilitate the migration of the leukocytes across the endothelium lining the vasculature into the surrounding tissues. It is also the surprising discovery that these same endothelial leukocyte adhesion molecules may be advantageously exploited as receptors for targeting of chromophore polymers. These endothelial cell adhesion molecules belong to a family known as selectins in which the known members, such as GMP-140, all participate in endothelial leukocyte adhesion and include ELAM-1, LAM-1 and the granule membrane protein 140 (GMP-140) also known as platelet activation-dependent granule-external membrane protein (PADGEM), VCAM-1/INCAM-110 (Vascular Adhesion Molecule/Inducible Adhesion Molecule) and ICAM-1 (Intercellular Adhesion Molecule). The cadherin family of cell adhesion molecules may also be used as targeting vectors, including for example, the E-, N-, and P-cadherins, cadherin-4, cadherin-5, cadherin-6, cadherin-7, cadherin-8, cadherin-9, cadherin-10, and cadherin-11; and most preferably cadherin C-5. Further, antibodies directed to cadherins, such as, for example, the monoclonal antibody Ec6C10 may be used to recognize cadherins expressed locally by specific endothelial cells.

A wide variety of different targeting vectors can be selected to bind to the cytoplasmic domains of the ELAM molecules. Targeting vectors in this regard may include lectins, a wide variety of carbohydrate or sugar moieties, antibodies, antibody fragments, Fab fragments, such as, for example, Fab2, and synthetic peptides, including, for example, Arginine-Glycine-Aspartic Acid (R-G-D) which may be targeted to wound healing. While many of these materials may be derived from natural sources, some may be synthesized by molecular biological recombinant techniques and others may be synthetic in origin. Peptides may be prepared by a variety of different combinatorial chemistry techniques as are now known in the art. Targeting vectors derived or modified from human leukocyte origin, such as CD11a/CD18, and leukocyte cell surface glycoprotein (LFA-1), may also be used as these are known to bind to the endothelial cell receptor ICAM-1. The cytokine inducible member of the immunoglobulin superfamily, VCAM-1, which is mononuclear leukocyte-selective, may also be used as a targeting vector. VLA-4, derived from human monocytes, may be used to target VCAM-1. Antibodies and other targeting vectors may be employed to target endoglin, which is an endothelial cell proliferation marker. Endoglin is upregulated on endothelial cells in miscellaneous solid tumors. A targeting vector which may be used to target endoglin is the antibody TEC-11. R-E. Thorpe and F. J. Burrows, *Breast Cancer Research and Treatment*, Vol. 36, pp. 237–51 (1995).

Endothelial cell activation in the setting of atherosclerosis is used in this invention to target the chromophore polymer compositions to regions of arteriosclerosis including, for example, atherosclerotic plaque. One such target that can be used is the inducible mononuclear leukocyte endothelial adhesion molecule recognized by Rbl/9 as an ATHERO-ELAM. The monoclonal antibodies, H4/18 and H18/7, may be used to target endothelial cell surface antigens which are induced by cytokine mediators. As a preferred embodiment of this invention, chromophore polymers are targeted to atherosclerotic plaque to non-invasively detect diseased blood vessels before severe damage has occurred, for example, prior to stroke or myocardial infarction, so that appropriate medical or surgical intervention can be implemented. ATHERO-ELAM is a preferred target and vectors, such as antibodies, peptides, or lectins or combinations thereof may be used to target this cell surface epitope expressed on endothelial cells in the context of atherosclerosis. Alternatively, lipoproteins or lipoprotein fragments derived from low or high density lipoprotein proteins may be used as targeting vectors. Additionally, cholesterol may be used to target the endothelial cells and localize the chromophore polymers to regions of atherosclerotic plaque.

A targeting vector directed toward thrombotic material in the plaque may be used to differentiate between active and inactive regions of atherosclerotic plaque. Active plaques in the process of generating thrombi are more dangerous as these plaques may ultimately occlude a vessel or result in emboli. In this regard, in addition to low molecular weight heparin fragments, other targeting vectors, such as, for example, antifibrin antibody, tissue plasminogen activator (t-PA), anti-thrombin antibody, and fibrin antibodies directed to platelet activation factions, may be used to target active plaque with evolving clots. Most preferred targeting vectors are those which will target a plasma membrane associated GPIIb/IIIa in activated platelets in addition to targeting P-selectin, and an antibody or associated antibody fragment directed to GPIIb/IIIa. The present invention is also useful for detecting regions of acute myocardial infarction. Conveniently, by attaching anti-myosin (particularly cardiomyosin) antibody or anti-actin antibodies to the polymers, infarcted myocardium may be detected by the methods of the present invention. For targeting to granulation tissue (healing wounds), many of the above targeting vectors may be useful. The wound healing tripeptide, arginine-glycine-aspartic acid (RGD), may also be used as a targeting vector in this regard.

As with the endothelial cells discussed above, a wide variety of peptides, proteins and antibodies may be employed as targeting vectors for targeting epithelial cells. Preferably, a peptide, including synthetic, semi-synthetic or naturally occurring peptides, with high affinity to the epithelial cell target receptor may be selected, with synthetic peptides being most preferred. In connection with these preferred embodiments, peptides having from about 5 to about 15 amino acid residues are preferred. Antibodies may be used as whole antibody or antibody fragments, for example, Fab or Fab'2, either natural or recombinant origin. The antibodies of natural origin may be of animal or human origin or may be chimeric (mouse/human). Human recombinant or chimeric antibodies are preferred and fragments are preferred to whole antibody.

Examples of monoclonal antibodies which may be employed as targeting vectors in the present compositions include CALAM 27, which is formed by immunizing BALB/c mice with whole human squamous cell carcinoma of the tongue and forming hybridomas by crossing extracted spleen cells with those of an NS1 syngeneic myeloma cell line. Gloanni, J. et al., *Cancer Research*, Vol. 47, pp. 4417–4424 (1987). CALAM is directed to surface epitopes of both normal and malignant epithelial cells. Normal lymph nodes generally do not contain cells expressing these epitopes. See *Cancer Research*, Vol. 47, pp. 4417–4424 (1987). Accordingly, chromophore polymers comprising this antibody can be used to target metastases in the lymph nodes. The monoclonal antibody 3C2 may be employed as a targeting vector for targeting malignant epithelial cells of serious ovarian carcinoma and endometrioid carcinoma. Another exemplary targeting vector is Mab 4C7 (se, *Cancer Research*, Vol. 45, 2358–2362, 1985) which may be used to target mucinous carcinoma, endometriod carcinoma and mesonephroid carcinoma. For targeting squamous cell carcinoma in head and neck cancer, Mab E48 (*Biological Abstract*, Vol. 099 Issue. 066 Ref 082748) may be used as a targeting vector. For targeting malignant melanoma, the monoclonal antibody 225.28s (*Pathol. Biol.*, Vol. 38 (8), pp. 866–869,1990) may be employed.

Targeting vectors may be selected for targeting antigens, including antigens associated with breast cancer, such as epidermal growth factor receptor (EGFR), fibroblast growth factor receptor, erbB2/HER-2 and tumor associated carbohydrate antigens (Cancer, Vol. 74 (3) pp. 1006–12 (1994)). CTA 16.88, homologous to cytokeratins 8, 18, and 19, is expressed by most epithelial-derived tumors, including carcinomas of the colon, pancreas, breast, ovary and lung. Thus, antibodies directed to these cytokeratins, such as 16.88 (IgM and 88BV59 (IgG3k), which recognize different epitopes on CTA 16.88 (*Semin. Nucl. Med.*, Vol. 23 (2), pp. 165–79 (1993)), may be employed as targeting vectors. For targeting colon cancer, anti-CEA IgG Fab' fragments may be employed as targeting vectors. Chemically conjugated bispecific anti-cell surface antigen, anti-hapten Fab'-Fab antibodies may also be used as targeting vectors. The MG series monoclonal antibodies may be selected for targeting, for example, gastric cancer (*Chin. Med Sci. J.*, Vol. 6(1), pp. 56–59 (1991).

There are a variety of cell surface epitopes on epithelial cells for which targeting vectors may be selected. For example, the protein human papilloma virus (HPV) has been associated with benign and malignant epithelial proliferations in skin and mucosa. Two HPV oncogenic proteins, E6 and E7, may be targeted as these may be expressed in certain epithelial derived cancers, such as cervical carcinoma. See *Curr. Opin. Immunol*. Vol. 6 (5), pp. 746–54 (1994). Membrane receptors for peptide growth factors (PGF-R), which are involved in cancer cell proliferation, may also be selected as tumor antigens. See *Anticancer Drugs*, Vol. 5 (4), pp. 379–93 (1994). Also, epidermal growth factor (EGF) and interleukin-2 may be targeted with suitable targeting vectors, including peptides, which bind these receptors. Certain melanoma associated antigens (MAA), such as epidermal growth factor receptor (EGFR) and adhesion molecules (*Tumor Biol.*, Vol. 15 (4), pp. 188–202 (1994)), which are expressed by malignant melanoma cells, can be targeted with the polymer-chromophore compounds and compositions provided herein. The tumor associated antigen FAB-72 on the surface of carcinoma cells may also be selected as a target.

A wide variety of targeting vectors may be selected for targeting myocardial cells. Exemplary targeting vectors include, for example, anticardiomyosin antibody, which may comprise polyclonal antibody, Fab'2 fragments, or be of human origin, animal origin, for example, mouse origin, or of chimeric origin. Additional targeting vectors include dipyridamole; digitalis; nifedipine; apolipoprotein; low density lipoproteins (LDL), including alpha-LDL, vLDL and methyl LDL; ryanodine; endothelin; complement receptor type 1; IgG Fc; beta 1-adrenergic; dihydropyidine; adenosine; mineralocorticoid; nicotinic acetylcholine and muscarinic acetylcholine; antibodies to the human alpha 1A-adrenergic receptor; bioactive agents, such as drugs, including the alpha 1-antagonist prazosin; antibodies to the anti-beta-receptor; drugs which bind to the anti-beta-receptor, anticardiac RyR antibodies; endothelin-1, which is an endothelial cell-derived vasoconstrictor peptide that exerts a potent positive inotropic effect on cardiac tissue (endothelin-1 binds to cardiac sarcolemmal vesicles); monoclonal antibodies which may be generated to the T cell receptor alpha-beta receptor and thereby employed to generate targeting vectors; the complement inhibitor sCR1; drugs, peptides or antibodies which are generated to the dihydropyridine receptor; monoclonal antibodies directed towards the antiinterleukin 2 receptor may be used as targeting vectors to direct the present chromophore polymer compounds and compositions to areas of myocardial tissue which express this receptor and which may be up-regulated in conditions of inflammation; cyclosporine for similarly directing the compositions to areas of inflamed myocardial tissue; methylisobutyl isonitrile; lectins which bind to specific sugars on membranes of cardiac myocytes and cardiac endothelial cells; adrenomedullin (ADM), which is an endogenous hypotensive and vasorelaxing peptide; atrial natriuretic peptide (ANP); C-type natriuretic peptide (CNP), which is a 22 amino acid peptide of endothelial cell origin and is structurally related to atrial natriuretic peptide but genetically distinct, and possesses vasoactive and antimitogenic activity; vasonatrin peptide (VNP) which is a chimera of atrial natriuretic peptide (ANP) and C-type nathuretic peptide (CNP) and comprises 27 amino acids; thrombin; endothelium derived relaxing factor (EDRF); neutral endopeptidase 1 (NEP-1); competitive inhibitors to EDRF, including, for example, NG-monomethyl-L-arginine (L-NNMA); potassium channel antagonists, such as charybdotoxin and glibenclanmide; antiheart antibodies, which can be identified in patients with idiopathic dilated cardiomyopathy but which preferably do not elicit cytolysis in the myocardium; antibodies directed against the adenine nucleotide translocator, the branched-chain keto acid dehydrogenase or cardiac myosin; specific antagonists for the endothelin-A receptor, which may be referred to as BQ-123; and antibodies to the angiotensin II receptor.

Two of the major antigens of heart muscle fiber sarcolemma are calcium binding glycoproteins which copurify with the dihydropyridine receptor. Antisera may be raised, including polyclonal or monoclonal antibodies, against purified sarcolemma. These antibodies may also be employed as targeted vectors. Purified fractions of the calcium binding glycoproteins may be isolated from the plasma membranes of the sarcolemma and then used to generate antibodies. ANP, which, as noted above, may be used as a targeting vector, can be obtained from cultures of human aortic endothelial cells. ANP is generally localized in endothelium, but also may localize to the endothelial or myocardial tissue. ANP may be prepared, for example, using recombinant techniques, as well as by synthesis of the peptide using peptide synthesis techniques well known to those skilled in the art. It is also possible to use an antibody, either polyclonal or monoclonal, directed towards ANP. Similarly, a peptide directed to ANP may be used for targeting endothelial and/or myocardial cells. Both the beta and alpha forms of atrial natriuretic factor may be used as potential targeting vectors for directing the present polymer chromophore compounds and compositions to myocardial tissue.

A wide variety of targeting vectors may be employed to direct the present polymer chromophore compositions, and particularly chromophore-PAO-chromophore compositions, to the GPIIb/IIIa receptor. Compositions which are directed to the GPIIb/IIIa receptor are highly useful for targeting vascular thromboses or clots, and are useful for diagnosing, as well as treating such clots. Included among such targeting vectors are, for example, peptides, such as Arg-Gly-Asp-Ser (RGDS), Gly-Arg-Gly-Asp-Ser-Pro (GRGDSP), and Gly-Pro-Arg-Pro (GPRP). Pentapeptides containing the sequence Arg-Gly-Asp (RGD) are also useful including, for example, G4120, which is a cyclic peptide containing the amino acid sequence Arg-Gly-Asp (RGD). Also useful are peptides derived from human coagulation Factor XIIIA including, for example, fragments such as: NKLIVRRGQS-FYVQIDFSRPYDPRRDLFRVEYVI-GRYPQENKGTYIPVPIVSELQS GKWGAKIVMREDRS-VRLSIQSSPKCIVGKFRMYVAVWTPYGVLRTSRNPE TDTYIL FNPWCEDDAVYLDNEKEREEYVLN-DIGVIFYGEVN
DIKTRSWSYGQF-R' where R' is —CONH$_2$ or —NH$_2$. In addition, peptides which are fragments of the Factor XIIIA fragment, which include in their sequence the sequence NKLIVRRGOSFYVQIDFSRPYDPRRD or DDAVYLD-NEKEREEYVLNDIGVIFYGEVNDIKTRSWSYGQF. Additional peptides which may be useful as targeting vectors for targeting the GPIIb/IIIa receptor include, for example, peptides comprising the tripeptide sequence of arginine-tyrosine-aspartic acid (Arg-Tyr-Asp; also abbreviated RGD), linked from amino-to-carboxy-terminus and which may bind to the GPIIb/IIIa binding region on activated platelets. Exemplary of such peptides include, for example, peptides of the general formula $R^1$-$(X^1)_n$-Arg-Tyr-Asp-$(Y)_o$-$(X^2)_m$-$R^2$, wherein each of $X^1, X^2$ and Y may independently be one or more amino acid residues while, in certain cases, it is preferred that Y is other than a serine or alanine residue, and each of m, n and o is independently 0 or 1, provided, in certain cases, that when m is 1, then o is 1, and $R^1$ is a protected or unprotected terminal amino group and $R^2$ is a protected or unprotected terminal carboxy group. In a preferred embodiment, $X^1$ is the peptide Ala-Arg-Arg-Ser-Ser-Pro-Ser-Tyr-Tyr and $X^2$ is the peptide Gly-Ala-Gly-Pro-Tyr-Tyr-Ala-Met-Asp-Tyr. Useful peptides include Arg-Ser-Pro-Ser-Tyr-Tyr-Arg-Tyr-Asp-Gly-Ala-Gly-Pro-Tyr-Tyr-Ala-Met-Asp-Tyr and Ala-Arg-Arg-Ser-Pro-Ser-Tyr-Tyr-Arg-Tyr-Asp-Gly-Ala-Gly-Pro-Tyr-Tyr-Ala-Met-Asp-Tyr.

Synthetic compounds which combine a natural amino acid sequence with synthetic amino acids can also be used as the targeting vector, such as a fibrinogen receptor antagonist compound which comprises the sequence XX-Gly-Asp, wherein XX- is a synthetic alpha-amino acid containing a linear side chain, such as

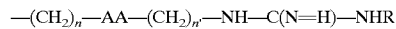

wherein n+n' is 3; AA is a single bond; and R is phenyl or benzyl; or

wherein n is an integer of 1 to 4; n' is an integer of 2 to 4; AA is oxygen, sulfur or a single bond; and R is H, $C_{1-6}$ alkyl, optionally substituted aryl, optionally substituted arylmethyl or optionally substituted cycloalkyl, provided, in certain cases, that when AA is a single bond and R is H, then n+n' is other than 3 or 4. Another such compound comprises a fibrinogen receptor antagonist of formula:

cyclic-[XX-Gly-Asp-ZZ-]

wherein XX is a synthetic alpha-amino acid containing a linear side chain having the formula

or

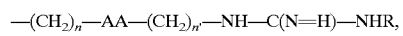

wherein n is an integer of 1 to 4; n' is an integer of 2 to 4; AA is oxygen, sulfur or a single bond; and R is H, $C_{1-6}$ alkyl, optionally substituted cycloalkyl, provided that, in certain cases, when AA is a single bond and R is H, then n+n' is other than 3 or 4, and ZZ is a sequence of 1 to 4 optionally substituted amino acids.

Other useful peptides for use as targeting vectors include, for example, "Elegantin", which has the following sequence: Gly-Glu-Glu-Cys-Asp-Cys-Gly-Ser-Pro-Glu-Asn-Pro-Cys-Cys-Asp-Ala-Ala-Thr-Cys-Lys-Leu-Arg-Pro-Gly-Ala-Gln-Cys-Ala-Asp-Gly-Leu-Cys-Cys-Asp-Gln-Cys-Arg-Phe-Lys-R-R'-Arg-Thr-Ile-Cys-Arg-Arg-Ala-Arg-Gly-Asp-Asn-Pro-Asp-Asp-Arg-Cys-Thr-Gly-Gln-Ser-Ala-Asp-Cys-Pro-Arg-Asn-Gly-Tyr, wherein each of R and R' is independently any amino acid; "Albolabrin", which has the following sequence: Glu-Ala-Gly-Glu-Asp-Cys-Asp-Cys-Gly-Ser-Pro-Ala-Asn-Pro-Cys-Cys-Asp-Ala-Ala-Thr-Cys-Lys-Leu-Leu-Pro-Gly-Ala-Gln-Cys-Gly-Glu-Gly-Leu-Cys-Cys-Asp-Gln-Cys-Ser-Phe-Met-Lys-Lys-Gly-Thr-Ile-Cys-Arg-Arg-Ala-Arg-Gly-Asp-Asp-Leu-Asp-Asp-Tyr-Cys-Asn-Gly-Ile-Ser-Ala-Gly-Cys-Pro-Arg-Asn-Pro-Leu-His-Ala; "Batroxostatin", which has the following sequence: Glu-Ala-Gly-Glu-Glu-Cys-Asp-Cys-Gly-Thr-Pro-Glu-Asn-Pro-Cys-Cys-Asp-Ala-Ala-Thr-Cys-Lys-Leu-Arg-Pro-Gly-Ala-Gln-Cys-Ala-Glu-Gly-Leu-Cys-Cys-Asp-Gln-Cys-Arg-Phe-Lys-Gly-Ala-Gly-Lys-Ile-Cys-Arg-Arg-Ala-Arg-Gly-Asp-Asn-Pro-Asp-Asp-Cys-Thr-Gly-Gln-Ser-Ala-Asp-Cys-Pro-Arg-Phe; and "Flavoridin", which has the following sequence: Gly-Gly-Glu-Cys-Asp-Cys-Gly-Ser- Pro-Glu-Asn-Pro-Cys-Cys-Asp-Ala-Ala-Thr-Cys-Lys-Leu-Arg-Pro-Gly-Ala-Gln-Cys-Ala-Asp-Gly-Leu-Cys-Cys-Asp-Gln-Cys-Arg-Phe-Lys-R-R'-Arg-Thr-Ile-Cys-Arg-Ile-Ala-Arg-Gly-Asp-Phe-Pro-Asp-Asp-Arg-Cys-Thr-Gly-Leu-Ser-Ala-Asp-Cys-Pro-Arg-R-Asn-Asp-Leu, wherein each of R and R' is independently any amino acid.

Other vectors useful for targeting the GPIIb/IIIa receptor include synthetic compounds, such as Ac-(D)-Phe-Pro-boroArg and the cyclic peptidomimetic cyclo(D-2-aminobuyrate-N-Methyl-L-Arginyl-Glycyl-L-Aspartyl-3-amino-methyl-benzoic acid) methanesulfonate salt. Peptides that can also be used include a library of hexapeptides flanked by cysteine residues (capable of forming cyclic disulfides) and cyclic, disulfide-bonded forms of peptides with the sequence Arg-Gly-Asp or Lys-Gly-Asp, as well as the carboxyl-terminal derived peptide, REYVVMWK. Certain matrix glycoproteins such as thrombospondin are also useful in this regard. Members of the serpin family of serine protease inhibitors, such as Plasminogen activator inhibitor type 1 (PAI-1) are other useful vectors.

Generally, it is preferred to employ as targeting vectors for GPIIb/IIIa receptor a peptide having from about 3 to about 20 amino acids, with peptides having from about 4 to about 15 amino acids being more preferred. Even more preferably, targeting vectors for the GPIIb/IIIa receptor may comprise peptides having from about 8 amino acids, with peptides having from about 4 to about 6 amino acids or about 5 amino acids being still more preferred. If desired, the peptides may be cyclized, for example, by (1) sidechain-to-sidechain covalent linkages, including, for example, by the formation of a disulfide linkage via the oxidation of two thiol containing amino acids or analogs thereof, including, for example, cysteine or penicillamine; (2) end-to-sidechain covalent linkages, including, for example, by the use of the amino terminus of the amino acid sequence and a sidechain carboxylate group, such as, for example, a non-critical glutamic acid or aspartic acid group. Alternatively, the end-to-sidechain covalent linkage may involve the carboxylate terminus of the amino acid sequence and a sidechain amino, amidine, guanidine, or other group in the sidechain which contains a nucleophilic nitrogen atom, such sidechain groups including, for example, lysine, arginine, homoarginine, homolysine, or the like; (3) end-to-end covalent linkages that are covalent amide linkages, or the like. Such processes are well known to those skilled in the art. In addition, "pseudocyclization" may be employed, in which cyclization occurs via non-covalent interactions, such as electrostatic interactions, which induces a folding of the secondary structure to form a type of cyclic moiety. It is contemplated that metal ions may aid the induction of a "pseudocyclic" formation. This type of pseudocyclic formation may be analogous to "zinc fingers". As known to one of ordinary skill in the art, zinc fingers involve the formation due to electrostatic interactions between a zinc ion ($Zn^{2+}$) and cysteine, penicillamine and/or homocysteine, of a region in the shape of a loop (the finger). In the case of homocysteine, the RGD sequence would reside at the tip of the finger. Of course, it is recognized that, in the context of the present chromophore polymer invention, any type of stabilizing cyclization would be suitable as long as the recognition and binding peptide vector, such as, for example, RGD, maintains the proper conformation and/or topography to bind to the appropriate receptor in clots with a reasonable Michaelis-Menten constant ($k_m$) or binding constant. As used herein, the term "conformation" refers to the three-dimensional organization of the backbone of the peptide, peptoid, or pseudopeptide, and the term "topography", as used herein, refers to the three-dimensional organization of the sidechain of the peptide, peptoid, or pseudopeptide.

Other suitable targeting vectors include the following compounds: Ac-Cys-Arg-Gly-Asp-Met-Phe-Gly-Cys-$CONH_2$; Ac-Cys-Arg-Gly-Asp-Met-Leu-Arg-Cys$CONH_2$; Ac-Cys-Arg-Gly-Asp-Phe-Leu-Asn-Cys-$CONH_2$; Ac-Cys-Asn-Thr-Leu-Lys-Gly-Asp-Cys-$CONH_2$; Ac-Cys-Asn-Trp-Lys-Arg-Gly-Asp-Cys-$CONH_2$; and Ac-Cys-N-methyl-Arg-Gly-Pen-$CONH_2$, where "Pen" refers to penicillamine (beta,beta-dimethylcysteine).

Other compounds which may be useful as targeting vectors include peptides, or derivatives thereof, represented by the formula A-B-Arg-Gly-Asp-C-D wherein:

A is proline, thioproline, hydroxyproline, dehydroproline, 2-oxo-4thiazolidine carboxylic acid, N-alkyl glycine or an amino acid derivative of the formula:

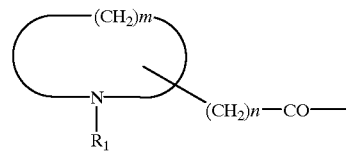

tryptophan, or a tryptophan derivative of the formula:

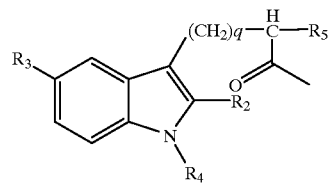

pyroglutamic acid or 2-azetidinone-4-carboxylic acid

B is serine, glycine, valine, alanine, threonine or beta-alanine;

C is an amino acid group having a hydrophobic functional group, and

D is hydroxy or amino:

wherein:

$R_1$ is hydrogen, $-(CH_2)_pCH_3$ or $-CO-(CH_2)_pCH_3$, $R_2$ is hydrogen or alkyl;

$R_3$ is hydrogen or alkoxy;

$R_4$ is hydrogen or alkyl;

$R_5$ is hydrogen, amino or acylamino;

m is an integer of 2 to 5;

n is an integer of 0 to 2;

p is an integer of 0 to 5; and q is an integer of 0 to 3.

Another targeting vector which may be suitable for use in connection with the present dye polymer compositions is a peptide, a peptide derivative, or a salt thereof having the formula:

A-B-Arg-Gly-Asp-C-D wherein:

A is orotic acid or hydroorotic acid;

B is an amino acid;

C is an amino acid having a hydrophobic functional group; and

D is hydroxy or amino.

In the above compounds, examples of amino acids having hydrophobic functional groups in the definition of "C" are tryptophan and phenylalanine.

Various peptides which would be suitable for use as a targeting vector connection with the present chromophore polymer invention, especially for targeting GPIIb/IIIa are disclosed, for example, in Sat et al., U.S. Pat. No. 5,498,601 and the following published European Patent Applications: 0 368 486 A, 0 382 451 A, and 0 422 938 B1, the disclosures of which are hereby incorporated herein by reference, in their entirety. Other targeting vectors which may be used in the compositions of the present invention, in addition to those exemplified above, would be apparent to one of ordinary skill in the art, once armed with the present disclosure. Other suitable targeting vectors include, for example, conjugated peptides, such as, for example, glycoconjugates and lectins, which are peptides attached to sugar moieties. The compositions may comprise a single targeting vector, as well as two or more different targeting vectors.

In the chromophore polymers of this invention, a chromophore or a linking group can be attached to a targeting vector, Q, or a precursor thereto. In embodiments where Q is a targeting vector, Q preferably targets cells or receptors selected from the group consisting of myocardial cells, endothelial cells, epithelial cells, tumor cells and the glycoprotein GPIIb/IIIa receptor. In certain preferred embodiments, Q targets cells or receptors selected from the group consisting of myocardial cells, endothelial cells, epithelial cells and the glycoprotein GPIIb/IIIa receptor. In addition, in embodiments where Q is a targeting vector, Q is preferably selected from the group consisting of proteins, peptides, saccharides, steroids, steroid analogs, bioactive agents, and genetic material. In these latter embodiments, Q is preferably selected from the group consisting of proteins, peptides and saccharides. In embodiments where Q comprises a peptide, Q is preferably the peptide -Lys-Gln-Ala-Gly-Asp-Val or a cyclic peptide, such as DMP 728. (See, e.g., Mousa et al., *Thrombosis Research*, Vol. 76 (2), pp. 109–119 (1994)), the disclosures of which are hereby incorporated herein by reference, in their entirety. In embodiments where Q comprises a protein, Q is preferably Protein A. In embodiments where Q comprises a saccharide, Q can be selected from the group consisting of monosaccharides and disaccharides. Useful monosaccharides in this invention include monosaccharides having six carbons such as allose, altrose, glucose, mannose, gulose, idose, galactose, talose, fructose, psicose, and tagatose; monosaccharides having five carbons such as ribose, arabinose, xylose, lyxose, ribulose and xylulose; monosaccharides having four carbons such as erythrose, threose and erythulose. Useful disaccharides include sucrose, lactose, maltose, isomaltose and cellobiose. In embodiments where Q comprises a saccharide, Q is preferably a monosaccharide, with mannose and glucose being more preferred.

In embodiments where Q is a precursor to a targeting vector, Q preferably comprises a partially unsaturated or aromatic 5- to 7-membered monocyclic ring containing 1 or 2 N, O or S atoms, and more preferably a maleimide moiety or a pyridyl moiety. In embodiments where Q is a targeting vector, preferably Q is a targeting vector that targets cells or receptors selected from the group consisting of myocardial cells, endothelial cells, epithelial cells, tumor cells, and the glycoprotein GPIIa/IIIb receptor. Also in preferred embodiments, Q is a targeting vector selected from the group consisting of proteins, peptides, saccharides, steroids, steroid analogs, bioactive agents and genetic material, with proteins, peptides, and saccharides being more preferred. Also preferred are targeting vectors which target regions of arteriosclerosis, especially atherosclerotic plaque. Also preferred are targeting vectors which target infarcted myocardium. In certain embodiments, the targeting vectors target cancer cells.

The foregoing preferred embodiments of the compounds of the present invention are preferred for various reasons, including ease of synthesis, diagnostic efficacy, enhanced biocompatibility, and/or improved targeting efficacy.

The targeting vector may be incorporated in the present chromophore polymer compositions in a variety of ways. Generally speaking, the targeting vector may be incorporated in the present compositions by being associated covalently or non-covalently with one or more of the chromophores and/or the linking groups of the chromophore polymers of this invention. In preferred form, the targeting vector is associated covalently with one or more of the chromophores and/or the linking groups. In preferred compounds of the present invention the targeting vectors are preferably associated covalently with the linking groups of the chromophore polymer compounds.

Exemplary covalent bonds by which the targeting vectors are associated with the polymers include, for example, amide (—CONH—); thioamide (—CSN—H—); ether (ROR', where R and R' may be the same or different and are other than hydrogen); ester (—COO—); thioester (—COS—); —O—; —S—; —S$_n$—, where n is greater than 1, preferably about 2 to about 8, and more preferably about 2; carbamates; —NH—; NR—, where R is alkyl, for example, alkyl of from 1 to about 4 carbons; urethane; and substituted imidate; and combinations of two or more of these. Covalent bonds between targeting vectors and chromophores and covalent bonds between targeting vectors and linking groups may be achieved through the use of molecules that may act as spacers to increase the conformational and topographical flexibility of the vector. Examples of such spacers include, for example, succinic acid, 1,6-hexanedioic acid, 1,8-octanedioic acid, and the like, as well as modified amino acids, such as, for example, 6-aminohexanoic acid, 4-aminobutanoic acid, and the like. In addition, in the case of targeting vectors which comprise peptide moieties, sidechain-to-sidechain crosslinking may be complemented with sidechain-to-end crossing and/or end-to-end crosslinking. Also, small spacer molecules, such as dimethylsuberimidate, may be used to accomplish similar objectives. The use of agents, including those used in Schiff's base type reactions, such as glutaraldehyde, may also be employed. The Schiff's base linkages, which may be reversible linkages, can be rendered more permanent covalent linkages via the use of reductive amination procedures. This may involve, for example, chemical reducing agents, such as lithium aluminum hydride reducing agents or their milder analogs, including lithium aluminum diisobutyl hydride (DIBAL), sodium borohydride (NaBH$_4$) or sodium cyanoborohydride (NaBH$_3$CN).

The covalent linking of the targeting vectors to the chromophores and linking groups in the present compounds may be accomplished using synthetic organic techniques which would be readily apparent to one of ordinary skill in the art, based on the present disclosure. For example, the targeting vectors may be linked to the chromophores or linking groups via the use of well known coupling or activation agents. As known to the skilled artisan, activating agents are generally electrophilic. This electrophilicity can be employed to elicit the formation of a covalent bond. Exemplary activating agents which may be used include, for example, carbonyldiimidazole (CDI), dicyclohexylcarbodiimide (DCC), di-isopropylcarbodiimide (DIC), methyl sulfonyl chloride, Castro's Reagent, and diphenyl phosphoryl chloride.

The covalent bonds may involve crosslinking and/or polymerization. Crosslinking preferably refers to the attachment of two chains of polymer molecules by bridges, composed of either an element, a group, or a compound, which join certain carbon atoms of the chains by covalent chemical bonds. For example, crosslinking may occur in polypeptides which are joined by the disulfide bonds of the cystine residue. Crosslinking may be achieved, for example, by (1) adding a chemical substance (cross-linking agent) and exposing the mixture to heat, or (2) subjecting a polymer to high energy radiation. A variety of crosslinking agents, or "tethers", of different lengths and/or functionalities described, for example, in R. L. Lunbland, Techniques in Protein Modification, CRC Press, Inc., Ann Arbor, Nebr., pp. 249–68 (1995), the disclosures of which are hereby incorporated herein by reference, in their entirety. Exemplary crosslinkers include, for example, 3,3'-dithiobis (succinimidylpropionate), dimethyl suberimidate, and its variations thereof, based on hydrocarbon length and bis-N-maleimido-1,8-octane.

The residue of a vector is independently linked to another component of the polymer of this invention through a chemical bond or a linking group, as disclosed in US-A-5583206 (Snow et al.). Preferred linking groups may be derived from vector reactive groups and so include nitrogen atoms in groups such as amino, imido, nitrilo and imino groups; alkylene, preferably containing from 1 to 18 carbon atoms such as methylene, ethylene, propylene, butylene and hexylene, such alkylene optionally being interrupted by 1 or more heteroatoms such as oxygen, nitrogen and sulfur or heteroatom-containing groups; carbonyl; sulfonyl; sulfinyl; ether; thioether; ester, i.e., carbonyloxy and oxycarbonyl; thioester, i.e., carbonylthio, thiocarbonyl, thiocarbonyloxy, and oxythiocarboxy; amide, i.e., iminocarbonyl and carbonylimino; thioamide, i.e., iminothiocarbonyl and thiocarbonylimino; thio; dithio; phosphate; phosphonate; urelene; thiourelene; urethane, i.e., iminocarbonyloxy,and oxycarbonylimino; an amino acid linkage, i.e., a

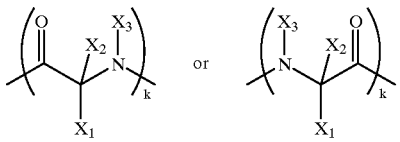

group wherein k=1 and $X_1$, $X_2$, $X_3$ independently are H, alkyl, containing from 1 to 18, preferably 1 to 6 carbon atoms, such as methyl, ethyl and propyl, such alkyl optionally being interrupted by 1 or more heteroatoms such as oxygen, nitrogen and sulfur, substituted or unsubstituted aryl, containing from 6 to 18, preferably 6 to 10 carbon atoms such as phenyl, hydroxyiodophenyl, hydroxyphenyl, fluorophenyl and naphthyl, aralkyl, preferably containing from 7 to 12 carbon atoms, such as benzyl, heterocyclyl, preferably containing from 5 to 7 nuclear carbon and one or more heteroatoms such as S, N, P or O, examples of preferred heterocyclyl groups being pyridyl, quinolyl, imidazolyl and thienyl; heterocyclylalkyl, the heterocyclyl and alkyl portions of which preferably are described above; or a peptide linkage, i.e., a

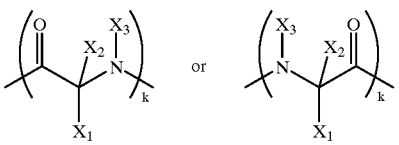

group wherein k>1 and each X independently is represented by a group as described for $X_1$, $X_2$, $X_3$ above. Two or more linking groups can be used, such as, for example, alkyleneimino and iminoalkylene. It is contemplated that other linking groups may be suitable for use herein, such as linking groups commonly used in protein heterobifunctional and homobifunctional conjugation and crosslinking chemistry as described above. Especially preferred linking groups include amide groups and also amino groups. When linked to the residue of a chromophore via an isothiocyanate group on the chromophore, amine groups become thiourea groups.

The linking groups can contain various substituents which do not interfere with the coupling reaction between the chromophore and the other components of this invention. The linking groups can also contain substituents which can otherwise interfere with such reaction, but which during the coupling reaction, are prevented from so doing with suitable protecting groups commonly known in the art and which substituents are regenerated after the coupling reaction by suitable deprotection. The linking groups can also contain substituents that are introduced after the coupling reaction. For example, the linking group can be substituted with substituents such as halogen, such as F, Cl, Br or I; an ester group; an amide group; alkyl, preferably containing from 1 to about 18, more preferably, 1 to 4 carbon atoms such as methyl, ethyl, propyl, i-propyl, butyl, and the like; substituted or unsubstituted aryl, preferably containing from 6 to about 20, more preferably 6 to 10 carbon atoms such as phenyl, naphthyl, hydroxyphenyl, iodophenyl, hydroxyiodophenyl, fluorophenyl and methoxyphenyl; substituted or unsubstituted aralkyl, preferably containing from 7 to about 12 carbon atoms, such as benzyl and phenylethyl; alkoxy, the alkyl portion of which preferably contains from 1 to 18 carbon atoms as described for alkyl above; alkoxyaralkyl, such as ethoxybenzyl; substituted or unsubstituted heterocyclyl, preferably containing from 5 to 7 nuclear carbon and heteroatoms such as S, N, P or O, examples of preferred heterocyclyl groups being pyridyl, quinolyl, imidazolyl and thienyl; a carboxyl group; a carboxyalkyl group, the alkyl portion of which preferably contains from 1 to 8 carbon atoms; or the residue of a chromophore.

In accordance with preferred embodiments, the targeting vectors may be linked or attached to the chromophores and linking groups of the polymers of this invention via a linking group. A variety of linking groups are available and would be apparent to one skilled in the art once armed with the present disclosure. Preferably, the linking group comprises a hydrophilic polymer. Suitable hydrophilic linker polymers include, for example, polyvinylpyrrolidones, poly(vinyl methyl ethers), polyacrylamides, such as, for example, poly (methacrylamides), poly(N,N-dimethylacrylamides) and poly(hydroxypropylmethylamides), poly(hydroxyethyl acrylates), polyhydroxypropyl methacrylates, polymethyloxazolines, polyethyloxazolines, polyhydroxyethyloxazolines, polyhydroxypropyloxazolines, polyvinyl alcohols, polyphosphazenes, poly(hydroxyalkylcarboxylic acids), polyoxazolidines, and polyaspartamide. The hydrophilic polymers are preferably selected from the group consisting of polyvinylalcohol and polyvinylpyrrolidone and copolymers thereof. The hydrophilic polymer used as a linking group is preferably a bifunctional polymer. In this case, one end of the hydrophilic polymer is linked to a chromophore or linking group of the polymer of this invention, and the other end of the hydrophilic polymer is linked to the targeting vector, for example, via an amide bond. A hydrophilic polymer substituted with a terminal carboxylic acid group on one end and an terminal amino group on the other end may also be used. These latter bifunctional hydrophilic polymers may be preferred in some embodiments since they possess various similarities to amino acids. Standard peptide methodology may be used to link the targeting vector to the chromophore or linking groups of the polymer of this invention. Bifunctional hydrophilic polymers may be synthesized using standard organic chemistry methodologies. In addition, many of these materials are available commercially. An advantage of using a hydrophilic polymer material as a linking group is that the size of the polymer can be varied such that the number of monomeric subunits may be as few as, for example, about 5, or as many as, for example, about 500 or even greater. Accordingly, the "tether" or length of the linkage may be varied as desired. This may be important, depending, for example, on the particular targeting vector employed. For example, a targeting vector which comprises a large protein molecule may require a short tether, such that it will simulate a membrane bound protein. A short tether would also allow the chromophore polymer to reside proximal to the cell of interest and thus facilitate further chromophore-polymer to cell interaction such as hydrophobic chromophore in the polymer to lipid or protein in the cell membrane.

Linking moieties (L, L', L", L''', etc.) can be selected from the group consisting of a $C_1$ to $C_{16}$ alkylene group, optionally containing hydrophilic functional groups selected from the group consisting of hydroxyl groups, carboxyl groups, phosphonate groups, sulfonate groups, sulfate groups, phosphate groups, amino groups, amino acid groups; an ether oxygen atom; an oxycarbonyl ester group; a carbonate group; a succinate diester; a phenylurea group; a phenylthiourea group; a nitrilo group; an oxyaceto group; a 2-oxytriazin-4-yl group; a sulfur atom; a sulfone group; a sulfoxide group; a carbonyloxy group; an oxyphenylaminothiocarbonylamino group; an oxyphenylaminocarbonylamino group; a phosphate group; and amino acid group; a urea group; a thiourea group; a urethane group; and a thiourethane group.

Examples of linking moieties include alkylene groups such as methylene groups and $C_{2-16}$ alkylene linear and branched chain groups such as ethylene, n-propylene, isopropylene, n-butylene, iso-butylene, n-pentylene, isopentylene, hexylene, heptylene, octylene and the like, optionally substituted with carboxy groups, carboxymethyl groups, sulfate groups, sulfonatoalkyl groups, halogen containing groups such as perfluoroalkyl groups such as trifluormethyl, and alkoxy groups such as methoxy, ethoxy, propoxy, isopropoxy, n-butoxy, isobutoxy, tert-butoxy and the like which, together with the carbons of the alkylene group, total less than or equal to 17 carbons. Additional examples of linking groups include $C_6$ phenylene groups and $C_{7-16}$ alkylenylphenylene groups, and $C_{8-16}$ alkylenephenylenealkylene groups. These are optionally substituted with carboxy groups, carboxymethyl groups, sulfate groups, sulfonatomethyl groups, fluorine atoms such as from one to four fluorine atoms on the phenylene ring and perfluorinated on the alkylene groups, $C_{1-10}$ perfluoroalkyl groups, $C_{1-10}$ sulfonatoalkyl groups, the alkyl portion of which is described above, $C_{1-10}$ alkyl groups, the alkyl portion of which is as described above, $C_{1-10}$ alkoxyl groups, the alkyl portion of which is as described above alkylene groups of which optionally contain heteroatoms selected from O, S, and N separated by at least two carbon atoms, thiocarbonylaminophenylene groups.

Further examples of linking groups are polymeric units. As used herein, a polymeric unit may be of natural, semi-synthetic (modified natural) or synthetic origin. The term "polymeric unit" denotes a compound comprised of two or more repeating monomeric units, and preferably 10 or more repeating monomeric units. The phrase semi-synthetic polymeric unit (or modified natural polymeric unit), as employed herein, denotes a natural polymer unit that has been chemically modified in some fashion. Exemplary natural polymeric units suitable for use in the present invention include naturally occurring polysaccharides. Such polysaccharides include, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, polydextrose, pustulan, chitin, agarose, keratan, chondroitan, dermatan, hyaluronic acid, alginic acid, xanthan gum, starch and various other naturalhomopolymer or heteropolymers, such as those containing one or more of the following: aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serene, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosaminc, and neuraminic acid, and naturally occurring derivatives thereof. Accordingly, suitable polymers include, for example, proteins, such as albumin. Exemplary semi-synthetic polymeric units include carboxymethylcellulose, hydroxymethylcellulose, hydroxypropylmethylcellulose, methylcellulose, and methoxycellulose. Exemplary synthetic polymeric units suitable for use in the present invention include polyethyleneglycol (PEG), polymethylenes (such as, for example, polyethylene and also polyethylene terephthlate), polypropylenes (such as, for example, poly(propylene glycol)), polyurethanes, poly(vinyl acetate), partially hydrolyzed polyvinyl acetate (such as, for example, poly(vinyl acetate-co-vinyl alcohol)), poly(vinyl alcohol) such as, for example, polyvinyl alcohol (PVA), poly(vinyl chloride), poly(N-vinylpyrrolidone), polyamides including nylon polyamides, polystyrene, poly (3-methoxystyrene), poly(4-methoxystyrene), poly(3,4-dimethoxystyrene), poly(3,4-methylenedioxystyrene), polylactic acids, fluorinated hydrocarbons, fluorinated carbons (such as, for example, polytetrafluoroethylene), and polymethylmethacrylate, and derivatives thereof. Preferred are biocompatible synthetic polymeric units or copolymeric units prepared from monomers, such as ethylene, acrylic acid, methacrylic acid, ethyleneimine, crotonic acid, acrylamide, ethyl acrylate, methyl methacrylate, 2-hydroxyethyl methacrylate (HEMA), lactic acid, glycolic acid, E-caprolactone, acrolein, cyanoacrylate, bisphenol A, epichlorohydrin, hydroxyalkylacrylates, siloxane, dimethylsiloxane, ethylene oxide, propyleneoxide, ethylene glycol, hydroxyalkylmethacrylates, N-substituted acrylamides, N-substituted methacrylamides, N-vinyl-2- pyrrolidone, 2,4-pentadiene-1-ol, vinyl acetate, acrylonitrile, styrene, p-aminostyrene, p-aminobenzylstyrene, p-vinylbenzylamine, sodium styrene sulfonate, sodium 2-sulfoxyethylmethacrylate, vinylpyridine, 2-methyl-5-vinyl pyridine, 2-vinyl pyridine, 4-vinyl pyridine, aminoethyl methacrylates, 2-methacryloyloxytrimethylammonium chloride, and polyvinylidene, as well polyfunctional crosslinking monomers such as N,N'-methylenebisacrylamide, ethylene glycol dimethacrylates, 2,2'-(p-phenylenedioxy)diethyl dimethacrylate, divinylbenzene, triallylamine and methylenebis-(4-phenylisocyanate), including combinations thereof. Preferable polymeric units include poly(acrylic acid), poly(ethyleneimine), poly(methacrylic acid), poly(methyl methacrylate), polysiloxane, polydimethylsiloxane, polylactic acid, poly(E-caprolactone), epoxy resin, melamines, triazinamine, triamino-s-triazine and polyamide (nylon) polymers. Preferable copolymer units include the following: polyvinylidene-polyacrylonitrile-poly(methyl methacrylate), polystyrene-polyacrylonitrile and poly d,l-lactide-co-glycolide polymers.

A hydrophilic polymer unit may conveniently be selected from the group consisting of polyethylene glycols (PEG), polyvinyl alcohol, polyvinylpyrrolidones, polyacrylamides, polymethacrylamides, polyphosphazenes, poly(hydroxyalkylcarboxylic acids) and polyoxazolidines.

The molecular weight of the linker may vary, depending, for example, on the particular end-use of the compounds.

In one aspect, the linking group is a polymer unit having a molecular weight which ranges from about 100 to about 10000, and all combinations and subcombinations of ranges therein. More preferably, it is a polymer unit having a molecular weight of from about 1000 to about 10000. Also preferred are polymer units which exhibit polydispersities ranging from greater than about 1 to about 3, and all combinations and subcombinations of ranges therein. More preferably, the linking group is a polymer unit having a polydispersity of from greater than about 1 to about 2, with polydispersities of from greater than about 1 to about 1.5 being even more preferred, and polydispersities of from greater than about 1 to about 1.2 being still more preferred.

Other suitable biocompatible monomers and polymer units will be readily apparent to those skilled once armed with the present disclosure. These include negatively charged lipids such as phosphatidic acids and lipids bearing a hydrophilic polymer such as a lipid covalently linked to the polymer unit. The polymer may be bound to the chromophore through a covalent bond, such as an amide, carbamate or linkage.

Thus the linking group can be a lipid selected from the group consisting of lecithins, phosphatidylcholines, phosphatidylserines, phosphatidylinositols, cardiolipins, cholesterols, cholesterolamines, lysophosphatides, erythrosphingosines, sphingomyelins, ceramides, cerebrosides, saturated phospholipids, unsaturated phospholipids, and krill phospholipids.

Alternatively, the linking group can be a lipid selected from the group consisting of 1,2-diacyl-sn-glycero-3-phosphocholines, 1,2-diacyl-sn-glycero-3-phosphoethanolamines, 1,2-diacyl-sn-glycero-3-[phospho-rac-(1-glycerols)], 1,2-diacyl-sn-glycero-3-phosphates, 1,2-diacyl-sn-glycero-3-[phosphoserines], lysophosphatidylcholines, lysophosphatidylglycerols, 1,2-diacyl-sn-glycerols, 1,2-diacyl-ethylene glycols, N-(n-caproylamine)-1,2-diacyl-sn-glycero-3-phosphoethanolamines, N-dodecanylamine-1,2-diacyl-sn-glycero-3-phosphoethanolamines, N-succinyl-1,2-diacyl-sn-glycero-3-phosphoethanolamines, N-glutaryl-1,2-diacyl-sn-glycero-3-phosphoethanolamines and N-dodecanyl-1,2-diacyl-sn-glycero-3-phosphoethanolamines. More preferably, the linking group is a lipid selected from the group consisting of 1,2-diacyl-sn-glycero-3-phosphocholines, 1,2-diacyl-sn-glycero-3-phosphoethanolamines, 1,2-diacyl-sn-glycero-3-[phospho-rac-(1-glycerols)], 1,2-diacyl-sn-glycero-3-phosphates, 1,2-diacyl-sn-glycero-3-[phosphoserines], lysophosphatidylcholines, lysophosphatldylglycerols and 1,2-diacyl-sn-glycerols.

In other preferred embodiments, the linking group is a protein or peptide such as protein which comprises albumin.

In a further embodiment of the present invention, the linking groups of this invention can comprise the residue of groups that can interact with X-ray radiation. Examples of such groups are those which contain iodine such as iodinated aromatic groups such as iohexol and derivatives of iodobenzene, diiodobenzene, and triiodobenzene, with derivatives of triiodobenzene being preferred. Iodinated aromatic compounds, when used as linking groups are preferably substituted with hydrophilic groups such as derivatives of glycerol, dihydroxypropyl alcohol, dihydroxypropyl amine such as dihydroxypropyl amido groups, carbohydrate groups.

In another embodiment, the linking group can comprise a monomeric unit. As used herein, the term monomeric unit refers to any group that can link two or more chromophores or PAOs. Exemplary monomeric units suitable for use in the present invention include ethylene, phenylene, diacids such as succinic acid, adipic acid, tartaric acid, amino acids such as glycine, serene, threonine, cysteine, tyrosine, asparagine, glutamine, aspartic acid, glutamic acid, lysine, arginine, histidine, glucuronic acid, gluconic acid, glucaric acid, galacturonic acid, manuronic acid, glucosamine, galactosamine, and neuraminic acid, and naturally occurring derivatives thereof, monosaccharides such as erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, and the like. Exemplary monosaccharides may have six carbon atoms and these saccharides include allose, altrose, glucose, mannose, gulose, idose, galactose, talose, fructose, psicose, and tagatose. Exemplary monosaccharides may have five carbon atoms and these saccharides include ribose, arabinose, xylose, lyxose, ribulose and xylulose. Exemplary monosaccharides may have four carbon atoms and these saccharides include erythrose, threose and erythrulose.

In still other preferred embodiments, the linking group can be a monomer unit or a combination of monomer units. Representative monomer units are selected from the group consisting of an amino acid, acrylic acid, methacrylic acid, ethyleneimine, crotonic acid, acrylamide, ethyl acrylate, methyl methacrylate, 2-hydroxyethyl methacrylate, lactic acid, glycolic acid, E-caprolactone, acrolein, cyanoacrylate, bisphenol A, epichlorohydrin, hydroxyalkylacrylates, siloxane, dimethylsiloxane, hydroxyalkyl methacrylates, N-substituted acrylamides, N-substituted methacrylamides, N-vinyl-2-pyrrolidone, 2,4-pentadiene-1-ol, vinyl acetate, acrylonitrile, styrene, p-aminostyrene, p-aminobenzylstyrene, sodium styrene sulfonate, sodium 2-sulfoxyethylmethacrylate, vinyl pyridine, aminoethyl methacrylates and 2-methacryloyloxytrimethylammonium chloride. Other monomer units include melamines, triazinamine, triamino-s-triazine, iodinated aromatic groups such as iohexol and derivatives of iodobenzene, diidobenzene, and triiodobenzene, with derivatives of triiodobenzene being preferred. Other monomeric linking groups include derivatives of ethylenediamine such as ethylenediaminetetraacetic acid, diethylenetriamine such as diethylenetriaminepentaacetic acid, and metal chelates of these derivatives where the metal is described hereinbelow.

Other monomer units which may be used include chelating agents. A chelating group as used herein comprises the residue of one or more of a wide variety of chelating agents that can have a metal ion associated therewith. In the compounds of the invention where the linker group comprises a chelating agent residue, it is particularly preferred that such residue be metallated with a therapeutically or diagnostically effective metal ion, e.g. a heavy metal ion or cluster ion, a paramagnetic metal ion, a fluorescent metal ion, or a radionuclide.

As is well known, a chelating agent is a compound containing donor atoms that can combine by coordinate bonding with a metal atom to form a cyclic structure called a chelation complex or chelate. This class of compounds is described in the Kirk-Othmer Encyclopedia of Chemical Technology, Vol. 5, 339–368.

The residue of a suitable chelating agent can be selected from polyphosphates, such as sodium tripolyphosphate and hexametaphosphoric acid; aminocarboxylic acids, such as ethylenediaminetetraacetic acid, N-(2-hydroxyethyl) ethylene-diaminetriacetic acid, nitrilotriacetic acid, N,N-di (2-hydroxyethyl)glycine, ethylenebis (hydroxyphenylglycine) and diethylenetriamine pentacetic acid; 1,3-diketones, such as acetylacetone, trifluoroacetylacetone, and thenoyltrifluoroacetone; hydroxycarboxylic acids, such as tartaric acid, citric acid, gluconic acid, and 5-sulfosalicylic acid; polyamines, such as ethylenediamine, diethylenetriamine, triethylenetetramine, and triaminotriethylamine; aminoalcohols, such as triethanolamine and N-(2-hydroxyethyl)ethylenediamine; aromatic heterocyclic bases, such as 2,2'-diimidazole, picoline amine, dipicoline amine and 1,10-phenanthroline; phenols, such as salicylaldehyde, disulfopyrocatechol, and chromotropic acid; aminophenols, such as 8-hydroxyquinoline and oximesulfonic acid; oximes, such as dimethylglyoxime and salicylaldoxime; peptides containing proximal chelating functionality such as polycysteine, polyhistidine, polyaspartic acid, polyglutamic acid, or combinations of such amino acids; Schiff bases, such as disalicylaldehyde 1,2-propylenediimine; tetrapyrroles, such as tetraphenylporphin and phthalocyanine; sulfur compounds, such as toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea; synthetic macrocyclic compounds, such as dibenzo[18]crown-6, $(CH_3)_6$-[14]-4,11-diene-$N_4$, and (2.2.2-cryptate); phosphonic acids, such as nitrilotrimethylene-phosphonic acid, ethylenediaminetetra (methylenephosphonic acid), and hydroxyethylidenediphosphonic acid, or combinations of two or more of the above agents.

The residue of a suitable chelating agent preferably comprises a polycarboxylic acid group and includes: ethylenediamine-N, N, N',N'-tetraacetic acid (EDTA); N,N, N',N",N"-diethylene-triaminepentaacetic acid (DTPA); 1,4,7,10-tetraazacyclododecane-N,N',N",N"'-tetraacetic acid (DOTA); 1,4,7,10-tetraazacyclododecane-N,N',N"-triacetic acid (DOTA); 1-oxa-4,7,10-triazacyclododecane-N,N',N"-triacetic acid (OTTA); trans(1,2)-cyclohexanodiethylenetriamine pentaacetic acid (CDTPA).

In one embodiment, other suitable residues of chelating agents comprise proteins modified for the chelation of metals such as technetium and rhenium as described in U.S. Pat. No. 5,078,985, the disclosure of which is hereby incorporated by reference.

In a further embodiment, suitable residues of chelating agents are derived from compounds containing $N_3S$ and $N_2S_2$ containing compounds, as for example, those disclosed in U.S. Pat. Nos. 4,444,690; 4,670,545; 4,673,562; 4,897, 255; 4,965,392; 4,980,147; 4,988,496; 5,021,556 and 5,075, 099.

Other suitable residues of chelating agents are described in PCT/US91/08253, the disclosure of which is hereby incorporated by reference.

If the compounds of the invention comprise the residue of multiple chelating agents, such agents can be linked together by linking groups such as described herein.

Preferred chelating groups are selected from the group consisting of 2-aminomethylpyridine, iminoacetic acid, iminodiacetic acid, ethylenediaminetetraacetic acid (EDTA), diethylenetriaminepentaacetic acid (DTPA), 1,4,7,10-tetraazacyclododecane-1,4,7,10-tetraacetic acid (DOTA), carbonyliminodiacetic acid, methyleneiminoacetic acid, methyleneiminodiacetic acid, ethylenethioethyleneiminoacetic acid, ethylenethioethyleneiminodiacetic acid, TMT (see the Journal of the American Chemical Society (1993) 115, 11032), a terpyridinyl group, a chelating agent comprising a terpyridyl group and a carboxymethylamino group, or a salt of any of the foregoing acids. An especially preferred chelating group is DTPA.

Representative chelating groups are also described in U.S. Pat. No. 5,559,214, WO 95/26754, WO 94/08624, WO 94/09056, WO 94/29333, WO 94/08624, WO 94/08629, WO 94/13327 and WO 94/12216.

Preferable chelating agents include, for example, diethylenetriaminepentaacetic acid (DTPA), ethylenediaminetetraacetic acid (EDTA), 1,4,7,10-tetraazacyclododecane-N,N', N",N'"-tetraacetic acid (DOTA), 1,4,7,10-tetracyclododecane-N,N',N",-triacetic acid (DO3A), 3,6,9-triaza-12-oxa-3,6,9-tricarboxymethylene-10-carboxy-13-phenyl-tridecanoic acid (B-19036), hydroxybenzylethylenediamine diacetic acid (HBED), N,N'-bis(pyridoxyl-5-phosphate)ethylene diamine-N,N'-diacetate (DPDP), 1,4,7-triazacyclononane-N,N',N"-triacetic acid (NOTA), 1,4,8,11-tetraazacyclotetradecane-N, N',N",N'"-tetraacetic acid (TETA), kryptands (macrocyclic complexes), and desferrioxamine. More preferably, the chelating agents are EDTA, DTPA, DOTA, DO3A and kryptands, most preferably DTPA. Preferable lipophilic chelates include alkylated derivatives of the chelating agents EDTA, DOTA, for example, N,N'-bis-(carboxydecylamidomethyl-N-2,3-dihydroxypropyl)-ethylenediamine-N,N'-diacetate (EDTA-DDP); N,N'-bis-(carboxyoctadecylamido-methyl-N-2,3-dihydroxypropyl) ethylenediamine-N,N'-diacetate (EDTA-ODP); N,N'-bis (carboxylaurylamidomethyl-N-2,3-dihydroxypropyl) ethylenediame-N,N'-diacetate (EDTA-LDP); and the like. Preferable proteinaceous macromolecules include, for example, albumin, collagen, polyarginine, polylysine, polyhistidine, gamma-globulin and beta-globulin, with albumin, polyarginine, polylysine, and polyhistidine being more preferred.

Suitable chelating complexes that may be incorporated as linkers in the compounds of the invention therefore include Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cr(III)-

EDTA, Y(III)-DTPA, Y(III)-DOTA, Y(III)-DO3A, Y(III)-kryptands, Y(III)-TMT or iron-desferroxamine, especially Mn(II)-DTPA, Y(III)-TMT or Gd(III)-DTPA.

In another embodiment of the invention, the linking groups of this invention can comprise a group that contains a metal ion such as, for example, a metal ion chelating group. The term 'metal ion' as used herein is intended to include any ion of an element other than hydrogen that has an oxidation state equal to or greater than 1 and which can bind to a chelating agent as a linking group of this invention through interaction with sites of high electron density in the chelating agent such as at heteroatom sites. The interaction of the metal ion with sites of high electron density in the chelating agent can be in the form of a Lewis acid-base interaction, wherein the oxidation state of metal ion is stabilized by interaction with donated electron density from sites of high electron density of the chelating agent. A metal ion can also interact with sites of high electron density in a chelating agent to form a salt in the form of an ionic association between a positively charged metal ion such as a lanthanide ion or a yttrium ion and a negatively charged substituent on the chelating agent such as a carboxylate anion substituent. A metal ion can also interact with sites of high electron density in the chelating agent to form a covalent bond between the metal which has an oxidation state equal to or greater than 1 such as rhenium or technetium and a heteroatom of the chelating agent such as a sulfur or nitrogen or oxygen atom.

Metal ions can be easily complexed to the chelating agent in the linking group, for example, by merely exposing or mixing an aqueous solution containing the chelating agent in the linking group with a metal salt, preferably in an aqueous solution. Preferably such solution has a pH in the range of about 4 to about 11. The metal ion salt can be any composition containing the metal ion including compositions that contain organic acids, organic acid ions, and chelating agents such as acetic acid, acetate ion, salicylic acid, salicyalate ion, citric acid, citrate ion, oxalic acid, oxalate ion, acetylacetone, acetylacetonate ion, amino acid and amino acid ion containing solutions such as glutamic acid and aspartic acid solutions, and solutions of iminodiacetic acid, ethylenediaminetetraacetic acid and related compounds. Salts with a low water solubility (i.e., a metal salt such as lead sulfide or yttrium phosphate that has a large solubility product or low water solubility in the absence of a solubilizing agent such as a chelating agent) are useful, but preferably the salt is a water soluble salt of the metal such as, for example, a halogen or nitrate salt such as europium chloride or yttrium chloride or copper nitrate. More preferably such salts are selected so as not to interfere with the binding of the metal ion to the chelating agent in the linking group. Such interference may occur, for example, as the result of removal of the ion from solution by precipitation. This would result in a slower rate of binding of the desired metal ion to the chelating agent in the linking group with respect to the rate that can occur in the presence of a soluble salt. The chelating agent in the linking group is preferably in aqueous solution at a pH of between about 5 and about 9, more preferably between pH about 6 to about 8. The chelating agent can be mixed with buffer salts such as citrate, acetate, phosphate and borate to produce the optimum pH. Preferably, said buffer salts are selected so as not to interfere with the subsequent binding of the metal ion to the chelating agent in the linking group as described above. Presently preferred buffered aqueous solutions comprise sodium acetate plus acetic acid in water as well as citric acid plus sodium citrate in water. Presently preferred metal ions are $In^{+3}$, $Eu^{+3}$, $Gd^{+3}$, and $Y^{+3}$, and a presently preferred metal ion salts are $InCl_3$, $EuCl_3$, $GdCl_3$, and $YCl_3$.

In another embodiment, the ions, $M_1$ and $M_2$, of two separate elements can be chelated simultaneously to chelating agents in the linking groups of this invention. This can be done by a process comprising the sequential exposure of said chelating agent to a solution 1 containing metal ion $M_1$ as described above for an effective time to allow the complexation of some or all of $M_1$ by the chelating agent in the linking group, followed by the optional removal of excess amounts of metal ion, $M_1$, from the vicinity of the chelating agent in the linking group (for example, by precipitation and filtration), followed by subsequent exposure of the chelated $M_1$ species in the linking group thus formed to a solution 2 containing a second metal ion, $M_2$, for a time and under conditions comprising buffer and pH as described above sufficient to permit the formation of a chelate of $M_1$ and $M_2$. Preferably, the molar amount of ion $M_1$ in solution 1 is equal to or less than the molar amount of the dye polymers of this invention, and the molar amount of ion $M_2$ in solution 2 can be less than, equal to, or greater than the molar amount of the chelating agent of this invention complexed to $M_1$. More preferably, the molar amount of ion $M_2$ in solution 2 is less than or equal to the molar amount of the dye polymers of this invention complexed to $M_1$. A preferred amount of time for the formation of a metal complex is in the range from about one second to about two hours, preferably from 15 seconds to one hour, and more preferably from about 1 minute to about 20 minutes.

In another embodiment, the ions, $M_1$ and $M_2$, of two separate elements can be chelated sequentially to chelating agents in the linking groups of this invention. This can be by a process comprising the sequential exposure of said chelating agent to a solution 1 containing metal ion $M_1$ as described above for an effective time to allow the complexation of some or all of $M_1$ by the chelating agent, followed by the optional removal of excess amounts of metal ion, $M_1$, such as by precipitation and filtration from the vicinity of the chelating agent, followed by subsequent exposure of the chelated $M_1$ species thus formed to a solution 2 containing a second metal ion, $M_2$, for a time and under conditions comprising buffer and pH as described above sufficient to permit the formation of a chelate of $M_2$. In addition to ions of alkali metals such as sodium, potassium, and cesium, and to ions of alkaline earth metals such as magnesium, calcium, and barium, preferred metal ions can be selected from, but are not limited to, ions of elements of groups IIA through VIA. Preferred metals include those of atomic number 12, 13, 20, the transition elements 21 to 33, 38 to 52, 56, 72 to 84 and 88 and those of the lanthanide series (atomic number 57 to 71 sometimes hereinafter referred to as the lanthanide metals). Ions of yttrium and the lanthanide metals are especially preferred.

In another embodiment, the metal chelate in the linking group of this invention can comprise a fluorescent metal ion. The fluorescent metal ion can be selected from, but is not limited to, metals of atomic number 57 to 71. Ions of the following metals are preferred: La, Ce, Pr, Nd, Pm, Sm, Eu, Gd, Tb, Dy, Ho, Er, Tm, Yb, and Lu. $Gd^{+3}$ and $Eu^{+3}$ ions are especially preferred.

Fluorescent metal ion complexes of chelating groups in the linking groups of this invention such as, for example, a $Eu^{+3}$ ion chelate, can exhibit utility in time delayed fluorescence and assays which involve time delayed fluorescence such as in the detection of fluorescent metal ions such as $Eu^{+3}$. In such an assay, a compound of this invention comprising a chelating agent in a linking group is exposed to a material such as a solution that contains a fluorescent metal ion such as $Eu^{+3}$ ion for an effective amount of time so that a complex is formed between the chelating agent and the $Eu^{+3}$ ion. A preferred amount of time is from about one second to one hour, preferably from 15 seconds to 10 minutes. The complex is subsequently irradiated with an excitation light such as, for example, a pulse of light having a maximum intensity at a wavelength of about 385 nanometers. The excitation light pulse is then stopped or blocked from further access to the metal complex, an effective time such as about 400 microseconds is allowed to elapse, and emission of light is then detected and measured with a detector capable of determining intensity of light as a function of wavelength. The wavelength of the emitted light is longer than the wavelength of the excitation light. The effective time delay is preferably about 400 microseconds or longer so that no interference for ambient fluorescent emitters interferes with the detection of the desired fluorescence in this type of assay. A preferred composition for this type of assay comprises linking group such as an oligo-2,6-pyridine chelating agent substituted with iminodiacetic acid groups and chelated to a $Eu^{+3}$ ion.

In another embodiment, a metal chelate in the linker moieties in the compounds of this invention can comprise a paramagnetic ion which is suitable for the use in nuclear magnetic resonance applications which include in vitro and in vivo diagnostic imaging such as of animal and human tissue using MRI techniques as well as in applications such as in nuclear magnetic resonance chemical shift reagents. The paramagnetic ion is an ion of an element which can be selected from elements of atomic number 21 to 29, 43, 44 and 57 to 71. The following elements are preferred: Cr, V, Mn, Fe, Co, Ni, Cu, La, Ce, Pr, Nd, Pm, Sm, Eu, Gd, Tb, Dy, Ho, Er, Tm, Yb and Lu. Mn, Gd, and Dy are especially preferred. $Gd^{+3}$ and $Dy^{+3}$ are especially preferred ions. The chelation of one metal ion with each chelating agent in the linking group is useful in this regard. Such a metal chelate can be formed as described above.

In another embodiment, a metal chelate in the linker moieties in the compounds of this invention can comprise a radionuclide. The radionuclide can be selected, for example, from radioisotopes of Sc, Fe, Pb, Ga, Y, Bi, Mn, Cu, Cr, Zn, Ge, Mo, Tc, Ru, In, Sn, Sr, Sm, Lu, Sb, W, Re, Po, Ta and Tl. Preferred radionuclides include $^{44}SC$, $^{64}CU$, $^{67}CU$, $^{111}In$, $^{212}Pb$, $^{68}Ga$, $^{90}Y$, $^{87}Y$, $^{153}Sm$, $^{212}Bi$, $^{99m}Tc$, $^{186}Re$ and $^{188}Re$. Of these, especially preferred is $^{90}Y$.

In some applications, a mixture of metal ions such as sodium ions and yttrium ions is useful. For example, solution of a metal chelate of this invention in a sodium acetate buffer can be treated with a less than stoichiometric quantity of a radionuclide such as $^{90}Y$, and after an effective time during which chelation of substantially all of the radionuclide occurs, the subsequent mixture containing $^{90}Y$ bound to metal chelate plus the sodium salt of non-$^{90}Y$-containing metal chelate can be useful without further separation of the individual components, for example, in radioscintigraphy analysis of proteins separated by electrophoresis or for solubilizing radionuclides such as $^{90}Y$ in the presence of ions such as phosphate ions that would otherwise combine with the metal ion to form a precipitate such as yttrium phosphate. In the bulk, a solution of the metal chelate plus non-radionuclide containing chelating agent in a linking group of this embodiment of this invention preferably contains a ratio of metal radionuclide ion to total amount of chelating agent that is effective in such applications. In preferred embodiments, the mole ratio of such metal ion per chelating agent in a bulk solution is from about 1:1000 to about 1:1.

The contrast agent compounds used according to the invention may be administered by any convenient route, for example by injection or infusion into muscle, tumor tissue, or the vasculature, subcutaneously, or interstitially, by administration into an externally voiding body cavity (e.g., into the digestive tract (for example orally or rectally), vagina, uterus, bladder, ears, nose or lungs), by transdermal administration (e.g., by iontophoresis or by topical application), or by topical application to a surgically exposed site.

In general, parenteral administration, eg of a solution or dispersion of or containing the chromophore compound, will be preferred.

The administration forms used may be any of the forms conventionally used for administration of pharmaceuticals, e.g., solutions, suspensions, dispersions, syrups, powders, tablets, capsules, sprays, creams, gels, etc.

The contrast agent compounds, if water-soluble, can be administered in the form of an aqueous solution. Alternatively, and in many cases preferably, the contrast agent compounds may be presented in particulate form, e.g. liquid droplets of or containing the contrast agent (e.g., in solution in a water-immiscible fluid), or solid or semi-solid particles of, containing or coated with the contrast agent. This latter category includes vesicles (e.g., liposomes, micelles or microballoons) containing the contrast agent compound.

Because of their intrinsic light scattering effect, particles are a presentation form for the contrast agent. Particle sizes may range from a few nanometers to about 20 micrometers, e.g. 10 to 5000 nm. However the larger particle sizes (above 10 micrometers) will generally only be used with deformable particles.

Where the particles contain other components besides the contrast agent compound, e.g., matrix or membrane forming materials, coating agents, solvents, gases or gas generators, etc, these will conveniently be materials which are physiologically tolerable at the dosages used. The formation of droplets, coated particles, composite particles, vesicles, etc is well described in the literature, especially that relating to pharmaceutical and contrast agent (e.g., ultrasound contrast agent) preparation and formulation.

Where a water-soluble contrast agent is to be used to mark tumors for surgical removal, then it may be preferred to administer the agent in particle form in order to reduce staining of, and hence removal of, healthy tissue surrounding the tumor. Indeed in place of conventional water-soluble chromophores such as methylene blue, it may be desirable to use derivatised analogs, where derivatisation has been to introduce lipophilic groups which will reduce leakage of the chromophore from the particle, e.g., an emulsion droplet or a liposome. For this purpose, one may use long chain hydrophobic groups, such as $C_{10-30}$ alkyl or alkenyl chains, preferably groups of a similar length to the lipophilic component of any liposome membrane forming material that is present in the particle. This type of chromophore derivatization can be made for any chromophore, in particular charged chromophores, especially thiazine chromophores such as methylene blue.

Thus while many of the contrast agent compounds described herein are water soluble and can therefore be administered by injection, they can also be incorporated into liposomes and injected in this form.

Alternatively, these contrast agent compounds may be administered via the oral route for absorption through the lining of the stomach, the intestines, and the colon, see for example, Carrier-mediated intestinal transport of drugs, Tsuji, A.; Tamai, I., Pharmaceutical Research (New York) Vol. 13, No. 7, p. 963–977, 1996; Oral protein drug delivery, Wang, Wei, J. Drug Targeting Vol. 4, No. 4, 1996, pp. 195–232; Improved passive oral drug delivery via prodrugs, Taylor, Michael D., Adv. Drug Delivery Rev. Vol. 19, No. 2, 1996, pp. 131–148; Oral colon-specific drug delivery: a review, Van den Mooter, Guy; Kinget, Renaat, Drug Delivery, Vol. 2, No. 2, 1995, pp. 81–93; Present status of controlled drug delivery system-overview, Naik, S. R.; Shanbhag, V., Indian Drugs, Vol. 30, Sepetember 1993, pp. 423–429; Novel formulation strategies for improving "oral" bioavailability of drugs with poor membrane permeation or presystemic metabolism, Aungst, B. J., Journal of Pharmaceutical Sciences (USA), Vol. 82, No. October 1993, pp. 979–987; Remington's Pharmaceutical Sciences, A. Osol, ed., Mack Publishing Co. 1975, Part 6, chp 40 and references therein. (pp 731–753), Part 8, all chps (pp 1355–1644); The Extra Pharmacopoeia, Martindale, 29th Edition, The Pharmaceutical Press, London, 1989.

Administration of drugs and other agents by this route is often preferred due to enhanced patient compliance (for repeated dosing) and ease of administration. It is well known in the art that not every agent is bioavailable via this route; that is to say, that not all molecules are 1) chemically stable in the environs of the gut, 2) transportable across alimentary membranes for absorption into the blood/lymphatics, and 3) active even if accessible due to metabolic processes within the gut or possible solubility issues, etc. However, it is also known in the art, that alteration of the molecular structure to control the relative hydrophobicity of the molecule (i.e., partition coefficient between octanol and water; $\log(P)$) within a preferred range can increase the oral availability of the agent.

These agents can also be administered via body cavities such as the mouth, the rectum, the vagina, the peritoneal cavity (i.e., intraperitoneal injection), etc. as well as topical, intramuscular, subcutaneous, and pulmonary administration. All of the known routes of administration of drugs/agents to mammals are envisaged according to the present invention.

The contrast agent can be injected into the vasculature prior to or during surgery. For detection of lymph nodes it can be injected into a lymph duct draining into the surgical area. Alternatively it may be applied during surgery as a topical ointment, a liquid, or a spray.

For dermatological applications, the contrast agents described in WO 96/23524 may be modified to be delivered through transdermal patches or by iontophoresis. Iontophoretic delivery is preferred, as one can control the amount of the agent that is delivered.

The compounds of the invention may be administered to patients for imaging in amounts sufficient to be visualizable or to be effective in photodynamic therapy (PDT) or sonodynamic therapy (SDT) in the particular surgical technique.

The dosage of the chromophore compounds of the invention will depend upon the condition being treated, but in general will be of the order of from 1 pmol/kg to 1 mmol/kg bodyweight.

The compounds of the present invention may be formulated with conventional pharmaceutical or veterinary aids, for example emulsifiers, fatty acid esters, gelling agents, stabilizers, antioxidants, osmolality adjusting agents, buffers, pH adjusting agents, etc., and may be in a form suitable for parenteral or enteral administration, for example injection or infusion or administration directly into a body cavity having an external escape duct, for example the gastrointestinal tract, the bladder or the uterus. Thus the compounds of the present invention may be in conventional pharmaceutical administration forms such as tablets, capsules, powders, solutions, suspensions, dispersions, syrups, suppositories etc. However, solutions, suspensions and dispersions in physiologically acceptable carrier media, for example water for injections, will generally be preferred.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

For some portions of the body, the most preferred mode for administering the compounds of the invention is parenteral, e.g., intravenous administration. Parenterally administrable forms, e.g. intravenous solutions or dispersions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions or dispersions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions or dispersions can contain preservatives, antimicrobial agents, buffers and antioxidants conventionally used for parenteral solutions, excipients and other additives which are compatible with the compounds of the invention and which will not interfere with manufacture, storage or use.

The contrast agent compounds of the present invention can be formulated in biologically compatible formulations and administered to humans, intravenously or by other commonly used routes of administration.

While the contrast agent compounds of the invention are particularly suited to intraoperative and post-surgical PDT and SDT use to facilitate visualization of tumor margins and optimize the surgical removal and PDT and SDT destruction of tumor tissues and cells, they can also be used as contrast agents in light imaging of tumor tissue, tumor cells and diseased lymph nodes. The light imaging technique may involve recording a photographic image of a tissue or organ surface illuminated with a light source that causes the contrast agent to exert a contrast enhancing effect and make the unhealthy tissue stand out more clearly from the surrounding healthy tissue, eg due to characteristic light absorption or fluorescence by the contrast agent. Such a photographic image may be recorded of an exposed surface (eg exposed during surgery) or may be recorded by insertion of an endoscope into a body cavity through a body orifice or through a surgical incision.

Alternatively, images may be recorded of light (generally laser light, especially at near infrared wavelengths) scattering from or transmitting through body tissue.

A preferred method for the use of scattered or reflected light in the generation of imaging is diffusive wave imaging, in which the amplitude of the incident light is modulated at an ultrasound frequency and either the amplitude or the phase of the diffusive wave propagating from the point of light injection is measured at one or more incident points. A preferred method for imaging with transmitted light is time-resolved imaging, in which photons that have travelled a relatively straight pathway through the body because they have suffered only a few scattering events or because the scattering events change their direction of propagation only slightly are separated from the highly scattered photons on the basis of their time of arrival at the detection spot. Also preferred are methods in which the incident light is highly polarised and the photons arriving at the detector after having suffered relatively few scattering events are separated from the highly scattered light on the basis of their residual polarisation.

In these techniques, the use of a contrast agent facilitates detection and location of subsurface structures, eg tumors.

Images may also be recorded with hybrid methods involving various combinations of incident or detected light with incident or detected light of a different type. Techniques of this type include magnetic resonance imaging (MRI) guided light imaging, photoacoustic imaging and acoustooptic imaging. In some cases such as MRI guided imaging the hybrid method may simply involve coregistration of imaging and functional information obtained by the two techniques separately. One of the advantages of coregistration of information is that it can allow the extraction of chemical and physical information from a specific body with light while retaining the inherent resolution of the secondary imaging method. In other cases the hybrid method may inherently depend on the interplay of two different types of radiation within the body for generation of an image.

Photoacoustic imaging involves the use of any type of radiation for creation of a medical image when a sound or pressure wave that is generated by absorption of the incident radiation is detected. The imaging is primarily a consequence of how the radiation is absorbed and converted into heat. The sound or pressure wave serves as a "messenger" that reveals how the radiation absorption took place. A contrast agent for photoacoustic imaging works by selectively absorbing radiation in certain organs, or parts of organs, and efficiently converting that radiation into pressure waves or by scattering and diffusing the incipient light so that it more uniformly illuminates the target organs. The radiation may be electromagnetic radiation in the visible, infrared, microwave or other parts of the electromagnetic spectrum.

Acoustooptic imaging is a modified approach to optical imaging in which focused ultrasound is used to isolate optical signals from the body. The method derives from the phenomenon of Brillouin scattering of light by sound waves, which has been known for many years. Brillouin scattering involves the constructive interference among the components of a beam of light passing through the moving wavefronts of a sound wave. In effect, the acoustic wave sets up moving regions of different pressure, density, and refractive index that interact with the light in much the same manner as a diffraction grating. The movement of the sound waves further induces a Doppler shift of the sound frequency into the light frequency.

When focused ultrasound is used as a component of optical imaging, the sound introduces fluctuations into the optical properties of the light passing through the target organ that differentiate it from the general background of light passing through the body as a whole. Although a photomultiplier tube or other detector on the surface of the body will pick up both scattered light that has followed many courses through the body and the signal from light that has actually passed through the region of interest, the signal from the region of interest can be separated from all other light by the fact that it is modulated at the frequency of the focused ultrasound.

Acoustooptic imaging actually expands the ability of optical imaging to provide functional information since the degree to which the focused sound waves interact with the diffuse light will depend on the mechanical properties of the body at the sight of the sound focusing. The ability to measure tensile modulus and other mechanical properties of a suspicious lesion greatly facilitates identification of the lesion as malignant or benign. Contrast agents that enhance the degree to which the signal of light that has been modified by the ultrasound will have particular value in improving the degree to which this information can be extracted.

Other light imaging techniques may be used to record contrast enhanced images of shallow subsurface structures, eg within a millimeter of the surface.

Confocal scanning laser microscopy (CSLM) selectively images a single point within a test object by focusing light from a pinhole source onto that point. The light transmitting past or reflecting from that point is then refocused onto a second pinhole that filters out spurious light. Thus the detector behind the pinhole picks up the image of the point alone. Raster scanning of the point through a complete plane passing through the sample with the help of movable mirrors generates the image of a complete plane of points. Thus CSLM is a means for "optically" sectioning a test sample.

Optical coherence tomography (OCT) accomplishes optical sectioning in a related, but somewhat different manner. A collimated beam of light is reflected from the sample, then is compared with a reference beam that has traveled a precisely known distance. Only the light that has traveled exactly the same distance to the sample and back as has the reference beam from the source to the detector constructively interferes with the reference beam and is detected. Thus the light from a single plane within the sample is again selected.

CSLM, OCT, photoacoustic, acousto-optical, diffusive wave, time-resolved imaging, endoscopic, multiphoton excitation microscopy or visual observation techniques are particularly suitable for examination of excised tissue. However, they could also be used for in vivo optical biopsy of suspicious skin lesions and for characterization of body surfaces that can be exposed endoscopically or surgically.

It is anticipated that CSLM, OCT or other forms of in-vivo microscopy will be especially useful in optically guided tumor resection or destruction. For example, either device attached to a colonoscope will facilitate determination of the appropriate depth to which a malignant colon polyp should be excised to ensure complete removal of cancerous tissue. Additional applications include, but are not limited to, diagnosis and treatment of disease conditions of the rest of the digestive tract, surgical treatment of ulcerative colitis, and diagnosis and treatment of endometriosis.

When either CSLM or OCT is used as a dermatological tool, scattering from melanosomes in the skin is believed to be responsible for producing contrast. The primary effect of these sites is to scatter or reflect light hitting them. Synthetic contrast agents can act either as scattering or absorbing agents.

A preferred contrast agent for intraoperative CSLM, OCT, photoacoustic, acousto-optical, diffusive wave, time-resolved imaging, endoscopic, multiphoton excitation microscopy or visual observation techniques will have the following properties: it will consist of stabilized particles in aqueous or buffered solution. The particle size may be around 300 to 1300 nm (i.e., roughly equal to the wavelength of the light source). The refractive index of the particles will differ from that of body fluids such as blood and lymph by at least 0.01. The particles may be made of a chromophore polymer compound or may contain or be coated with a chromophore polymer compound, e.g., the particles may comprise a matrix material (e.g. a physiologically tolerable synthetic or non-synthetic polymer, such as an acrylate or polysaccharide) incorporating a chromophore polymer compound, a core of a chromophore polymer compound coated with a coating agent or encapsulated by a membrane forming material, or a core of a matrix material with a chromophore polymer compound coated on or attached to the particle surface. The particles may be solid, semi-solid or liquid and may be layered structures such as vesicles (e.g., micelles, liposomes and microballoons). The chromophore polymer compound used will preferably be a fluorescent material, particularly a material having an emission maximum in the near infrared range, especially in the range 650 to 900 nm. Optionally the particles may have suitable surface modifying agents, such as poly(ethylene glycol) to slow their uptake by macrophages in the body. Examples of suitable particulate agents are described in WO 96/23524. Optionally, the particles can be cells coated with the polymers of this invention. These coated cells can be formed in the body with injected agents or externally from cells extracted from the body and then injected into the body.

The chromophore compounds to be used as contrast agents in methods of light imaging according to the invention, e.g., in conjunction with CSLM, OCT or other forms of in-vivo microscopy may also be polymeric or monomeric water-soluble chromophores, e.g., as described herein.

In some situations the resolution of in vivo CSLM, OCT or other forms of in-vivo microscopy may be high enough to allow the separation of the images of the nuclei and cytoplasm of individual cells. A contrast agent that specifically localizes in the nucleus or the cytoplasm of cells will increase the contrast between these sites and that of the background. Agents for this purpose will be non-toxic forms of staining chromophores already used for histological examination of excised tissue. A list of such selectively staining chromophores can be found in any handbook of histological stains.

The perfusion of tissue that is exposed by surgery is one important indicator of the health of that tissue. One of the indicators of the degree of perfusion is the rate of blood flow within the tissue. Blood flow in the skin can be detected by laser Doppler blood-flow measurement or laser speckle interferometry, either by itself or in conjunction with CSLM, OCT or other forms of in-vivo microscopy.

Laser Doppler and speckle interferometry are related, and each relies upon the fact that the intensity of light detected after a beam of laser light that interacts with a collection of moving particles changes with time (Ruth, B., "Blood Flow Determination by the Laser Speckle Method," *Int. J. Microcirc.: Clin. Exp.*, 1990, 9, 21–45). Mathematical analysis of the changes provides a basis for calculating the rate at which the particles are moving.

When laser light with a wavelength between 600 and 1200 nm is reflected from the skin, the necessary changing pattern of light reflecting back to a light detector results largely from movement of blood cells within the dermis. However, speckle interferometry is best suited for determination of blood flow in vessels with diameters between 0.08 and 1 mm. Laser Doppler measurement is best used for blood vessels 0.08 mm and possibly smaller in size (Ul'Yanov, S. S.; Tuchin; Bednow; Brill, G. E.; Zakharova, E. I., "The Application of Speckle Interferometry for the Monitoring of Blood and Lymph Flow in Microvessels", *Lasers in Medical Science*, 1996, 11, 97–107). Light reflected from larger vessels, which lie deep within the dermis and in the underlying tissue, only serves to complicate the analysis of the light from the smaller vessels lying about 0.5 mm beneath the surface of the skin (Abbot, N. C.; Ferrell, W. R.; Lockhart, J. C.; Lowe, J. G., "Laser Doppler Perfusion Imaging of Skin Blood Flow Using Red and Near-Infrared Sources", *J. Invest. Dermatol.*, 1996, 107, 882–886).

When the vasculature contains an absorbing chromophore, Beer's law shows that light passing through larger blood vessels will be more strongly attenuated than is light passing through smaller vessels. Furthermore, light scattering from blood cells in vessels deep within the skin and underlying tissue will be more attenuated than will light scattering from blood cells in vessels near the surface of the skin. Thus, the presence in the blood of a contrast agent with an absorption maximum near the wavelength of the laser light used for either Doppler or speckle interferometric measurements of blood flow improves the selectivity of the measurement for smaller vessels near the skin surface. An agent of the type taught by this invention is necessary as there must be a stable concentration of the agent in the blood over the course of the invention.

Diagnostically useful images can be obtained after administration using endoscopic imaging, confocal microscope imaging, time delayed fluorescence imaging, phase modulation imaging, photoacoustic imaging, or other imaging technique.

In any of the above oligomers and Chr-PAO-Chr structures, groups that bind to biological receptors can be incorporated, for example, at pendant and/or at terminal amine groups and carboxyl groups. These groups can be used to "target" the Chr-(PAO-Chr)$_n$ imaging agents to receptor sites on tissues.

Therapeutic application using these compounds can be achieved in the form of cytotoxic application of light in the form of photodynamic therapy wherein the tissues to be treated or destroyed are treated first with contrast agents which are allowed to intimately associate with the tissue and then by irradiation with light which is absorbed by the contrast agents in vivo, optionally in the presence of oxygen in the blood or in oxygenated saline solution, or in oxygenated plasma, or oxygenated lymph fluid and the like.

Therapeutic application using these compounds can sometimes be achieved with sonodynamic therapy wherein the tissues to be treated or destroyed are treated first with contrast agents which are allowed to intimately associate with the tissue and then by sonication with high frequency sound such as ultrasound optionally in the presence of oxygen in the blood or in oxygenated saline solution, or in oxygenated plasma, or oxygenated lymph fluid and the like.

All of the publications referred to herein are incorporated herein by reference.

Any mention in the text to the term "mean MW" or "mean molecular weight" refers to a weight average.

The invention will now be described further with reference to the following non-limiting Examples and Figures. In the Examples, the abbreviation Pc is used to refer to phthalocyanine.

Figure 3A:
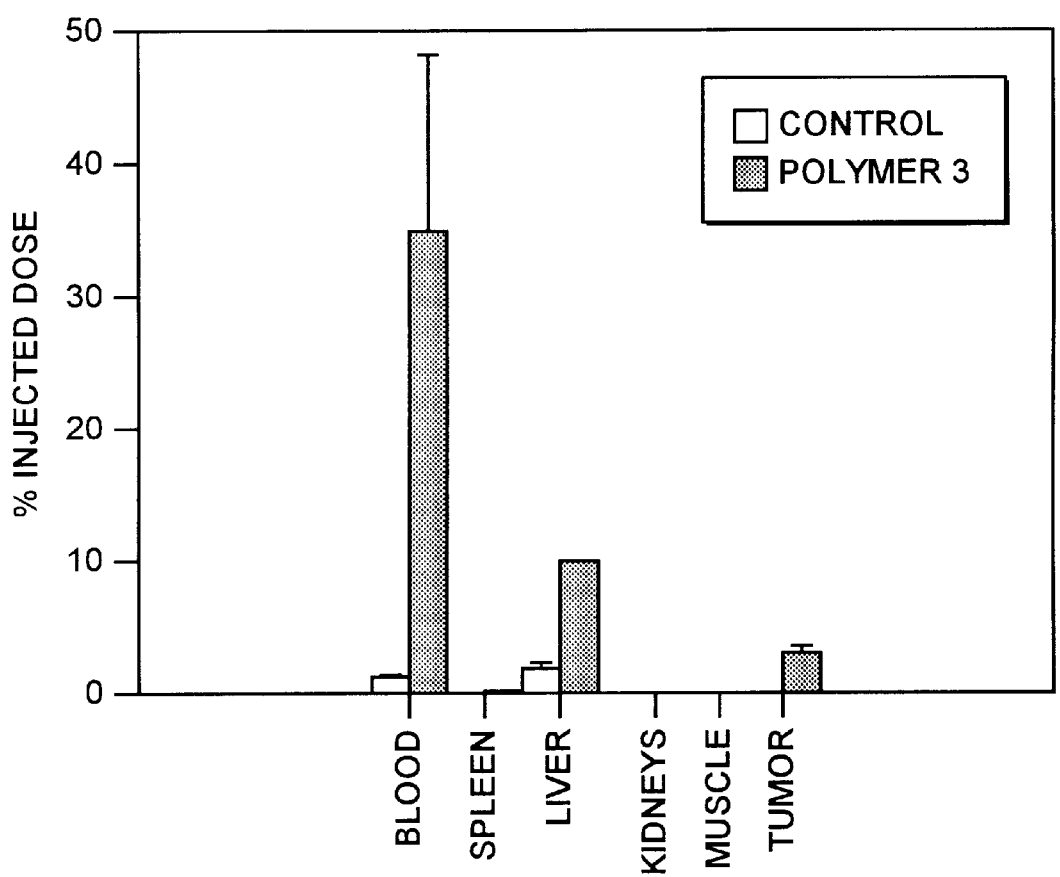
FIG. 3A is a graph of comparative biodistribution data of contrast agent Polymer 3 (NC100448) versus indocyanine green as control in female immunodeficient mice containing HT-29 tumors at one hour post intravenous injection of phosphate buffered saline solutions of each. Polymer 3 is detected in the tumor; the control compound is negligibly detected.
Figure 3B:
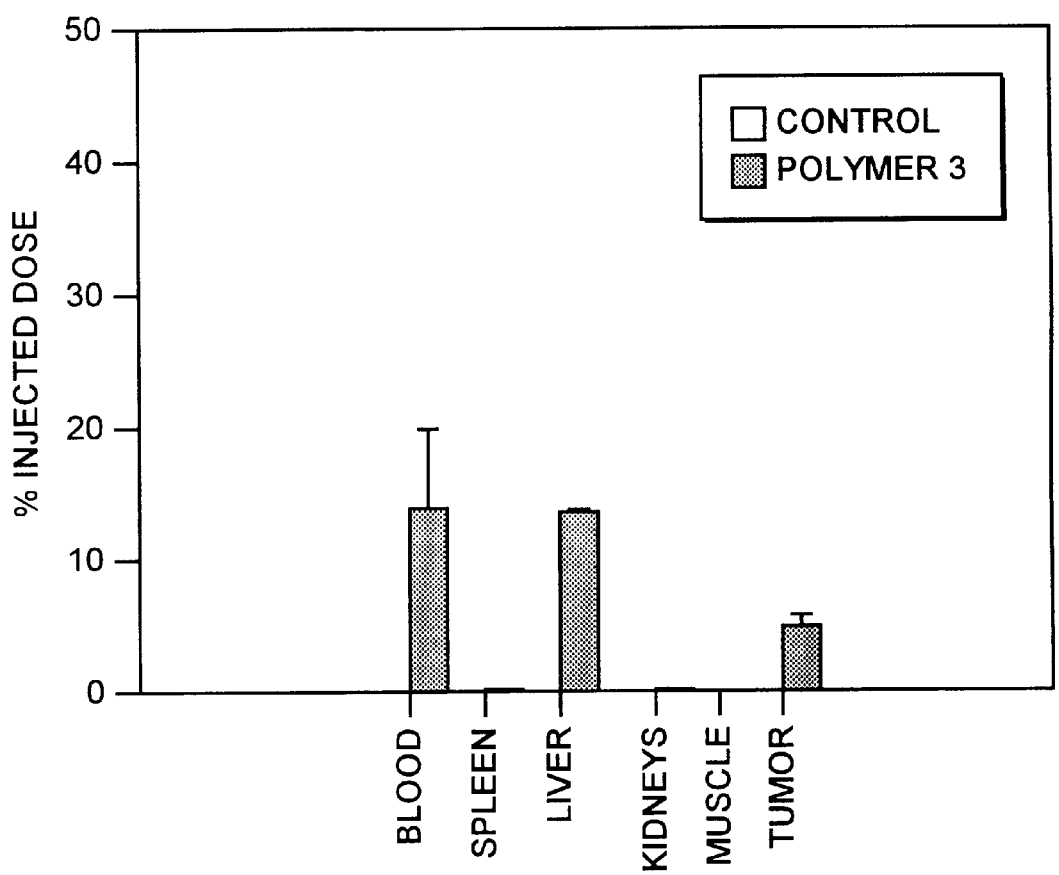

FIG. 3B is a graph of comparative biodistribution data of contrast agent Polymer 3 (NC100448) versus indocyanine green as control in female immunodeficient mice containing HT-29 tumors at three hours post intravenous injection of phosphate buffered saline solutions of each. Polymer 3 is detected in the tumor; the control compound is negligibly detected. Relative to FIG. 3A, the concentration of the contrast agent in the tumor has increased while the concentration in the blood has decreased.

Figure 4:

FIG. 4 is a photograph taken under room fluorescent light of female immunodeficient mice with exposed human HT-29 tumors 24 hours post intravenous (tail vein) injection with 0.1 mg/(g body weight) in PBS of the blue contrast agent NC100526. The labeled sheet to the right of the mice was spotted with PBS solutions of several contrast agents of this invention and then dried in order to show how they appear under various illumination and imaging conditions. The tumors (indicated by arrows) have been sliced to expose their interiors as well as their exteriors. The tumors exhibit a blue color due to the presence of contrast agent, and have areas of darker color due to increased concentrations of contrast agent present along the tumor edges (as indicated by arrows in the black and white photograph) and in some regions of the interior.

Figure 5:
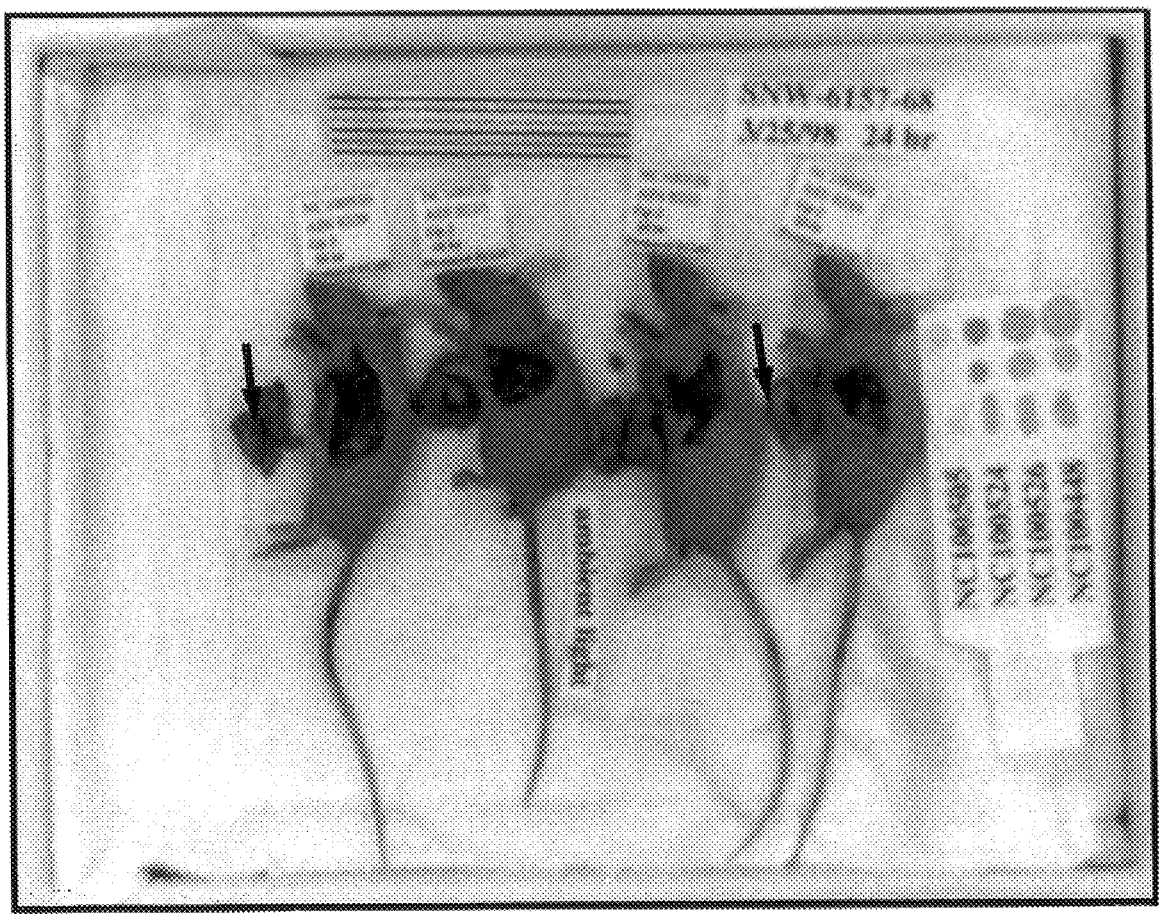

FIG. 5 is a photograph which shows a comparison of tumors surgically removed from mice treated as in FIG. 4 with contrast agent NC100526 versus tissues to which the tumors had been attached. The arrow at the left points to a region of contrast agent detectable within the tumor by its blue color; the arrow at right points to a region of contrast agent detectable by its blue color on the surface of the tumor. The residual tissue had a normal color.

Figure 6:
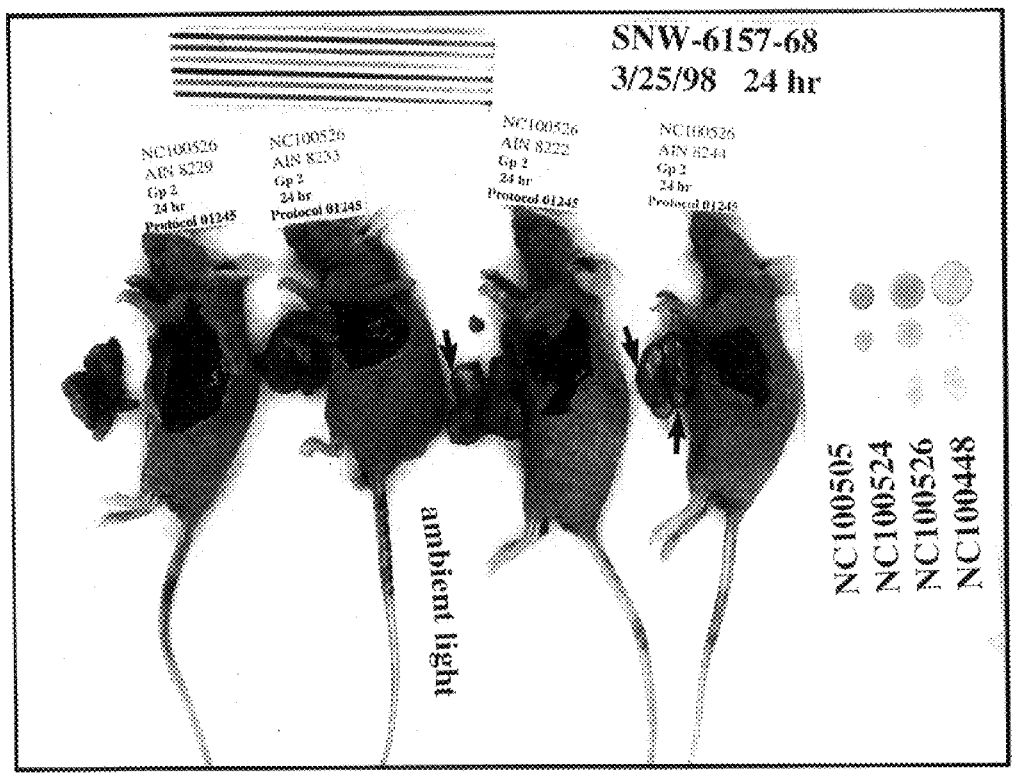

FIG. 6 shows that the contrast created by the presence of contrast agent NC100526 at the outside edge of the tumors pictured in FIGS. 4 and 5 (arrows) is enhanced when the image is recorded with Kodak high-speed black and white infrared film. The light source was ambient fluorescent room light.

Figure 7:
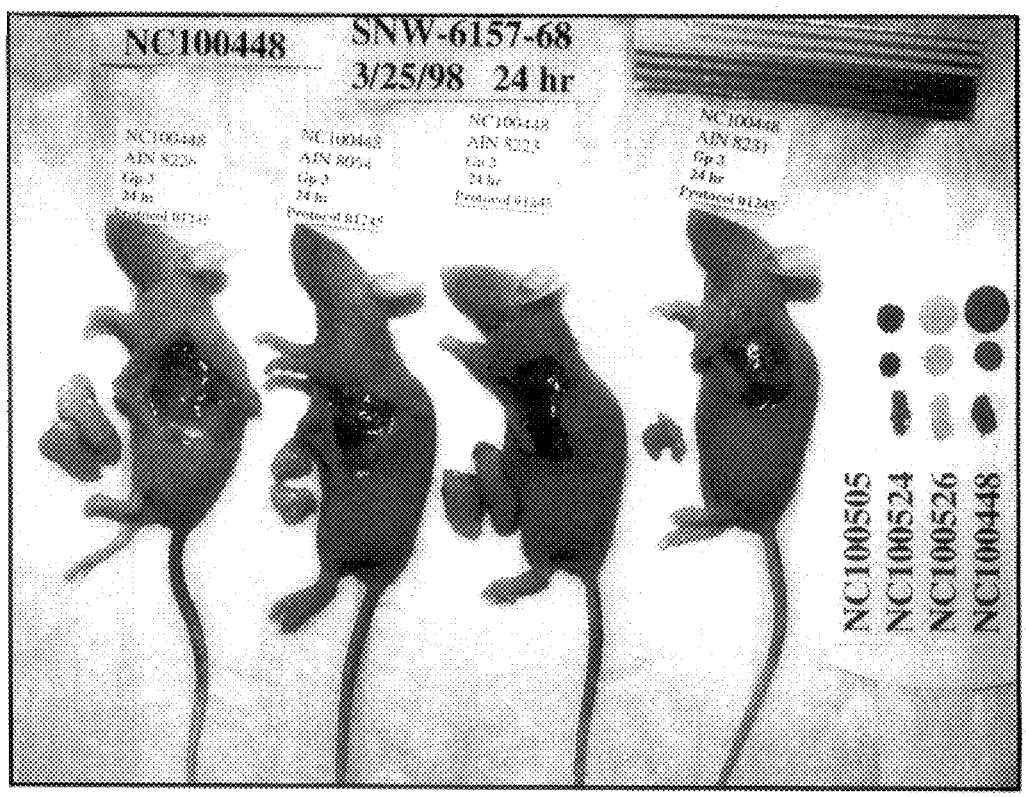

FIG. 7 shows a comparison image of tumors taken from mice 24 hours after they were injected with 0.05 mg/(g body weight) of the infrared contrast agent NC100448 in PBS. The photograph was taken with black-and-white infrared film using irradiation at 780 nm from an array of light-emitting diodes. These conditions gave maximum absorption and contrast enhancement of NC100448 as evidenced by the darkened spot of contrast agent on the paper chart. The tumors appear uniformly darker than control tumors (not shown), but do not show darkening around the edges as seen in tumors from mice injected with NC100526 (FIG. 4). Measured biodistribution of the contrast agent in the mice (see Table 1) shows that the tumors contain NC100448.

Table 1 presents biodistribution data at 3, 6, and 24 hours, reported as percent injected dose of the contrast agent per gram of tissue, from a separate experiment of mice intravenously injected with contrast agent NC100448 at 0.05 mg/(g body weight) in PBS. At 24 hours the concentration of contrast agent in the tumors remained relatively high while the contrast agent had largely cleared from the blood and had not increased in the muscle.

TABLE 1

| NC100448 Biodistribution Data in HT 29 Tumored Mice | | | |
|---|---|---|---|
| | Plasma | Tumor | Muscle |
| 3 hr | 14.33 ± 1.33 | 5.57 ± 0.73 | nd |
| 6 hr | 8.44 ± 1.33 | 8.6 ± 1.53 | nd |
| 24 hr | 0.46 ± 0.40 | 7.53 ± 0.74 | nd | nd = none detected

Figure 8A:
Figure 8B:

FIGS. 8a and 8b are photographs of two views taken from different angles of HT-29 tumors sliced open and removed from mice at 24 hours post injection with 10 mg/(g body weight) of NC100505 in PBS and irradiated with 366 nm wavelength light. The tumors, two of which are indicated by arrows in FIG. 8a, are brightly fluorescent with a yellow color. In the black and white photograph they appear as bright spots. Other organs and the skin appear normal.

Figure 9A:
Figure 9B:

FIGS. 9a and 9b show two photographs of a control mouse with two excised tumors. Under ambient fluorescent room light or 366 nm light the tumors have a color similar to that of the skin.

Figure 10A:
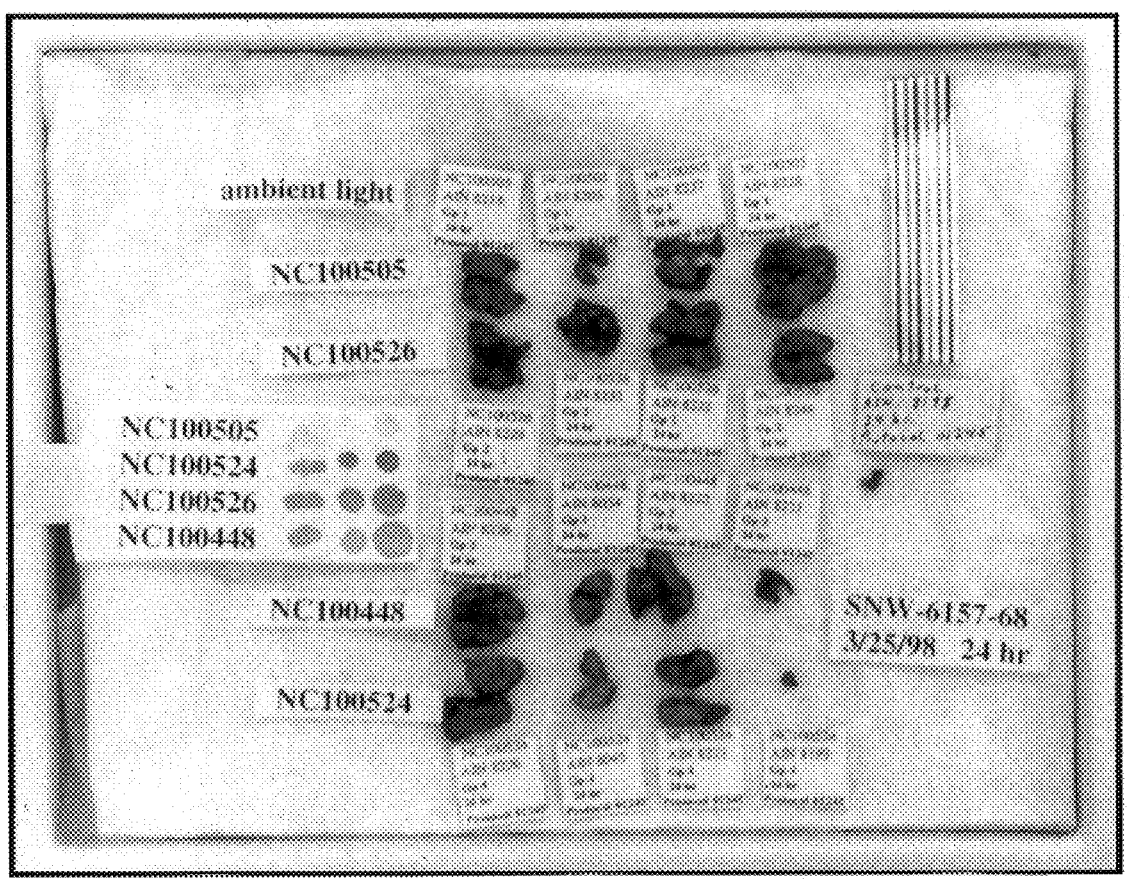

FIG. 10a is a photograph of a collection of excised tumors viewed under ambient fluorescent room light. The top row contains tumors resected from mice at 24 hours post i.v. injection with NC100505 in PBS. The second, third, and fourth rows are tumors resected from mice 24 hours post i.v. injection with PBS solutions of NC100526, NC100448, and NC100524, respectively. At the center to the right is a tumor from the control animal. Under ambient fluorescent room lights the tumors in the second row were clearly blue while the other tumors appeared similar to the control tissue. The shading difference is barely perceptible in the black and white picture shown but the contrast is very distinct in the original color photograph.

Figure 10B:
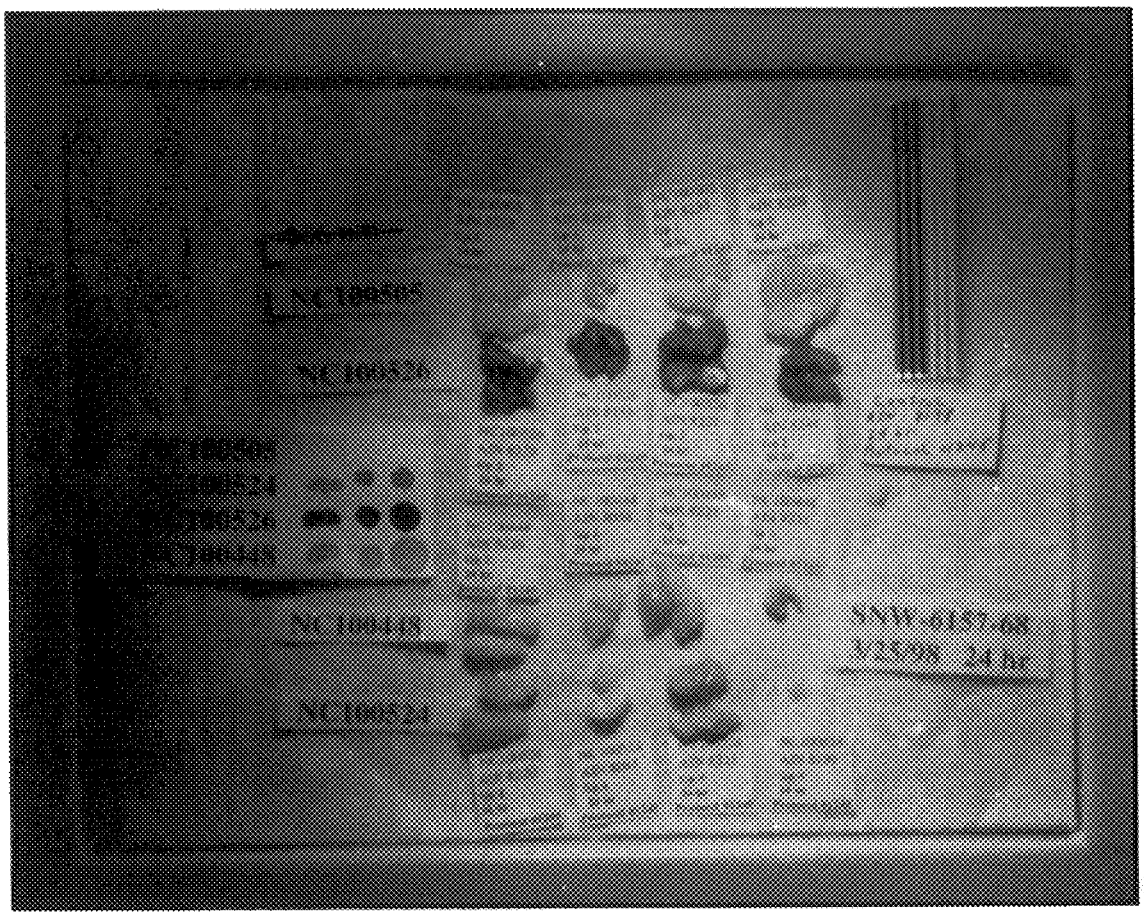

FIG. 10b is a photograph of the same collection of excised tumors as seen in FIG. 10a except that they were irradiated at 680 nm and photographed with Kodak Ektachrome EIR high speed color infrared film. (The label reading 366 nm is in error and has been struck out with an arrow.) Under this incipient light close to the absorption maximum of NC100526, the tumors in the second row from the top clearly appear darker than the other tumors.

Figure 10C:
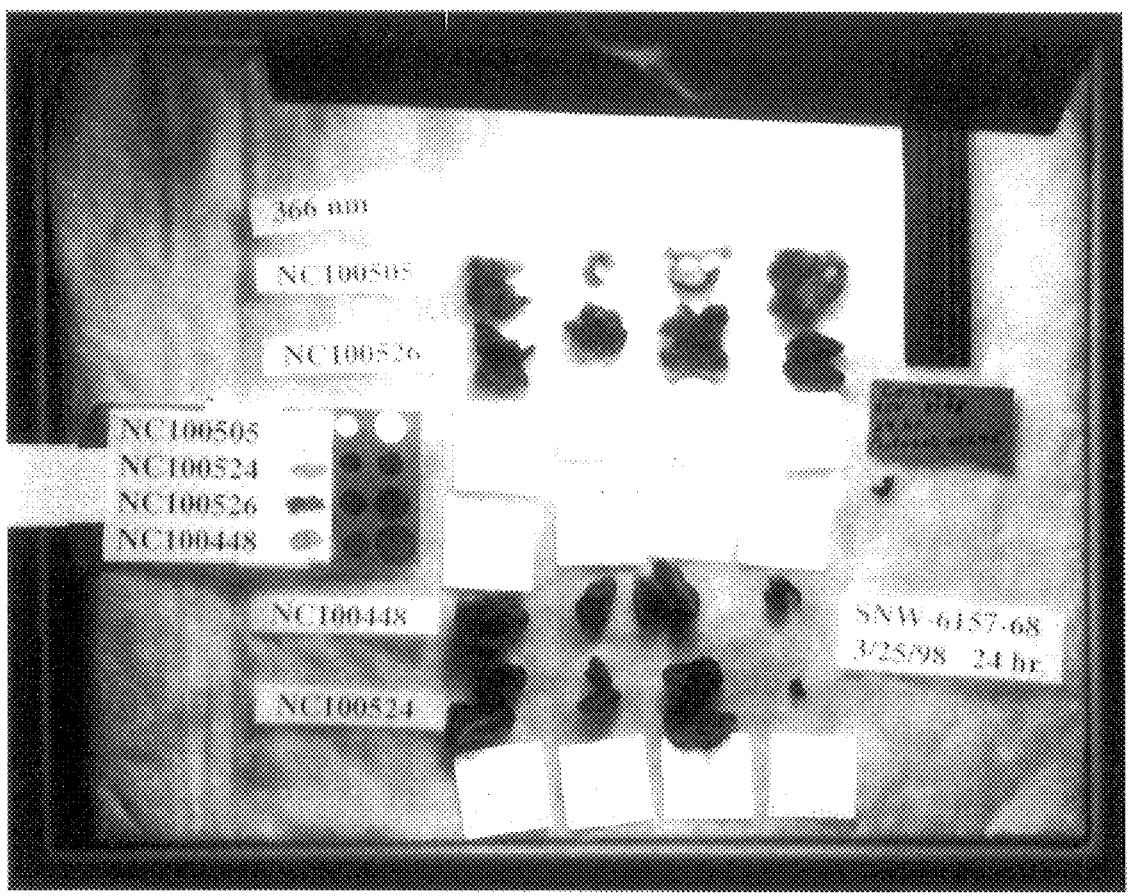

FIG. 10c is a photograph of the same collection of excised tumors as that pictured in FIG. 7 but photographed under irradiation with 366 nm light. The tumors in the top row fluoresced brightly and appeared yellow while the other tumors did not fluoresce under these conditions.

Figure 11:
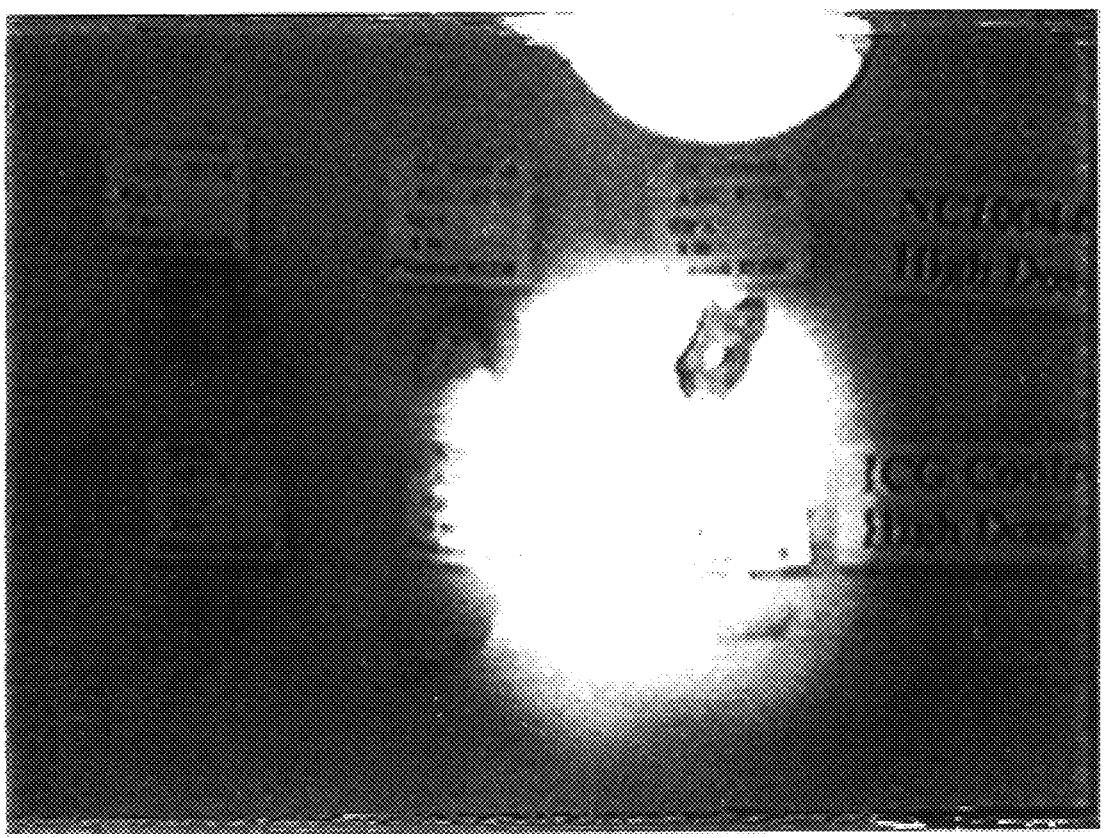

FIG. 11 is a photograph of a set of excised tumors irradiated with 780 nm infrared light that were removed from mice 24 hours post injection with PBS solutions of NC100448 (top row) and indocyanine green (bottom row). The image was recorded with an infrared sensitive CCD camera (Bischke, Type N-CCD-4024, fitted with a Computar TV Zoom lens 1:1.2/12.5–75) on VHS tape (Maxell HGX Plus) at 30 frames/sec using a Panasonic AG-1310P HQ Video Cassette Recorder with super 4-Head VHS SQPB). The tape was digitized and one frame was printed using Adobe Photoshop 4.01. Tumors from mice injected with NC100448 (absorption maximum approximately 780 nm) appeared significantly darker when compared to tumors from mice injected with ICG.

Table 2 shows the biodistribution, reported as percent injected dose of the contrast agent per gram of tissue, at several time points after injection of NC100481 in female immunodeficient mice with HT-29 tumors. Whereas within 24 hours the contrast agent has cleared from both the blood and muscle, it remained at a high concentration in the tumor after 48 hours.

TABLE 2

NC100481 Biodistributions

| | Plasma | Tumor | Muscle |
|---|---|---|---|
| 6 hr | 7.4 ± 0.3 | 21.0 ± 7.1 | 10.3 ± 17.9 |
| 24 hr | nd | 16.6 ± 3.9 | nd |
| 48 hr | nd | 9.1 ± 4.5 | 59.5 ± 42.9 | nd = none detected

Figure 12B:
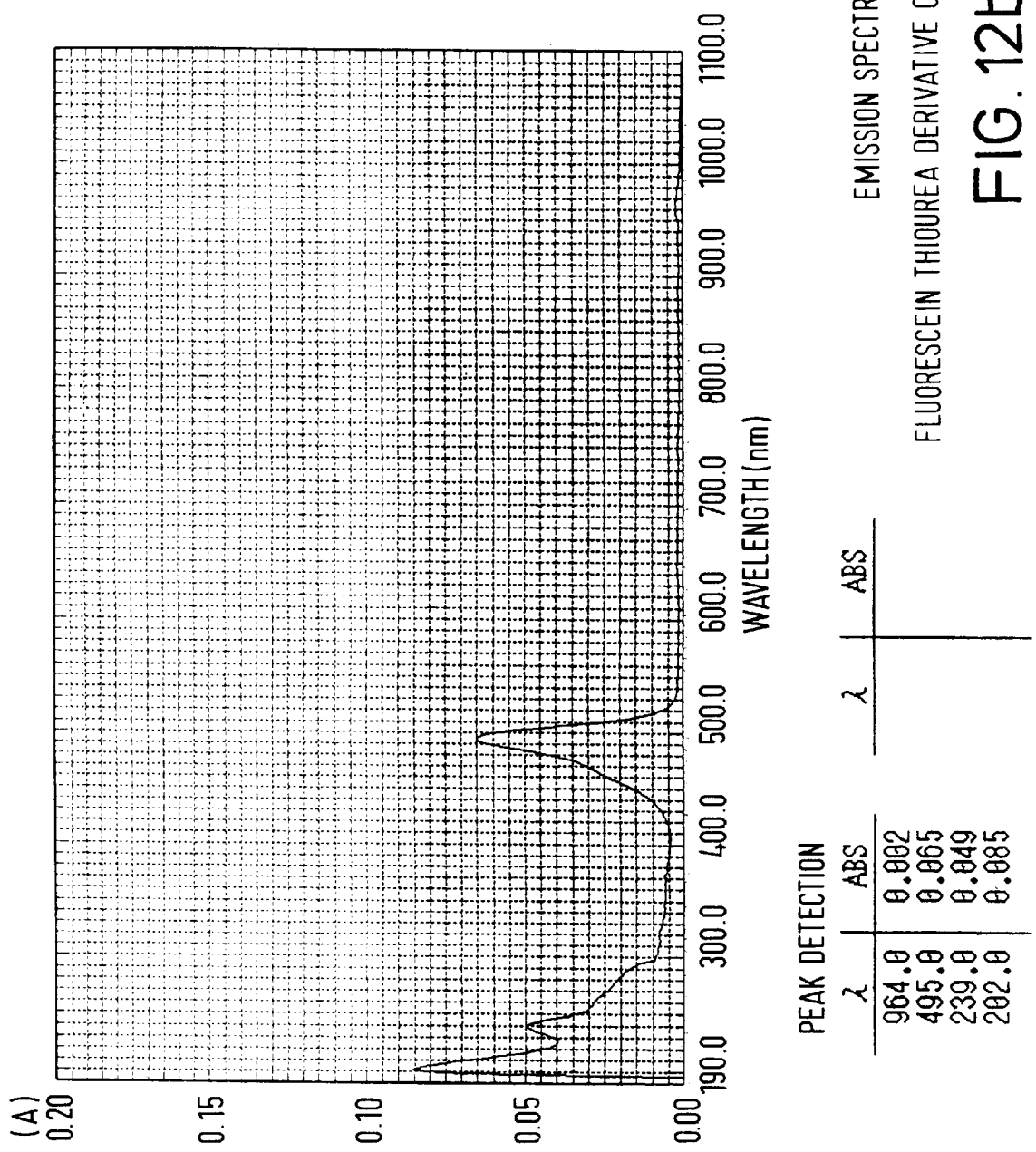

FIGS. 12a and 12b show an emission and and absorption spectrum, respectively, of the Fluorescein thiourea derivative of Surfactant T-908.

EXAMPLE 1
Preparation of Aluminum Chlorophthalocyaninetetrasulfonyl Chloride Polymer With $PEG_{3,400}$-α,ω-diamine, Polymer 1

PEG3400 diamine (Shearwater Polymers, Huntsville, Ala.; 0.39 g) was dissolved in pyridine (75 mL) with magnetic stirring. Approximately 50 mL of pyridine was distilled off under nitrogen from an oil bath at 120–130° to dehydrate the PEG. The solution was cooled to ambient temperature and $ClAlPc(SO_2Cl)_4$ (0.11 g) prepared from the corresponding acid, Porphyrin Products, Logan, Utah) was added. The solution was stirred for 18 hours at 20° and then heated to reflux for 30 minutes, and cooled. The solvent was removed on a rotary evaporator at 40°, and the residue was then dissolved in water. This solution was then passed successively through a strong acid ($H^+$ form) ion exchange resin and then a strong base ($Na^+$ form) ion exchange resin to convert the product to the $Na^+$ salt. Low molecular weight components were removed by diafiltration through a 10,000 molecular weight membrane (Amicon, Beverly, Mass.), and the dark blue residual liquid was evaporated on a rotary evaporator at 40° to yield a dark blue solid (0.09 g). Size exclusion HPLC analysis indicated that the product, Polymer 1, had an average molecular weight of 150,000. Absorption wavelength: $\lambda_{max}$ 676 nm.

EXAMPLE 2
Biodistribution at One Hour in Female Immunodeficient Mice With HT-29 Tumors of Polymer 1

Figure 1:
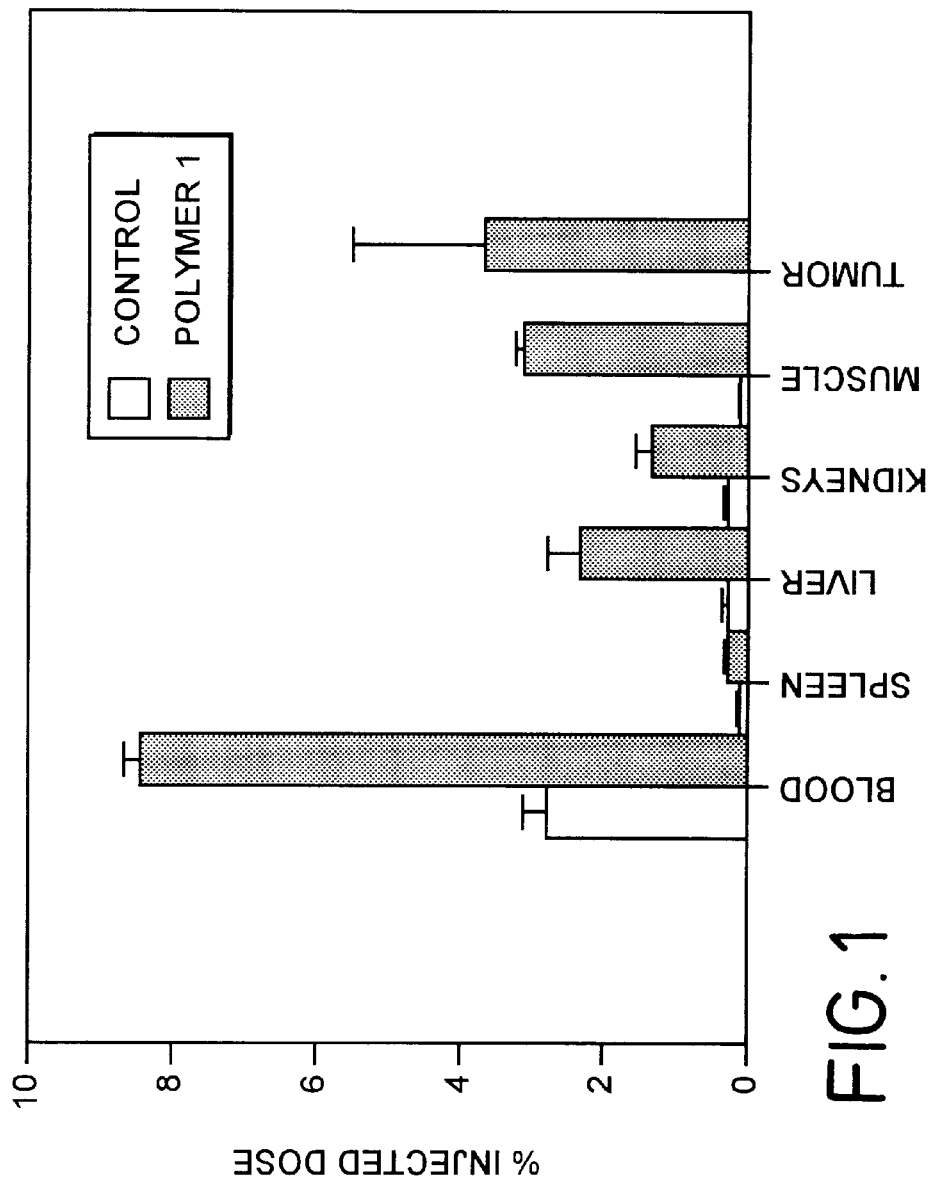
FIG. 1 is a graph of comparative biodistribution data of contrast agent Polymer 1 versus chloroaluminum phthalocyanine tetrasulfonate as control in female immunodeficient mice containing HT-29 tumors at one hour post intravenous injection of phosphate buffered saline solutions of each. Polymer 1 is detected in the tumor; the control compound is negligibly detected.

When a solution of Polymer 1, the compound prepared as in Example 1, in phosphate buffered saline was injected into female immunodeficient mice with HT-29 tumors, 4% of the injected dose was localized in the tumor after one hour. Biodistribution results are presented in FIG. 1.

EXAMPLE 3
Preparation of Aluminum Chlorophthalocyanine Tetrasulfonyl Chloride Polymer With $PEG_{5,000}$-α,ω-diamine, Polymer 2

The method similar to that described in Example 1, above, but employing PEG 5000-α,ω-amine (Shearwater Polymers, Huntsville, Ala.; 2.50 g), pyridine (50 mL, of which about 30 mL were distilled off), and $ClAlPc(SO_2Cl)_4$ (0.10 g) was used to prepare Polymer 2. The aqueous solution was heated to reflux under nitrogen for 30 minutes, and then the solvent was removed by distillation under vacuum. The reaction mixture was diafiltered through a 10,000 molecular weight membrane. The desired product did not pass through the membrane, but was isolated as a dark blue solid (yield: 0.08 g). Absorption wavelength: $\lambda_{max}$ 676 nm.

EXAMPLE 4
Biodistribution at One Hour in Female Immunodeficient Mice With HT-29 Tumors of Polymer 2

Figure 2:
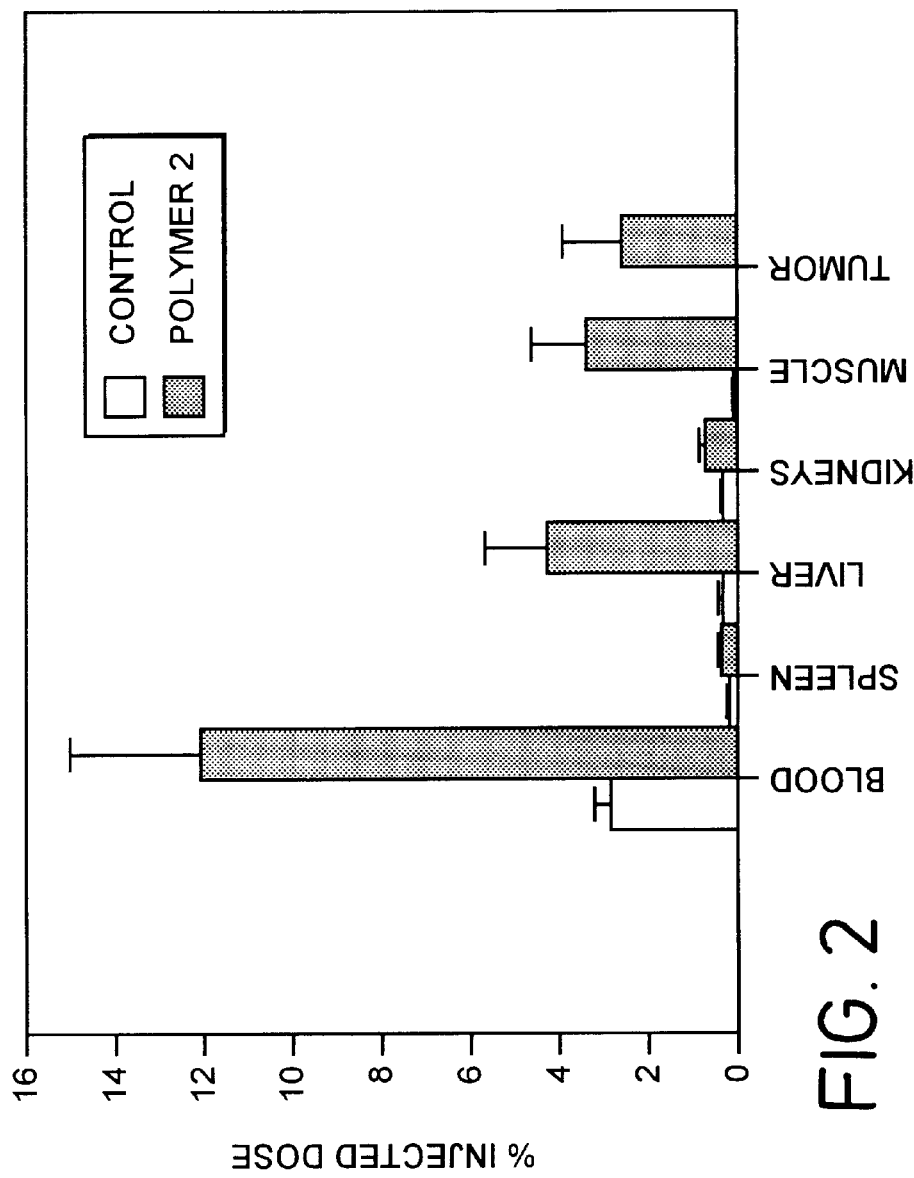
FIG. 2 is a graph of comparative biodistribution data of contrast agent Polymer 2 versus chloroaluminum phthalocyanine tetrasulfonate control in female immunodeficient mice containing HT-29 tumors at one hour post intravenous injection of phosphate buffered saline solutions of each. Polymer 2 is detected in the tumor; the control compound is negligibly detected.

When a solution of Polymer 2, the compound prepared in Example 3, in phosphate buffered saline was injected into female immunodeficient mice with HT-29 tumors, 2.5% of the injected dose was localized in the tumor after one hour. Biodistribution results are presented in FIG. 2.

EXAMPLE 5
Preparation of 2-[2-[2-(4-isothiocyano)phenoxy-3-[[1,3-dihydro-1,1,-dimethyl-3-(3-sulfopropyl)-2H-benz[e]indol-2-ylidene]ethylidene]-1-cyclohexen-1-yl]ethenyl]-1,1-dimethyl-3-(3-sulfopropyl)-1H-benz[e]indolium, Inner Salt The following reaction scheme was used to produce the title compound:

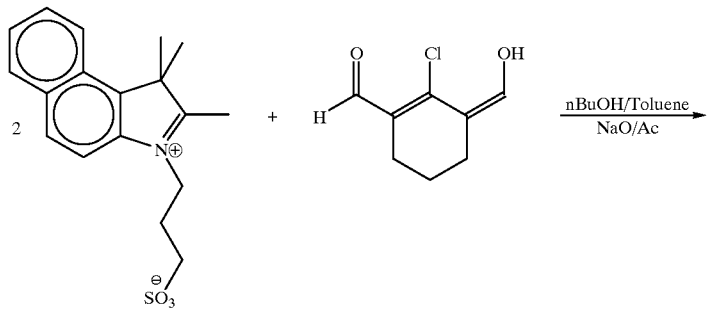

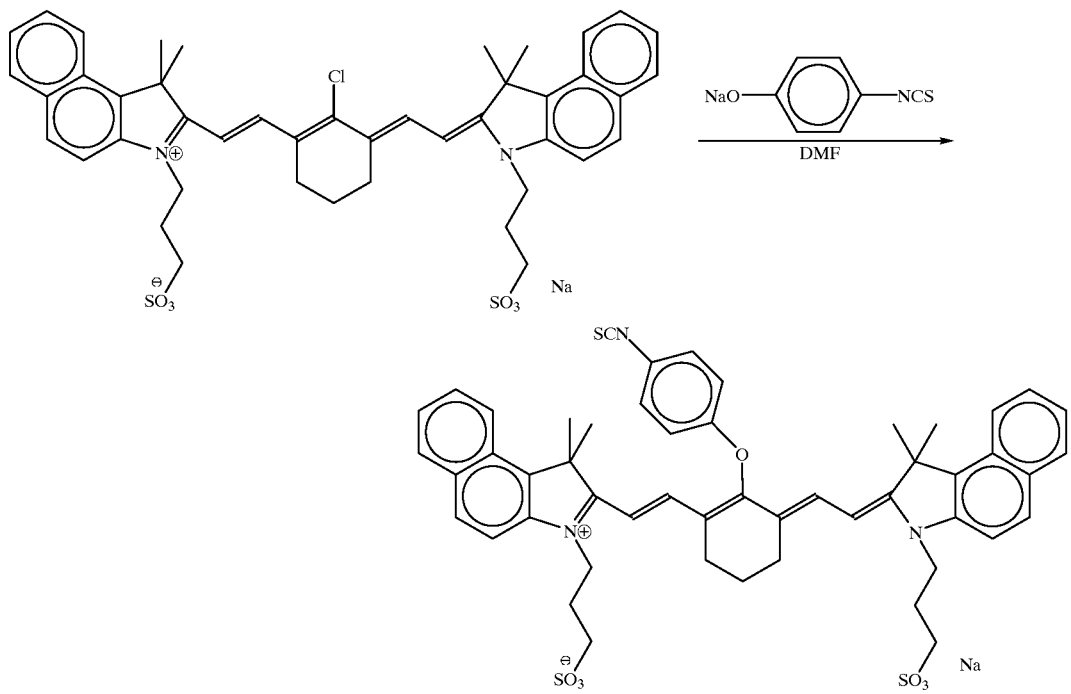
EXAMPLE 6
Preparation of 2-[2-[2-(4-isothiocyano)phenoxy-3-[[1,3-dihydro-1,1,-dimethyl-3-(3-sulfopropyl)-2H-benz[e]indol-2-ylidene]ethylidene]-1-cyclohexen-1-yl]ethenyl]-1,1-dimethyl-3-(3-sulfopropyl)-1H-benz[e]indolium, Inner Salt, Sodium Salt, Reaction Product With $PEG_{3,400}$-α,ω-Diamine
The following reaction scheme was used to produce the title compound:
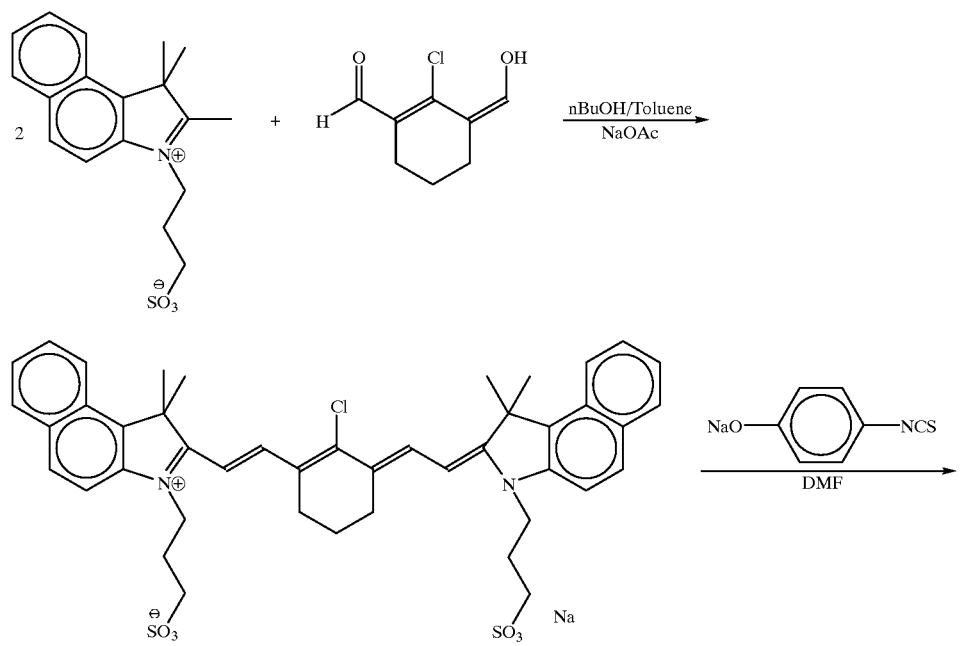

-continued

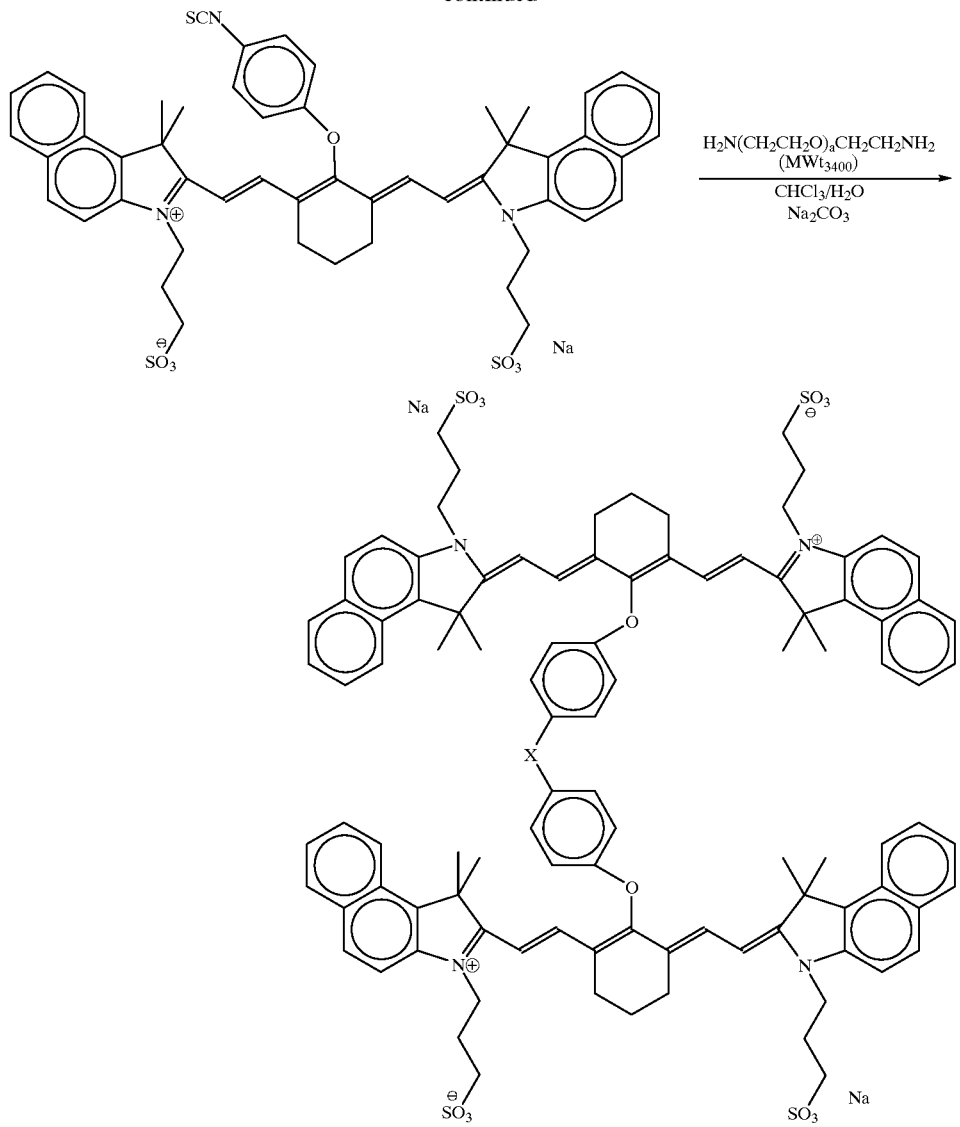

wherein X is NH—CS—NH(CH$_2$CH$_2$O)$_n$CH$_2$CH$_2$NH—CS—NH), a polymer with 3400 molecular weight.

EXAMPLE 7
Preparation of 2-[2-[2-(4-isothiocyano)phenoxy-3-[[1,3-dihydro-1,1,-dimethyl-3-(3-sulfopropyl)-2H-benz[e]indol-2-ylidene]ethylidene]-1-cyclohexen-1-yl]ethenyl]-1,1-dimethyl-3-(3-sulfopropyl)-1H-benz[e]indolium, Inner Salt, Sodium Salt, Reaction Product With PEG$_{10,000}$-α,ω-Diamine The title product was produced analogously to that of Example 6.

EXAMPLE 8
General Method Used For the Measurement of Chromophore-Polymer Distribution in the Mouse Species Tac:N:NIH(S)-nufDF, female immunodef icient mice Tac:Cr:NCr-nufBr, female immunodeficient mice Tumor HT29-Human Colon Carcinoma A) Mouse Methods The mice were randomised into groups based on tumor volumes. On the day of the study, the test articles (Polymers 1,2) were injected into the mice via the tail vein. Chloro-aluminium phthalocyanine tetrasulfonate was used as a reference compound (control) in one group of mice in these studies. The mice were humanely killed one hour post-dosing by halothane inhalation and cervical dislocation. The blood was collected by heart puncture and put into either EDTA or Lithium Heparin tubes. The samples were then spun down and the plasma was collected and weighed. The spleen, liver, kidneys, muscle and tumor were collected, rinsed with PBS and weighed in pre-tared tubes. The samples were then either refrigerated for immediate analysis or frozen at −20 degrees Celcius and subsequently analysed.

B) Plasma Collection and Preparation

Plasma was collected in tared Eppendorf tubes and the tubes were weighed. To each tube was added 1 mL of ethanol. The contents of the tubes were mixed with a vortex mixer and then micro-centrifuged at 14000 rpm for 2 min.

The supernatant liquid was transferred by pipette into a clean and labelled Eppendorf tube. This procedure was repeated for all plasma samples. Each sample was transferred to a clean cuvette and the amount of chromophore was determined by absorbance at a predetermined wavelength. Concentration of the chromophore in the sample was determined by comparison with a standard curve generated from known concentrations of chromophore.

C) Organ Collection and Preparation

Organs were removed from the mice, placed in tared sample tubes, and the new weights were recorded. To each tube was added 1 mL of deionised water, and the organs were homogenised. The homogenate was transferred into a tared Eppendorf tube and the weight was recorded. To this homogenate was added 500 µl of ethanol, the mixture was mixed by vortex mixer, and the contents of the tube was centrifuged in a micro-centrifuge at 8000 rpm for 2 min. The supernatant was transferred by pipette into a clean Eppendorf tube. To the residual pellet was added 500 µl of ethanol, the mixture was mixed by shaking vigorously in a vortex mixer, and the sample was centrifuged again. The supernatants were combined, transferred to a clean cuvette, and the concentration of the chromophore was determined spectroscopically at pre-determined absorbance by comparison with the standard curve. The mean concentration of the chromophore in each organ was determined by regressional analysis.

EXAMPLE 9

Preparation of N-[5-anilino-3-chloro-2,4-(2-ethoxycarbonylpropane-1,3-diyl)-2,4-pentadien-1-ylidene]anilinium Chloride To 34 ml of anhydrous N,N-dimethylformamide, stirred under nitrogen and moderated at 0 to 5° C. by a Dry Ice/isopropanol bath, was added, dropwise over 20 minutes, 28 ml of phosphorous oxychloride. The reaction mixture was allowed to warm for 1 h to 15° C. To this was then added, dropwise over 5 minutes, a solution of 10 g of ethyl 4-oxocyclohexanecarboxylate (Aldrich Chemical Co.) in 20 ml of methylene chloride. After a brief exotherm had subsided, the reaction mixture was heated to reflux for 2 hours. The solvent was then removed by rotary evaporation, and the dark orange viscous residue was cooled in ice. To this was added, over 35 minutes, a solution of 22 ml of aniline dissolved in 22 ml of ethanol. The addition was accompanied by an evolution of fumes and a rise in temperature that was moderated using an ice-salt bath. After the addition was completed, the viscous reaction product was poured over 250 g of ice containing 25 ml of concentrated hydrochloric acid. This mixture was then allowed to stand in a freezer for 2 days. The crude product was isolated by filtration, washed with water and then with ether, and dried over $P_2O_5$ under vacuum to give 14 g of solid. This material was used without further manipulation.

EXAMPLE 10

Preparation of 3-(2,3,3-trimethyl-1H-benz[e]indolio)propanesulfonate

To a magnetically stirred solution of 8.72 g of 1,1,2-trimethyl-lH-benz[e]indole (Fisher Chemical Co.) in 100 ml of anhydrous acetonitrile under nitrogen at room temperature was added 5.09 g of 1,3-propane sultone (Aldrich Chemical Co.) in 3 ml of acetonitrile. The reaction mixture was heated to reflux for 24 hours, and then cooled to ambient temperature. The off-white precipitate was isolated by filtration from the accompanying dark green liquid, washed with 100 ml of acetonitrile and then with 100 ml of ether, and then dried in air to provide 10.24 g of desired compound.

EXAMPLE 11

Preparation of 2-[2-[2-chloro-3-[[1,3-dihydro-1,1,-dimethyl-3-(3-sulfopropyl)-2H-benz[e]indol-2-ylidene]ethylidene]-5-(ethoxycarbonyl)-1-cyclohexen-1-yl]ethenyl]-1,1-dimethyl-3-(3-sulfopropyl)-1H-benz[e]indolium, Inner Salt, Sodium Salt A mixture of 1.87 g of N-[5-anilino-3-chloro-2,4-(2-ethoxycarbonylpropane-1,3-diyl)-2,4-pentadien-1-ylidene]anilinium chloride and 4.3 g of 3-(2,3,3-trimethyl-1H-benz[e]indolio)propanesulfonate in 190 ml of n-butanol containing 75 ml of toluene was heated at reflux for one hour with the removal of water. To the mixture was then added 0.65 g of anhydrous sodium acetate, and reflux was continued for another two and one half hours. The solvent was then removed by distillation to a point were crystals began to form. After cooling, the crystals were isolated by filtration, triturated with ethyl ether, and then recrystallized from methanolic ethyl ether to give 1.7 g of the desired compound.

EXAMPLE 12

Preparation of the Bisthioether 2:1 Dye:Polymer Reaction Product Between 2-[2-[2-chloro-3-[[1,3-dihydro-1,1,-dimethyl-3-(3-sulfopropyl)-2H-benz[e]indol-2-ylidene]ethylidene]-5-(ethoxycarbonyl)-1-cyclohexen-1-yl]ethenyl]-1,1-dimethyl-3-(3-sulfopropyl)-1H-benz[e]indolium, Inner Salt, Sodium Salt and Disodium $PEG_{3,400}$-α,ω-dithiolate, Polymer 3 (NC 100448)

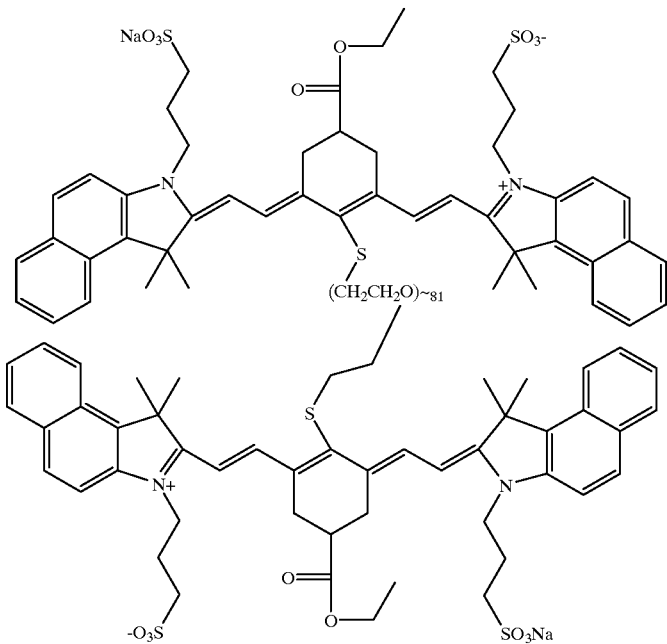

A solution of 1.9 g of 3,400 molecular weight poly(ethylene glycol)-α,ω-dithiol from Shearwater Polymers, Inc. in 8.5 ml of dry and nitrogen-sparged dimethylformamide was treated with 0.1 g of 50% sodium hydride, and then added dropwise under nitrogen at room temperature over 15 minutes to a stirred solution of 0.89 g of 2-[2-[2-chloro-3-[[1,3-dihydro-1,1,-dimethyl-3-(3-sulfopropyl)-2H-benz[e]indol-2-ylidene]ethylidene]-5-(ethoxycarbonyl)-1-cyclohexen-1-yl]ethenyl]-1,1-dimethyl-3-(3-sulfopropyl)-1H-benz[e]indolium in 9 ml of nitrogen-sparged, anhydrous dimethylformamide. After two and one half hours, the reaction mixture was treated with excess carbon dioxide, the solvent was evaporated, and the desired 2:1 dye:polymer adduct was isolated by column chromatography (SiO2: 15% methanol in chloroform).

Biodistribution results are presented in FIGS. 3A (one hour post-dosing) and 3B (three hours post-dosing).

EXAMPLE 13

Preparation of the Bisthioether 2:1 Dye:Polymer Reaction Product Between 2-[2-[2-chloro-3-[[1,3-dihydro-1,1,-dimethyl-3-(3-sulfopropyl)-2H-benz[e]indol-2-ylidene]ethylidene]-5-(ethoxycarbonyl)-1-cyclohexen-1-yl]ethenyl]-1,1-dimethyl-3-(3-sulfopropyl)-1H-benz[e]indolium, Inner Salt, Sodium Salt and Disodium $PEG_{10,000}$-α,ω-dithiolate. (NC 100524)

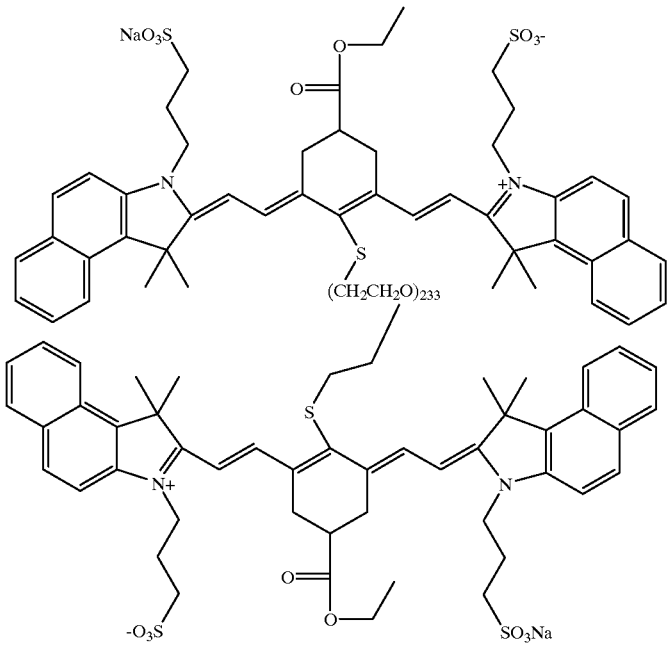

A solution of 2.45 g 10,000 molecular weight poly (ethylene glycol)-α,ω-dithiol from Shearwater Polymers, Inc. in 14 ml dry and nitrogen sparged dimethylformamide was treated with 43 mg 50% sodium hydride and 1.5 ml dry dimethylformamide. After about one half hour this solution was added dropwise in one third hour to a nitrogen sparged solution of 0.4 g of sodium 4-(2-(4-chloro-7-(3,3-dimethyl-1-(3-sulfonatopropyl)benz(e)indolin-2-ylidene-3,5-(2-ethoxycarbonylpropane-1,3-diyl)-1,3,5-hepatatriene-1-yl)-3,3-dimethyl-3H-benz(e)indolio)propanesulfonate in 5 ml dry nitrogen sparged dimethylformamide, with stirring. After four hours of stirring under a nitrogen atmosphere, the reaction mixture was treated with excess carbon dioxide followed by evaporation of the solvent. The desired dark green 2:1 dye:polymer adduct was isolated by column chromatography ($SiO_2$: 20% methanol in chloroform). Absorption maxima in phosphate buffered saline: 814 nm, 744 nm. The mass spectrum had a distribution centered approximately at 12,000 mass units, as expected.

EXAMPLE 14
Preparation of a Derivative of the Polymeric BASF Surfactant T908 Terminated With Zinc Trisulfophthalocyanine Groups (NC 100526)

This dye was made from the Surfactant T908 amino derivative (2.50 g, 0.1 mM) by a method analogous to that of Example 29 but using a tenfold excess of zinc phthalocyanine tetrasulfonyl chloride (4.0 g, 4.1 mM). The diafiltrate retentate (10000 molecular weight membrane) was evaporated and freeze dried to yield a dark blue solid, 3.2 g, lambda max. 635 nm (shoulder at 671 nm) in water.

EXAMPLE 15
Preparation of [PcAlCl($SO_3H$)$_3SO_2NH$]$_2$[PEG 10,000](NC 100481)

This was prepared by a method analogous to that used in Example 1 but using PEG 10,000 diamine (Shearwater Polymers, 1.0 g, 0.1 mM) and an excess of chloro-aluminumphthalocyanine tetrasulfonyl chloride (0.217 g, 0.22 mM). The diafiltrate retentate (3000 molecular weight membrane) was evaporated to yield a dark blue solid, 0.82 g, lambda max. 675 nm in water.

EXAMPLE 16
Preparation of Cofacial SiPc—PEG 3400 Alternating Polymer

Silicon phthalocyanine dihydroxide (Aldrich, 1.0 mM), imidazole (Aldrich, 3.0 mM), and DMF (2 mL) are stirred under nitrogen for 5 minutes. 3-Isocyanatopropyldimethylchlorosilane (Gelest, 2.0 mM) is added and the mixture stirred for 48 hours. Methanol (5 mL) is added, the solution filtered, and the solvents removed under vacuum. The residue is chromatographed on silica, eluting with toluene containing increasing concentrations of methanol. The blue eluate containing the required product is collected and the solvent removed under vacuum. This product (1.0 mM) in isopropanol (10 mL) is mixed with a solution of PEG 3400 diamine (Shearwater Polymers, 1.0 mM) in isopropanol (10 mL) and heated with stirring under nitrogen at 40° C. for 5 hours. The solvent is removed under vacuum, and the required product isolated by chromatography on silica.

EXAMPLE 17
Preparation of Cofacial AlPc—PEG 10,000 Compound

Aluminum phthalocyanine hydroxide (Aldrich, 1.0 mM), imidazole (Aldrich, 3.0 mM), and DMF (2 mL) are stirred under nitrogen for 5 minutes. 3-Isocyanatopropyldimethylchlorosilane (Gelest, 2.0 mM) is added and the mixture stirred for 48 hours. Methanol (5 mL) is added, the solution filtered, and the solvents removed under vacuum. The residue is chromatographed on silica, eluting with toluene containing increasing concentrations of methanol. The blue eluate containing the required product is collected and the solvent removed under vacuum.

This product (2.0 mM) in isopropanol (10 mL) is mixed with a solution of PEG10,000 diamine (Shearwater Polymers, 1.0 mM) in isopropanol (10 mL) and heated with stirring under nitrogen at 40° C. for 5 hours. The solvent is removed under vacuum, and the required product isolated by chromatography on silica.

EXAMPLE 18
Preparation of [NH(PEG3400)NHSO$_2$PcAlCl (SO$_3$H)$_2$SO$_2$]$_n$ PEG 3400 diamine (Shearwater Polymers, Huntsville, Ala.; 0.391 g, 0.115 mMoles) was dissolved in pyridine (75 mL) with magnetic stirring. Approximately 50 mL pyridine were distilled off under nitrogen from an oil bath at 120–130° to dehydrate the PEG, and then the solution was cooled to ambient temperature and ClAlPc(SO$_2$Cl)$_4$ (prepared from the corresponding acid, Porphyrin Products, Logan, Utah) added (0.111 g, 0.115 mMoles). The solution was stirred for 18 hours at 20° and then refluxed for 30 minutes, after which the solvent was removed on a rotary evaporator at 40° and the residue dissolved in water. This solution was then passed successively through strong acid and strong base (Na form) ion exchange resins to convert the product to the Na salt. Low molecular weight components were removed by diafiltration through a 10,000 molecular weight membrane (Amicon, Beverly, Mass.) and the dark blue residual liquid evaporated on a rotary evaporator at 40° to yield a dark blue solid (0.09 g).

Size exclusion HPLC analysis indicated that the product had an average molecular weight of 150,000, and it had $\lambda_{max}$ 676 nm (water).

When a solution of this compound in phosphate buffered saline was injected into female immunodeficient mice with HT-29 tumors, 4% of the injected dose was localized in the tumor after one hour.

EXAMPLE 19
Preparation of [NHCH$_2$CH$_2$NHSO$_2$PcAlCl(SO$_3$H)$_2$SO$_2$]$_n$ This was prepared by the same method used in Example 18, but using ethylenediamine (Aldrich, 0.0058 g, 0.10 mMoles) in place of the PEG diamine. The aqueous solution of the product was diafiltered through a 500 molecular weight membrane, and the dark blue residual solution ion exchanged to the sodium salt, and evaporated to yield a dark blue solid (0.10 g).

EXAMPLE 20
Preparation of ClAlPc(SO$_2$NHPEG5000)$_4$

The method used was similar to that described in Example 18, but using PEG 5000 α,ω-bis amine (Shearwater Polymers, Huntsville, Ala.; 2.50 g, 0.50 mMoles), pyridine (50 mL, of which about 30 mL were distilled off), and ClAlPc(SO$_2$Cl)$_4$ (0.10 g, 0.10 mMoles). The solution was refluxed under nitrogen for 30 minutes, and then the solvent was removed. Diafiltration using a 10,000 molecular weight membrane, collecting the product that did not pass through the membrane, yielded a dark blue solid (0.08 g). It had $\lambda_{max}$ 676 nm (water). When a solution of this compound in phosphate buffered saline was injected into female immunodeficient mice with HT-29 tumors, 2.5% of the injected dose was localized in the tumor after one hour.

EXAMPLE 21
Preparation of a Stable Emulsion of Sudan III

Sudan III (also known as, D&C Red No 17, Solvent Red 23, Cerasin Red) is very water insoluble but soluble in sesame oil, a well known oil for parenteral oil-in-water emulsions (e.g., Intralipid, Lyposin, etc.) and has a $\lambda_{max}$ of 507 nm. Thus, an emulsion of Sudan III was prepared as follows: A saturated solution of Sudan III in sesame oil was prepared by gently rotating the container over the weekend (approx 72 hr). The oil solution was then filtered through a 5 micron syringe filter followed by a 0.8 micron filter to remove undissolved solid Sudan III. The resulting saturated solution was then emulsified in water at a ratio of 10% "oil" to 90% aqueous surfactant solution using ultrasonic energy followed by microfluidization at approx 14,000 PSI until a constant droplet size was achieved. Droplet size was measured by light scattering using a Horiba 910 light scattering device and a volume weighted average. The resulting emulsions were also sterilized by traditional steam sterilization and the droplet size measured again. The results are:

| Formulation | Average Droplet Size (nm) | |
| --- | --- | --- |
| | Before Autoclaving | After Autoclaving |
| 1. 1.2% lecithin, 0.3% F68 | 787 | 909 |
| 2. 1.2% Lecithin, 2% P79 | 141 | 199 |
| 3. 0.8% Lecithin, 3% P79 | 122 | 128 |

P79, described in Example 2k of PCT/GB95/02109, is a PEG-double ester of molecular weight about 10000 and formula CH$_3$(CH$_2$)$_{14}$COO(CH$_2$)$_{15}$COO((CH$_2$)$_2$O)$_n$CH$_3$.

P79 is a polymeric surfactant which appears to add greatly to the ability to make a small emulsion droplet of sesame oil saturated with the Sudan III. The resulting rose colored emulsion is stable on the shelf.

This emulsion (Sudan III) may be injected peri-tumorally to migrate to the regional draining lymph nodes for ease of resection. (This is currently done in melanoma and breast cancer. These nodes are important for staging the progress of the disease and planning patient management). This emulsion may also make the histopathology easier and more accurate by staining the healthy tissue thereby making the disease tissue more obvious as a filling defect to the emulsion. Further, the emulsion may be administered iv to effect a marking of the healthy tissue of the liver and spleen and other organs which are MPS rich. This will provide visible contrast between the healthy tissue and diseased tissue, lesions, malformations, etc., for ease in surgical resection. Even areas with low or blocked blood flow would be contrasted with normal vascular beds via the content of the blood of the Sudan III emulsion (P79 has been shown to afford prolonged circulation to liposomes and emulsions in corresponding X-ray contrast formulations).

EXAMPLE 22
Preparation of Nanoparticles of Fluorescein

A nanoparticle suspension of Fluorescein was prepared by placing 7.5 ml of milling beads (0.7 mm zirconium silicate) and 0.9 gm of fluorescein into a 15 ml bottle. Using a stock solution of surfactant, the suspension was made up to 3.3 ml in aqueous phase. This was done for each of 3 surfactants: Brij 58, Tyloxapol, and Pluronic F-108. The particle sizing results were:

| formulation | Day 3 | Day 5 | Day 6 |
| --- | --- | --- | --- |
| F108 | 247 μm | 4.4 μm | 194 nm |
| Tyloxapol | 91 nm | — | — |
| Brij 58 | 101 nm | — | — |

A sterile filtered suspension of fluorescein prepared in this manner was administered subcutaneously to an anesthetized dog with a cannulated thoracic duct to monitor lymph flow and contents. The fluorescein may be detected in the lymph fluid indicating that the dye nanoparticles are passing through the lymphatics thereby marking the lymph nodes as required to aid in the visual identification of lymph nodes for resection and use in cancer staging.

These particles will also function after iv administration in marking tissues rich in MPS cells such that healthy tissue will be marked while disease tissue will remain dark and easily identifiable during surgical resection.

EXAMPLE 23
Formulation of Indocyanine Green in a Liposome

Indocyanine Green (ICG) was added to a liposome suspension formed from 8.2% lecithin (phosphatidyl choline), 0.8% dimyristylphosphatidylglycerol, and 0.1% of a nonionic, polymeric surfactant, P-79 which is designed to impart prolonged blood pool residence to the liposome. The phospholipids and the surfactant were mixed in water using ultrasonic energy from a probe sonicator (Bransonic Sonifier 450, 90% duty cycle, output 10). Liposomes were prepared using a Microfluidics M110S microfluidizer at 14,000 PSI and 4 passes through the interaction chamber of the phospholipid mixture. The resulting liposomes were approximately 100 nm in average diameter as determined by light scattering and remained the same size after autoclave sterilization. In addition, these liposomes were able to pass through a sterile filter (i.e., 0.2 micron pore size). Addition of ICG in sufficient amount to make the suspension approximately 7 mg/ml in ICG did not alter the physical characteristics of the liposomal suspensions. After sterilization under a nitrogen atmosphere, these ICG liposomes were stable for at least 6 weeks at room temperature.

Assessment of the spectral properties of the liposomal ICG relative to ICG dissolved in water or saline demonstrated the impact of the liposomal environment. Both the excitation maximum wavelength and emission maximum wavelength were shifted to lower energies (i.e., higher wavelengths) relative to the homogeneous water solutions. In addition, careful measurements of quantum yield demonstrate at least a 4 fold increase in quantum yield of the liposomal ICG relative to the aqueous ICG solutions. Thus, the dose required for light imaging contrast utility of the liposomal formulation of ICG should be significantly less than that required from a homogeneous aqueous solution of ICG.

EXAMPLE 24
Use of Contrast Media For Enhancement of Laser Doppler Measurement of Blood Flow in the Skin Approximately 0.5 to 1 hour before the measurements are to be made a sterile solution of a contrast medium containing 5–20 mg of a dye with an absorbing maximum between 600 and 1300 nm (e.g., a Pc dye as described in the foregoing Examples) is administrated by intravenous injection. The actual measurement of blood flow is made with a standard laser Doppler instrument, for example that from Lisca Development AB, Kinkoping, Sweden, that optionally may be modified to incorporate a laser source operating at 830 or 780 nm (Abbot, N. C.; Ferrell, W. R.; Lockhart, J. C.; Lowe, J. G., "Laser Doppler Perfusion Imaging of Skin Blood Flow Using Red and Near-Infrared Sources", *J. Invest. Dermatol.*, 1996, 107, 882–886) after the concentration of contrast agent in the blood has stabilized. In this way, highly vascularized, particularly tumorous, structures may be identified.

EXAMPLE 25
Preparation of Reaction Product 2-[2-[2-(4-isothiocyano) phenoxy-3-[[1,3-dihydro-1,1,-dimethyl-3-(3-sulfopropyl)-2H-benz[e]indol-2-ylidene]ethylidene]-1-cyclohexen-1-yl] ethenyl]-1,1-dimethyl-3-(3-sulfopropyl)-1Hbenz[e] indolium With PEG 3400 α,ω-diamine The following reaction scheme was used to produce the title compound:

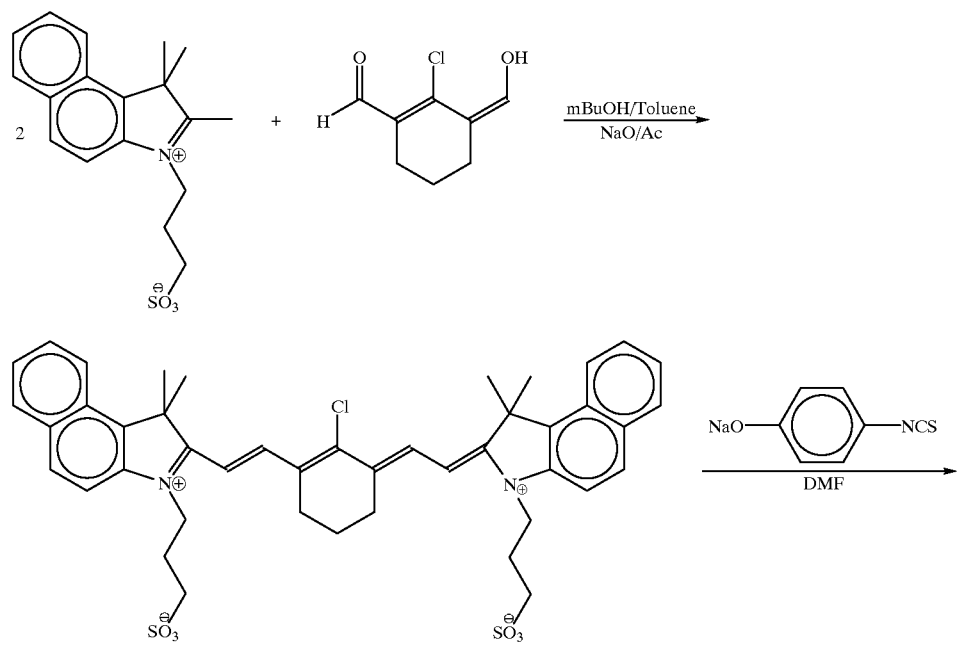

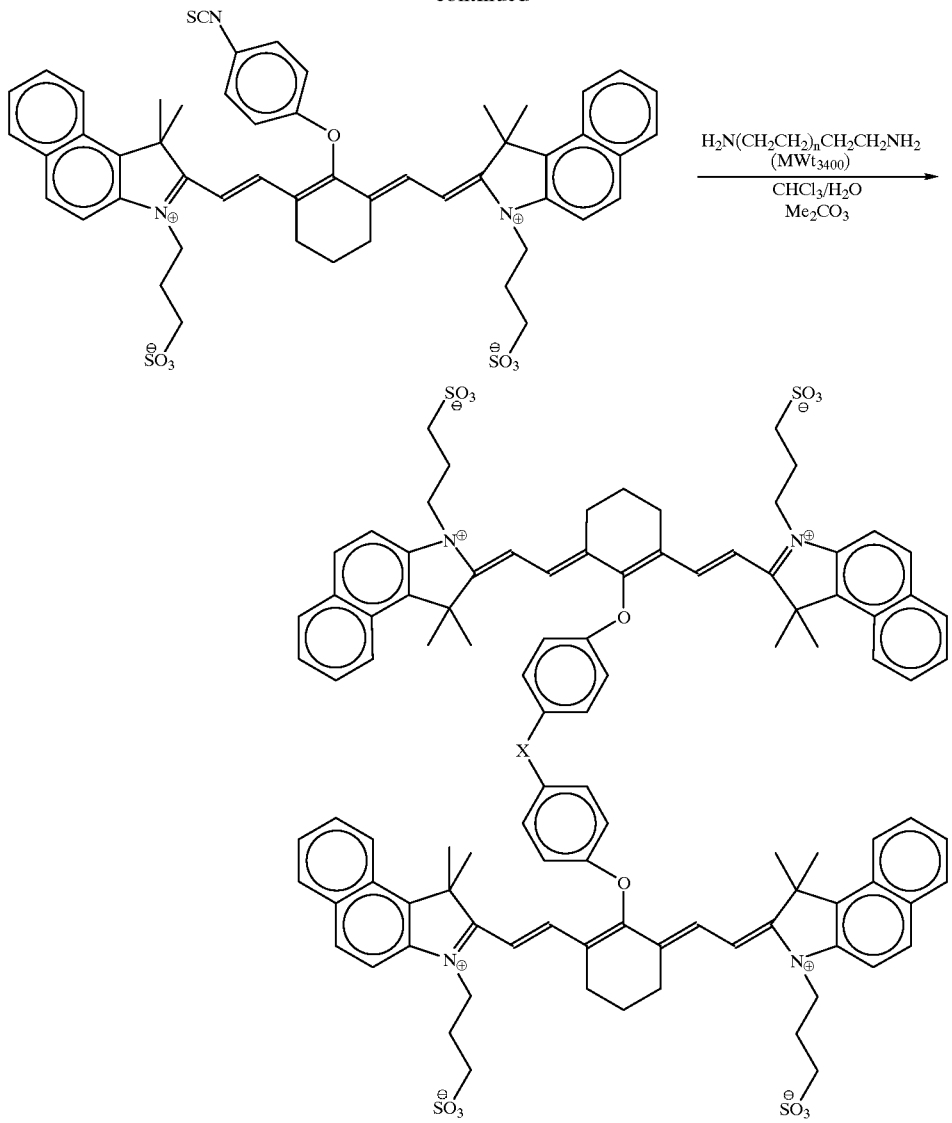

wherein X is NH—CS—NH(CH$_2$CH$_2$O)$_n$CH$_2$CH$_2$NH—CS—NH).

EXAMPLE 26

Preparation of 2-[2-[2-(4-isothiocyano)phenoxy-3-[[1,3-dihydro-1,1,-dimethyl-3-(3-sulfopropyl)-2H-benz[e]indol-2-ylidene]ethylidene]-1-cyclohexen-1-yl]ethenyl]-1,1-dimethyl-3-(3-sulfopropyl)-1Hbenz[e]indolium Reaction Product With PEG 10000 α,ω-diamine The title product was produced analogously to that of Example 25.

EXAMPLE 27

(See Attached Synthetic Scheme; A→F)

Preparation of α,ω-Bis-(rhodamine B sulfonamide) Analog of Poly(oxyethylene-co-oxypropylene-co-oxyethylene) Block Copolymer With a Block Ratio of 40:20:40 and a Weight Average M. W. of Approximately 14,600

Synthesis of the α,ω-bis-(amino) analog of poly(oxyethylene-co-oxypropylene-co-oxyethylene) block copolymer with a block ratio of 40:20:40 and a weight average M. W. of approximately 14,600 (Compound E):

A total of 50.0 g. of poly(oxyethylene-co-oxypropylene-co-oxyethylene) block copolymer with a block ratio of 40:20:40 and an average molecular weight of approximately 14,600 (Pluronic Surfactant F-108, BASF Corp.) (starting material A, above) was treated with 275 ml of toluene and refluxed for two hours over a Dean Stark trap. The system was then cooled and the trap and its contents (about 25 ml) removed. At this point the reaction mixture was treated with 1.25 ml of thionyl chloride and 0.053 ml of anhydrous dimethylformamide and stirred at 105° for 2 hours. The system was then allowed to stir at room temp. overnight. Next day the reaction mixture was stripped on a rotary evaporator to give 49.35 g of an off-white solid which was readily powdered (intermediate B). In addition to the dominant polyalkylene oxide peaks between 70 and 80 ppm (also seen in the starting Surfactant F-108) the $^{13}$C NMR spectrum of the product contains a singlet at 42.69 ppm, consistent with terminal carbons bearing chlorines, and no remaining peak near 61 ppm where the terminal hydroxyl-bearing carbons of Surfactant F-108 show up.

A total of 49.08 g of intermediate B, 0.89 g of sodium azide, and 2.83 g of potassium iodide were treated with 350 ml of anhydrous dimethylformamide and stirred at 100° for 5 hours under dry argon. The reaction mixture was then stirred at room temperature overnight under argon. It was then stripped on a rotary evaporator at 50° to a melt which solidified to a tan solid. The solid was dissolved in 500 ml of distilled water and shaken with 500 ml of chloroform. Upon layer separation (very slow), the aqueous layer was extracted with two 500 ml portions of chloroform. The three chloroform layers were combined and dried over magnesium sulfate. Upon stripping volatiles, 45.58 g of a white solid was obtained (intermediate C). The $^{13}C$ NMR spectrum of the product contains a singlet at 50.6 ppm, consistent with terminal carbons bearing azides, and no remaining peak near 42 ppm from the starting bis-chloride.

A total of 44.05 g of intermediate C was treated with 3.15 g of triphenyl phosphine and 2300 ml of anhydrous pyridine. The reaction mixture was stirred under argon at room temperature. The bis-triphenyl phosphine analog prepared in this reaction (intermediate D) was used directly, without isolation, in the next step of the synthesis.

The reaction mixture from the previous step was treated with 200 ml of 30% ammonium hydroxide (aqueous) and stirred at room temperature for 7 hours. The foaming was vigorous, requiring a very large vessel to avoid foam-over. It was then stripped on a rotary evaporator overnight and the residual solid redissolved in 500 ml of chloroform. Following drying over magnesium sulfate the volatiles were stripped to an off white solid comprising 39.31 g. When a phosphorus NMR spectrum of the product indicated that a significant phosphorus signal still remained, a 2.0 g sample of the product was treated with 38 ml of 30% ammonium hydroxide (aqueous) and stirred at 60° for 4 hrs. The reaction mixture was then cooled to room temperature, washed with four-40 ml portions of ether, and restripped on a rotary evaporator. The product is an off white waxy solid comprising 1.46 g (intermediate E) This time no phosphorus signal was found in the phosphorus NMR. Also the $^{13}C$ NMR spectrum contained a peak at 41.78 ppm, consistent with the terminal carbons bearing amines, and had no remaining peak near 50 ppm corresponding to the starting bis-azide.

Synthesis of the α,ω-bis-(rhodamine B sulfonamide) analog of poly(oxyethylene-co-oxypropylene-co-oxyethylene) block copolymer with a block ratio of 40:20:40 and a weight average molecular weight of approximately 14,600.

A total of 1.25 g of the α,ω-bis-(amino) analog of Pluronic Surfactant F-108 from above (intermediate E) was treated with 0.026 g of dimethylaminopyridine and 10 m of anhydrous pyridine. The resulting solution was treated with 0.12 g of rhodamine B sulfonyl chloride (Molecular Probes) and stirred at room temperature under nitrogen overnight. The resulting intensely purple solution was stripped on a rotary evaporator to an intensely purple solid comprising 1.42 g. A total of 1.0 g of the crude product was dissolved in 40 ml of distilled water, filtered through a 0.45 micron nylon filter, and the filtrate diafiltered against distilled water using an 50 ml stirred diafiltration cell (Amicon) containing a 3,000 nominal molecular weight cellulose acetate diafiltration membrane (Amicon YM-3). The diafiltration was continued for 35 turnovers (1,750 ml of diafiltrate removed). Initially, the diafiltrate was intensely purple, but as the purification continued the color intensity diminished till it was virtually colorless at 35 turnovers. The intensely purple retentate was stripped on a rotary evaporator to an intensely purple solid which comprised 0.92 g (final product F). The $^{13}C$ NMR spectrum of the product contains the dominant polyalkylene oxide peaks between 70 and 80 ppm seen in F-108 and all the subsequent intermediates, as well as a new singlet at 45.69 ppm. No remaining peak near 41 ppm, corresponding to the previous bis-amine intermediate, was observed. Size exclusion HPLC studies indicate a single broad peak with a peak molecular weight of approximately 15,000 based on PEG standards. The compound shows a broad spectral absorbance peaking at 584 nm.

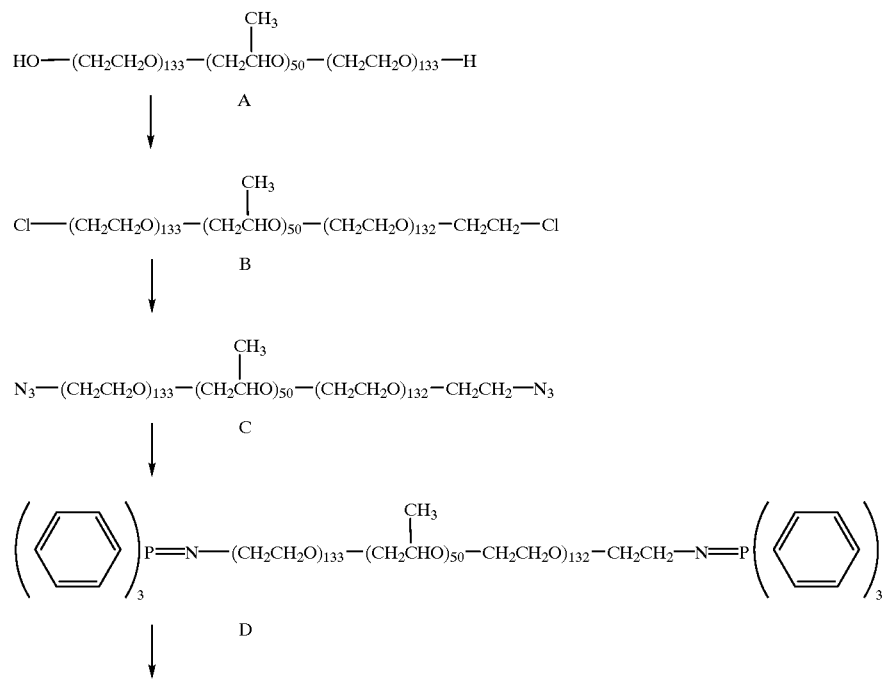

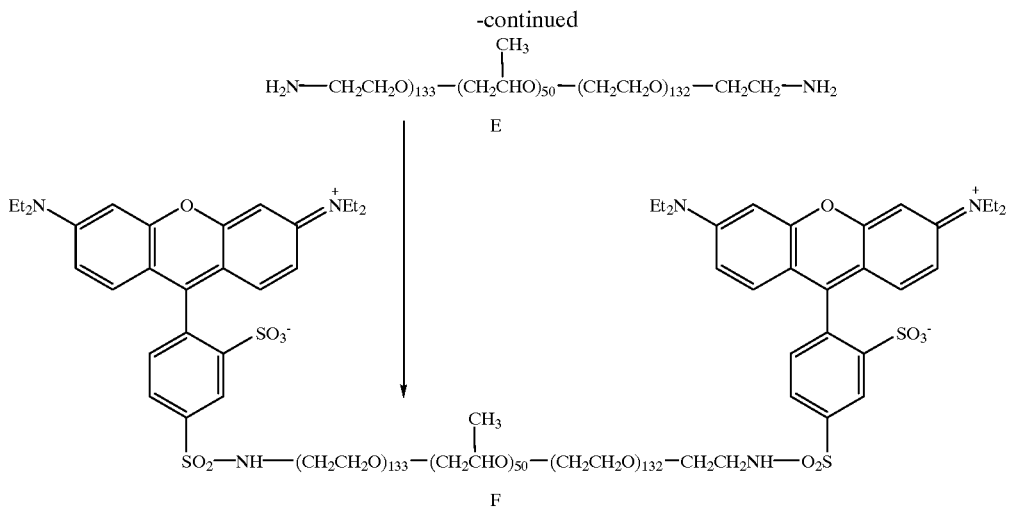

EXAMPLE 28
Preparation of a Derivative of the Polymeric BASF Surfactant T908 Terminated With Sulfoindocyanines A total of 0.30 g of the terminal amino derivative of Surfactant T908 was dissolved in 3.0 ml of distilled water and then treated with 2.9 ml of 0.5M aqueous sodium carbonate. The resulting clear solution was treated with 0.19 g of the sulfoindocyanine dye sold as Cy-7 dye by Amersham and stirred at room temperature for 18 hours. The resulting clear solution was diluted with 6.0 ml of distilled water and placed in a stirred diafiltration cell equipped with an Amicon YM-10 (nominal 10K cutoff) diafiltration membrane. It was diafiltered until 250 ml of diafiltrate had been removed (21 turnovers). The retentate was the freeze dried to a fluffy polymeric solid comprising 0.21 g Spectral analysis showed the polymer has a lambda max. (absorption) of 741 nm.

EXAMPLE 29
Preparation of the Fluorescein Thiourea Derivative of Surfactant T908 (BASF) (NC100505)
Terminal Amino Derivative of Surfactant T908

A total of 100.0 g of Surfactant T908 (BASF) was treated with 525 ml of toluene and refluxed for an hour under a Dean-Stark trap. The Dean-Stark trap was then removed along with the approximately 25 ml of toluene/water it contained. Upon cooling to room temperature, the reaction mixture was treated with 2.92 ml of thionyl chloride and 0.12 ml of DMF. It was reheated to 105° C. and stirred under argon for 3 hours, cooled to room temp, and stripped on a rotary evaporator to a light tan powder comprising 101.99 g.

A total of 100.0 g of this "chloro-T908" intermediate was treated with 2.08 g of sodium azide, 5.98 g of potassium iodide, and 700 ml of DMF. The reaction mixture was heated to 100° C. for 6 hours, cooled to room temperature, and then stripped on a rotary evaporator at 69° C. The crude product was dissolved in 900 ml of distilled water and shaken with 1 liter of chloroform. The chloroform layer was collected and combined with two additional 500 ml chloroform washes of the aqueous layer. After drying the combined chloroform layers over magnesium sulfate the chloroform was stripped on a rotary evaporator to give 65.69 g of a light tan frangible solid.

A total of 62.5 g of this "azido-T908" intermediate was dissolved in 300 ml of anhydrous pyridine and treated with 6.56 g of triphenylphosphine. After stirring it at room temperature for 18 hours, the resulting clear solution was treated with 300 ml of 30% ammonia (aqueous) and stirred under argon at 50° C. for 5 hours. It was then stripped on a rotary evaporator and subsequently treated with 562.5 ml of DMSO and 2,250 ml of distilled water. The resulting solution was diafiltered for 12 turnovers using a Millipore spiral wound permeator with a nominal 10K cutoff. The final retentate was freeze dried yielding 43.22 g of an off-white powder. A high field $^{13}$C NMR of the product showed a peak at 41.78 ppm, consistent with that expected for the methylene adjacent to the terminal amine of the desired product, and showing no aromatic peak in either the $^{13}$C or $^{1}$H or spectra as well as no peaks in the $^{31}$P spectrum indicating the triphenylphosphine adduct has been completely converted to the desired amino adduct.

Terminal Fluorescein Derivative of Surfactant T908

A total of 1.00 g of the above terminal amino derivative of Surfactant T908 was dissolved in 10 ml of distilled water and then treated with 3.2 ml of 0.5M aqueous sodium carbonate. The resulting clear solution was treated with 0.156 g of fluorescein isothiocyanate, isomer I (Aldrich) and stirred at room temperature for 18 hours. The resulting clear intensely orange solution was diluted with 60 ml of distilled water and placed in a stirred diafiltration cell fitted with an Amicon YM-10 (nominal 10K cut-off) diafiltration membrane. It was initially ultrafiltered down to a retentate volume of 25 ml and was subsequently diafiltered until 600 ml of diafiltrate had been removed (24 turnovers). The retentate was then freeze dried to a bright orange fluffy polymeric solid comprising 0.43 g. Spectral analysis showed the polymer has a lambda max. (absorption) of 307 nm.

EXAMPLE 30
Fluorescence Imaging With NC100505 in Confocal Microscopy

Images of blood vessels in the ear of a hairless rat were obtained before and after injection of 20 mg/(kg body weight) of NC100505 in a femoral vein. The excitation wavelength was 488 nm, and the fluorescent image was detected after passage through a 540 nm long-pass filter and a 60×, NA water-immersion objective lens.

Blood flow was barely detectable without the contrast agent. After injection, moving blood cells in vessels at depths between 0.05 and 0.1 mm were readily visible as dark areas in contrast with bright plasma. Occasional "blobs" of brightness, possibly blood cells coated by the agent were visible. Photobleaching occurred within 30 to 120 seconds at an illumination power of 30 milliwatts. However, the overall brightness in the blood persisted for at least 30 minutes after injection.

EXAMPLE 31
Use of Contrast Media in Two-photon Microscopy

Contrast agent NC100505 is suitable for use with two-photon microscopy. A suitable light source is a femto-second laser, such as an In/Ga/As laser, tuned approximately to 980 nm. Other details of the imaging procedure are included in Masters, B. R. et al., *Annals N. Y. Acad. Sci.,* 1998, 838, 58–67.

The contrast agent is bolus administered in a PBS solution to a femoral vein of a hairless rat at a dose level of 10 mg/kilogram. Images are acquired of blood vessels in the ear, which appear bright yellow in the presence of the fluorescing contrast agent.

What is claimed is:

1. A physiologically tolerable water-soluble light imaging contrast agent having a molecular weight in the range 500 to 500000 and containing at least two chromophores having delocalized electron systems that are linked to one polyalkylene oxide (PAO) moiety having a molecular weight in the range 60 to 100000.

2. A contrast agent as claimed in claim 1 wherein said PAO moiety has a molecular weight in the range 200 to 100000.

3. A contrast agent as claimed in claim 1 wherein said PAO moiety has a molecular weight in the range 250 to 50000.

4. A contrast agent as claimed in claim 1 wherein said PAO moiety has a molecular weight in the range 250 to 25000.

5. A contrast agent compound as claimed in claim 1 wherein said PAO moiety has a molecular weight in the range 400 to 15000.

6. A contrast agent as claimed in claim 1 wherein said chromophores are not lanthanide chelates unless said agent also comprises a chelated Tc, Sm, or Cu radionuclide.

7. A contrast agent as claimed in claim 1 wherein said PAO moiety comprises a block copolymer of polypropylene oxide and polyethylene oxide.

8. A contrast agent as claimed in claim 1 wherein said block copolymer is a linear polymer.

9. A contrast agent as claimed in claim 1 wherein said block copolymer is a branched polymer.

10. A contrast agent as claimed in claim 1 wherein said block copolymer is selected from the group consisting of Tetronic and Pluronic copolymers.

11. A contrast agent as claimed in claim 1 wherein said PAO moiety has a molecular weight in the range 1000 to 40000.

12. A contrast agent as claimed in claim 1 comprising at least three chromophores.

13. A contrast agent as claimed in claim 1 comprising at least four chromophores.

14. A contrast agent as claimed in claim 1 wherein the chromophores are selected from the group consisting of fluorescein, phthalocyanine and cyanine.

15. A contrast agent compound as claimed in claim 1 comprising moieties of formula I:

$$\text{Chr-L[PAO-L-Chr]}_n \qquad (I)$$

wherein
each Chr which may be the same or different is a chromophore,
each PAO which may be the same or different is a polyalkylene oxide moiety,
each L is a bond or organic linking group connecting at least one PAO to at least one Chr, and
n is an integer having a value of at least 1.

16. A contrast agent compound as claimed in claim 1 wherein the ratio of Chr:PAO is greater than 1:1.

17. A contrast agent compound as claimed in claim 1 comprising moieties of formula IV:

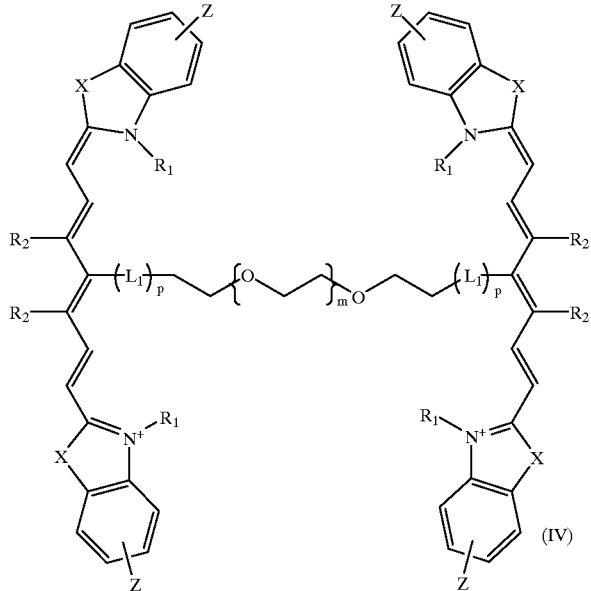

(IV)

wherein
- each $L_1$ is a group independently selected from the group consisting of an organic linker moiety and a chemical bond;
- each X is independently selected from the group consisting of O, N-$R_1$, S, Se, Te, CH=CH and $(CH_3)_2C$;
- each $R_1$ is independently selected from the group consisting of a methyl group, an ethyl group, and a $C_{3-16}$ alkyl group optionally containing one or more heteroatoms selected from the group consisting of O, N, and S, which heteroatoms are separated from one another by at least 2 carbon atoms, and which ethyl and alkyl groups optionally contain one or more hydrophilic functional groups selected from the group consisting of hydroxyl groups, carboxyl groups, sulfonate groups, sulfate groups, phosphate groups, phosphonate groups, amino groups, amino acid groups;
- each Z, of which there is at least one, is independently selected from the group consisting of H, a methyl group, an ethyl group as defined above, a $C_{3-16}$ alkyl group as defined above, a $C_{1-16}$ alkoxyl group, the alkyl portion of which is as defined above, a $C_{1-16}$ carboxyalkyl group, a $C_{1-16}$ oxycarbonylalkyl group, a sulfonate group, a hydroxyl group, a phosphate group, a $C_{1-16}$ sulfonamidoalkyl group, a phenyl-$C_{1-16}$-alkyl group, a phenoxy-$C_{1-16}$-alkyl group, a $C_{1-16}$ phenyloxyalkyl group, an oxyphenoxy-$C_{1-16}$-alkyl group, the alkyl portions each of which are as defined above, or an annulated aromatic ring which comprises a benz[e] aromatic ring, a benz[f]aromatic ring, or a benz[g] aromatic ring, each of which may be substituted by $C_{1-16}$ alkyl, $C_{1-16}$ alkoxyl, carboxyl, sulfonate, sulfonamido, phenyl, or phenoxyl groups as defined above;
- each $R_2$ is independently selected from the group consisting of H, $C_{1-16}$ alkyl as defined above, or two $R_2$ groups together with the three intervening carbons form a 5 or 6 membered carbocyclic ring optionally containing a ring heteroatom selected from the group consisting of 0, N—$R_1$ and S;
- m is an integer up to 1200; and
- each p independently is 0 or 1 when $L_1$ is an organic linker moiety.

18. A contrast agent compound as claimed in claim 1 comprising oligomeric moieties of formula V:

$$\text{Chr-(PAO-Chr)}_n \qquad (V)$$

wherein Chr and PAO are difunctional chromophores and difunctional polyalkylene oxide moieties respectively and n is an integer having a value of at least 1.

19. A contrast agent compound as claimed in claim 1 wherein the difunctional PAO moieties are selected from the group consisting of O-PEG-$CH_2$—$CH_2$—O, HN-PEG-$CH_2$—$CH_2$—NH, S-PEG-$CH_2$—$CH_2$—S, O-PEG-$CH_2$—$CH_2$—S, N-PEG-$CH_2$—$CH_2$—S and O-PEG-$CH_2$—$CH_2$—NH, wherein PEG moieties are poly(ethylene glycol) moieties derived from poly(ethylene oxide) and in which the molecular weight of any PEG moiety can be in the range from the molecular weight of monomeric ethylene diamine to about 100000.

20. A contrast agent compound as claimed in claim 1 wherein the molecular weight of the PEG moiety is in the range of 400 to 15000.

21. A contrast agent compound as claimed in claim 1 comprising at least two phthalocyanine chromophores linked to one polyalkyleneoxide moiety.

22. A contrast agent compound as claimed in claim 1 further comprising a targeting vector.

23. A contrast agent as claimed in claim 1 wherein said PAO moiety comprises a branched polyalkylene oxide.

24. A contrast agent compound as claimed in claim 1 comprising moieties of formula II:

$$L'''(\text{Chr})_m(\text{PAO})_p \qquad (II)$$

wherein
- L''' is a branched polymer with Chr and PAO groups attached, each Chr which may be the same or different is a chromophore, each PAO which may be the same or different is a polyalkylene oxide moiety, m is an integer having a value of at least two, and p is an integer having a value of at least one.

25. A contrast agent compound as claimed in claim 1 comprising moieties of formula III:

$$\text{Chr}[L^*\text{-PAO-}L^*\text{-Chr}]_n \qquad (III)$$

wherein
- each Chr which may be the same or different is a chromophore, each PAO which may be the same or different is a polyalkylene oxide moiety, n is an integer having a value of at least one, and each $L^*$ is a bond or an organic linker moiety, and wherein in such compounds there is one more Chr moiety than PAO moieties.

26. A pharmaceutical composition comprising a physiologically tolerable light-imaging contrast agent compound as claimed in claim 1 together with at least one physiologically acceptable carrier or excipient, in a sterile, pyrogen free aqueous carrier medium.

27. A method of imaging of the human or animal (e.g. mammalian, avian or reptilian) body wherein a light imaging contrast agent as claimed in claim 1 is administered to said body and an image is generated by a light imaging modality of at least a part of said body to which said agent distributes, and wherein said modality is confocal scanning laser microscopy (CSLM), optical coherence tomography (OCT), photoacoustic, acousto-optical, diffusive wave, time-resolved imaging, endoscopic, multiphoton excitation microscopy or visual observation techniques.

28. A method as claimed in claim 27 wherein said part of said body is the sentinel lymph node.

* * * * *